United States Patent [19]

Todo et al.

[11] Patent Number: 4,851,535
[45] Date of Patent: Jul. 25, 1989

[54] NICOTINIC ACID DERIVATIVES

[75] Inventors: Yozo Todo; Tetsuo Yamafuji, both of Toyama; Katsuyuki Nagumo, Kawasaki; Isao Kitayama, Toyama; Hideyoshi Nagaki, Toyama; Mikako Miyajima, Toyama; Yoshinori Konishi, Takaoka; Hirokazu Narita, Toyama; Shuntaro Takano, Toyama; Isamu Saikawa, Toyama, all of Japan

[73] Assignee: Toyama Chemical Co., Ltd., Tokyo, Japan

[21] Appl. No.: 67,264

[22] Filed: Jun. 29, 1987

Related U.S. Application Data

[62] Division of Ser. No. 819,821, Jun. 17, 1986, Pat. No. 4,704,459.

[30] Foreign Application Priority Data

| Jan. 23, 1985 | [JP] | Japan | 60-9191 |
| Feb. 18, 1985 | [JP] | Japan | 60-28397 |
| Mar. 7, 1985 | [JP] | Japan | 60-43644 |
| Apr. 3, 1985 | [JP] | Japan | 60-69061 |
| May 8, 1985 | [JP] | Japan | 60-97065 |
| Jun. 14, 1985 | [JP] | Japan | 60-129323 |

[51] Int. Cl.$^4$ .................. C07D 401/12; C07D 213/30; C07D 213/32
[52] U.S. Cl. ..................... 546/25; 546/281; 546/297; 546/312; 544/360
[58] Field of Search .................. 546/281, 297, 312, 25; 544/360

[56] References Cited

U.S. PATENT DOCUMENTS

| 3,149,104 | 9/1964 | Lesher et al. | 546/281 |
| 3,753,993 | 0/1973 | Lesher et al. | 546/281 |
| 3,950,338 | 4/1976 | Pesson | 546/281 |
| 4,017,622 | 4/1977 | Minami et al. | 546/281 |
| 4,146,719 | 3/1979 | Irikura | 546/281 |
| 4,284,629 | 0/1981 | Grohe et al. | 546/281 |
| 4,292,317 | 9/1981 | Pesson | 546/281 |
| 4,380,632 | 4/1983 | Steffen | 546/281 |
| 4,429,127 | 1/1984 | Irikara et al. | 546/281 |

FOREIGN PATENT DOCUMENTS

| 0009425 | 8/1978 | European Pat. Off. | 546/281 |
| 0004279 | 10/1979 | European Pat. Off. | 546/281 |
| 0027752 | 9/1980 | European Pat. Off. | 546/281 |
| 0078362 | 5/1983 | European Pat. Off. | 546/281 |
| 0106489 | 4/1984 | European Pat. Off. | 546/281 |
| 2341146 | 8/1972 | Fed. Rep. of Germany | 546/123 |
| 2125310 | 11/1972 | Fed. Rep. of Germany | 546/281 |
| 2338325 | 2/1974 | Fed. Rep. of Germany | 546/281 |
| 3142854 | 5/1983 | Fed. Rep. of Germany | 546/281 |
| 1147336 | 4/1969 | United Kingdom | 546/123 |
| 1484138 | 8/1977 | United Kingdom | 546/123 |
| 2034698 | 10/1979 | United Kingdom | 546/123 |

OTHER PUBLICATIONS

*Chemical Abstracts*, vol. 101, 65285v, p. 1 (1984).
*Chem. Pharm. Bull.*, vol. 30, pp. 3530–3543, (1982), Tani et al.
*Current Chemotherapy and Infectious Disease*, vol. 1, pp. 454–456, (1980), "Matsumoto et al.".
*J. Med. Chem.*, vol. 27, No. 12, pp. 1543–1548, (1984), Egawa et al.

*Primary Examiner*—Mary C. Lee
*Assistant Examiner*—J. Richter
*Attorney, Agent, or Firm*—Oblon, Spivak, McClelland, Maier & Neustadt

[57] ABSTRACT

This invention relates to a process for industrially producing a 1-substituted aryl-1,4-dihydro-4-oxonaphthyridine derivative and a salt thereof which are useful as an antibacterial agent, and also to intermediates therefor and processes for producing the intermediates.

8 Claims, No Drawings

NICOTINIC ACID DERIVATIVES

This is a division, of application Ser. No. 819,821, filed Jan. 17, 1986 now U.S. Pat. No. 4,704,459.

This invention relates to a process for producing a 1-substituted aryl-1,4-dihydro-4-oxonaphthyridine derivative of the formula (I-1) or a salt thereof:

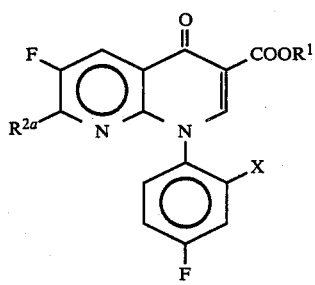

wherein $R^1$ represents a hydrogen atom or a carboxyl-protecting group; $R^{2a}$ represents a 3-amino-1-pyrrolidinyl group in which the amino group may be protected, or a 1-piperazinyl group in which the imino group may be protected; and X represents a hydrogen atom or a fluorine atom, said derivative having a strong antibacterial activity against Gram-positive bacteria and Gram-negative bacteria, to intermediates for producing said derivative, and to processes for producing the intermediates.

In Program and Abstracts of the 24th I.C.A.A.C., pages 102 to 104 and Japanese Patent Application Kokai (Laid-Open) No. 228,479/85, it is disclosed that 1-substituted aryl-1,4-dihydro-4-oxonaphthyridine derivatives of the formula (I-1) and salts thereof have a strong antibacterial activity against Gram-positive bacteria and Gram-negative bacteria and when they are orally or parenterally administered a high blood level is obtained, and they have excellent properties such as high safety and the like.

This invention relates to the following processes for producing compounds of the formula (I) or salts thereof, and producing intermediates therefor, and also to intermediates of formulas (II), (I-3) and (V).

o Processes

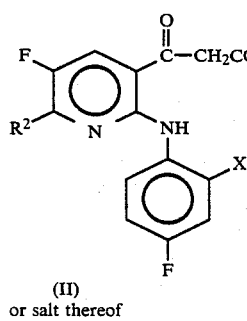

(II) or salt thereof

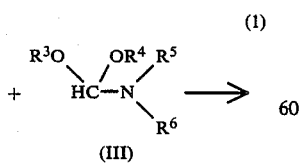

(III)

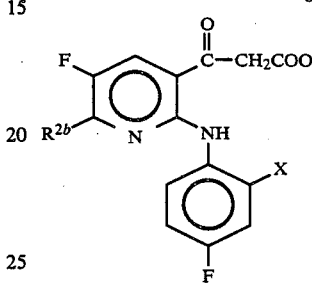

(I) or salt thereof

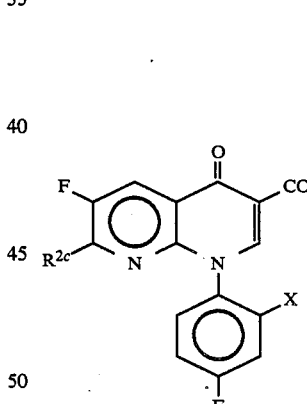

(II-1) or salt thereof

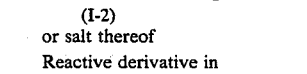

(Ib) or salt thereof

(I-2) or salt thereof
Reactive derivative in the carboxyl group of the compound (V-1)

$+ R^{2a}H$ (IV)
or salt thereof

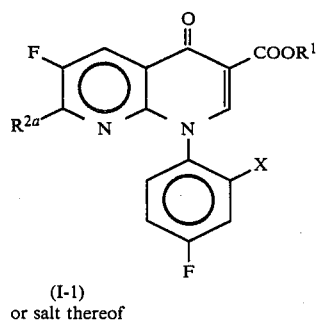

(I-1) or salt thereof

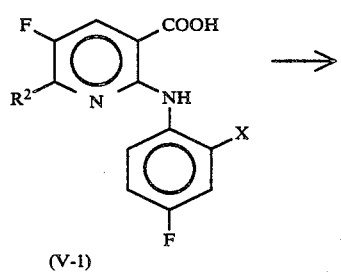

(V-1)

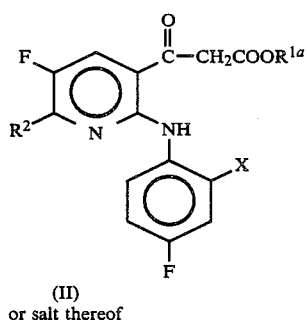

(II) or salt thereof

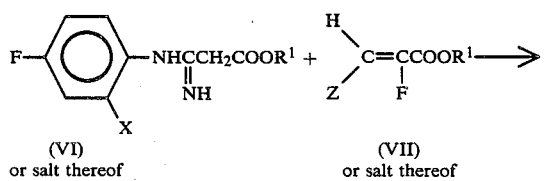

(VI) or salt thereof    (VII) or salt thereof

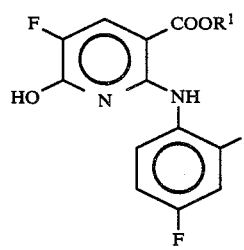

(Va) or salt thereof

0 Intermediates

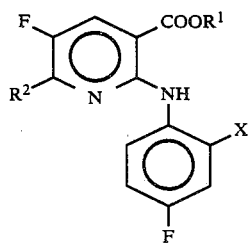

(V)

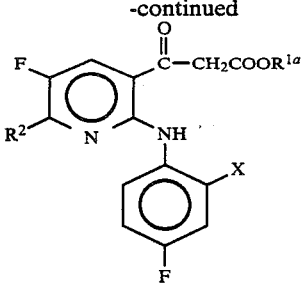

(II)

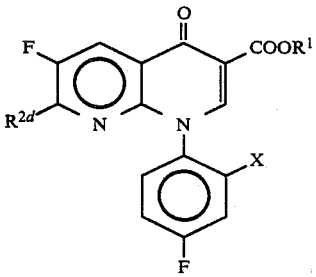

(I-3)

In the above general formulas (I), (Ib), (I-2), (I-3), (II-1), (II), (III), (IV), (V), (Va), (V-1), (VI) and (VII), $R^{1a}$ represents a carboxyl-protecting group; $R^2$ represents a halogen atom, a hydroxyl group, an azido group, an optionally substituted alkoxy, alkylthio, arylthio, alkanesulfinyl, arenesulfinyl, alkanesulfonyl, arenesulfonyl, alkanesulfonyloxy, arenesulfonyloxy, dialkoxyphosphinyloxy or diaryloxyphosphinyloxy group, a 3-amino-1-pyrrolidinyl group in which the amino group may be protected or a 1-piperazinyl group in which the imino group may be protected; $R^{2b}$ represents a hydroxyl group or an optionally substituted alkoxy, alkanesulfonyl, arenesulfonyl, alkanesulfonyloxy, arenesulfonyloxy, dialkoxyphosphinyloxy or diaryloxyphosphinyloxy group; $R^{2c}$ represents an azido group or an optionally substituted arylthio, alkanesulfinyl, arenesulfinyl, alkanesulfonyl, arenesulfonyl, alkanesulfonyloxy, arenesulfonyloxy, dialkoxyphosphinyloxy or diaryloxyphosphinyloxy group; $R^{2d}$ represents a hydroxyl group, an azido group or an optionally substituted alkoxy, alkylthio, arylthio, alkanesulfinyl, arenesulfinyl, alkanesulfonyl, arenesulfonyl, alkanesulfonyloxy, arenesulfonyloxy, dialkoxyphosphinyloxy or diaryloxyphosphinyloxy group; and $R^3$ and $R^4$, which may be the same or different, represent alkyl or cycloalkyl groups, or may be linked to form an alkylene group which forms a ring together with the

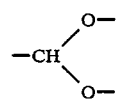

group. $R^5$ and $R^6$, which may be the same or different, represent alkyl groups or may form a heterocyclic ring together with the adjacent nitrogen atom. Y represents a halogen atom; Z represents a removable group which may be a halogen atom, a hydroxyl group or an optionally substituted acyloxy, alkanesulfonyloxy, arenesulfonyloxy, dialkoxyphosphinyloxy or diaryloxyphosphinyloxy group; and $R^1$, $R^{2a}$ and X have the same meanings as defined above.

The above-mentioned production processes and intermediates are used in the following production routes and enable the compounds of the formula (I-1) or salts thereof to be produced advantageously in industry.

Production Routes
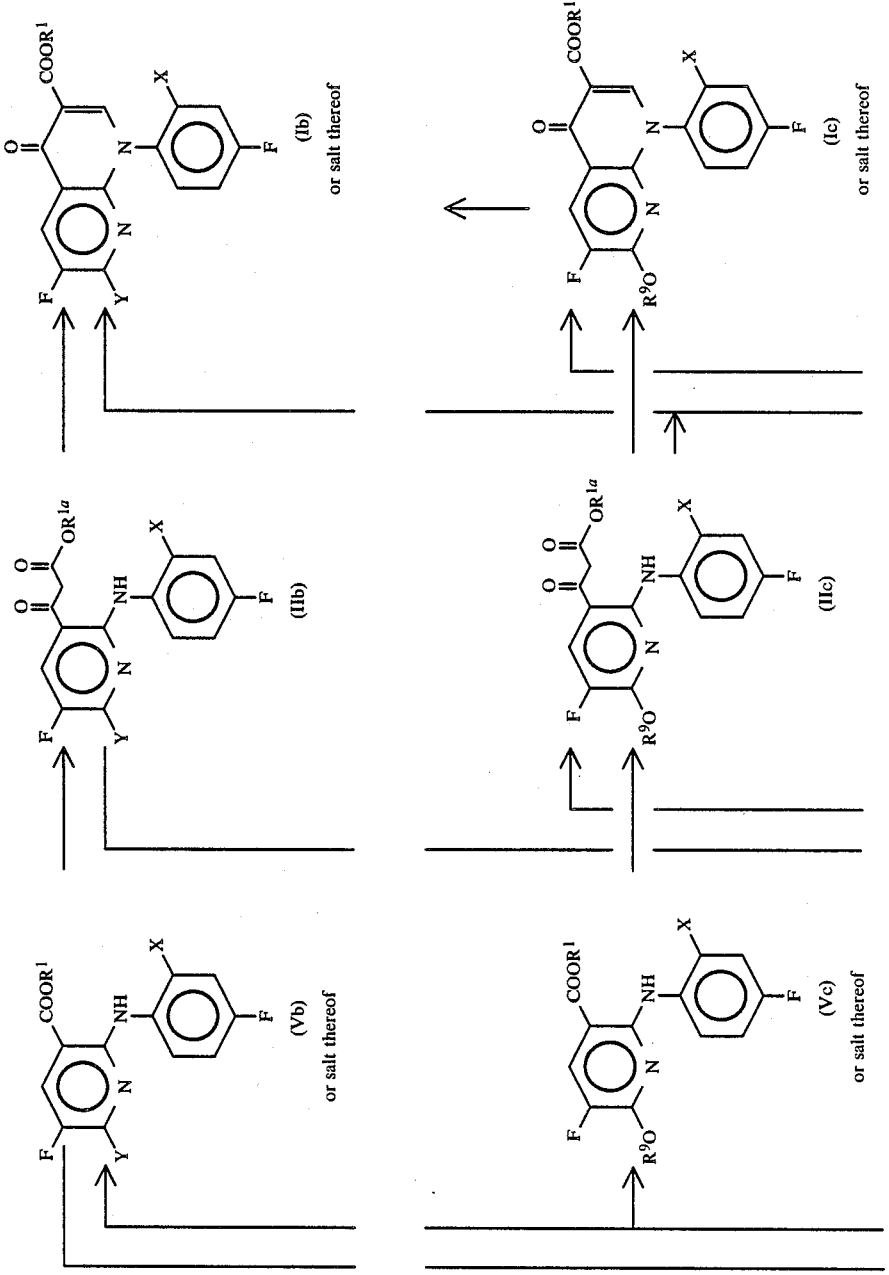

-continued
Production Routes
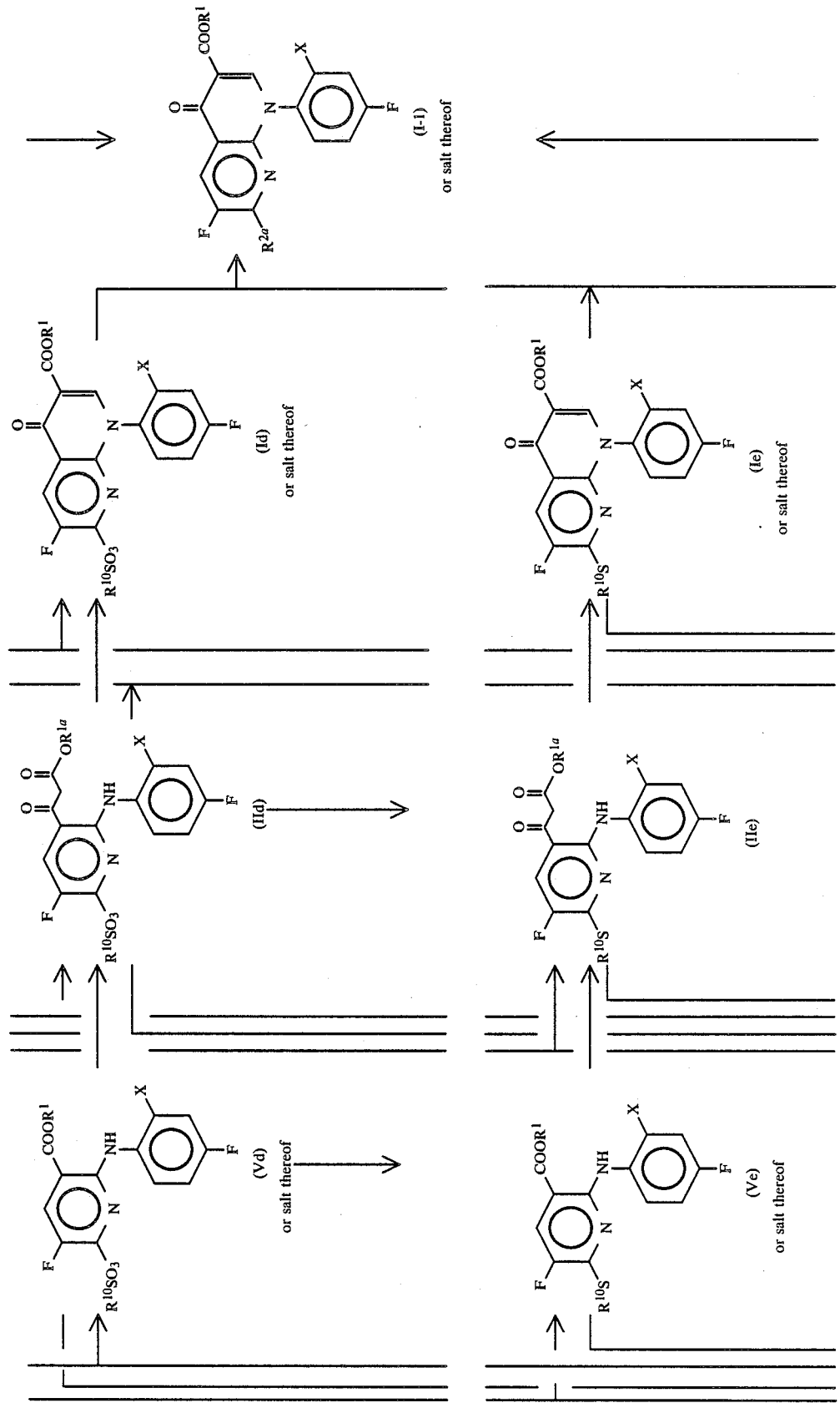

-continued
Production Routes
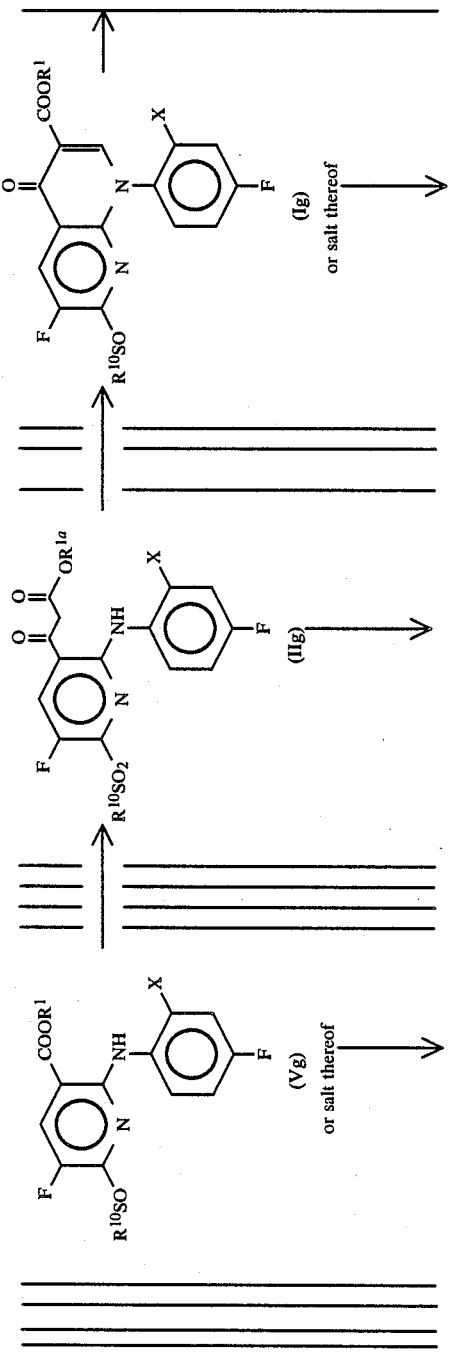
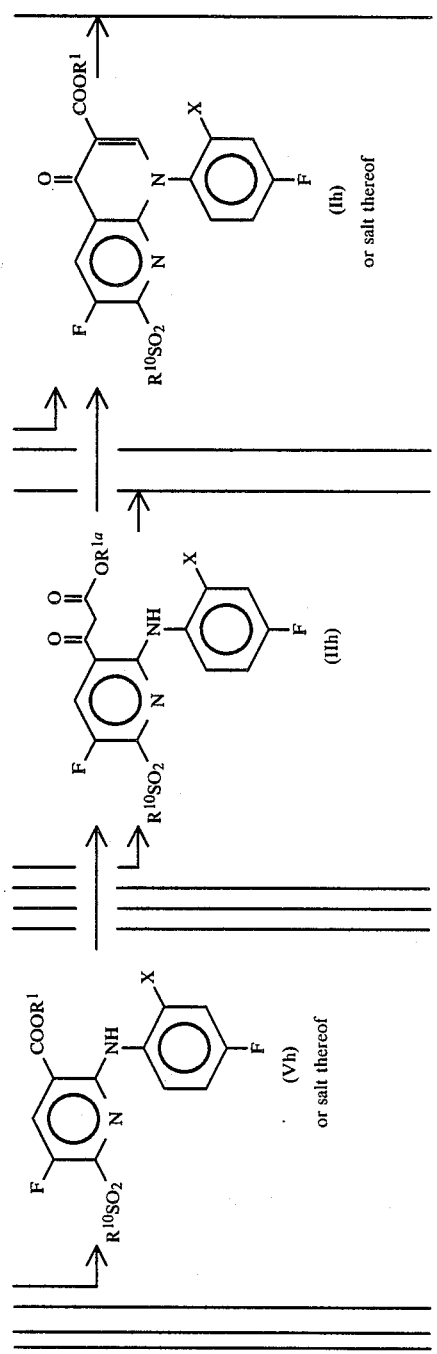

-continued
Production Routes
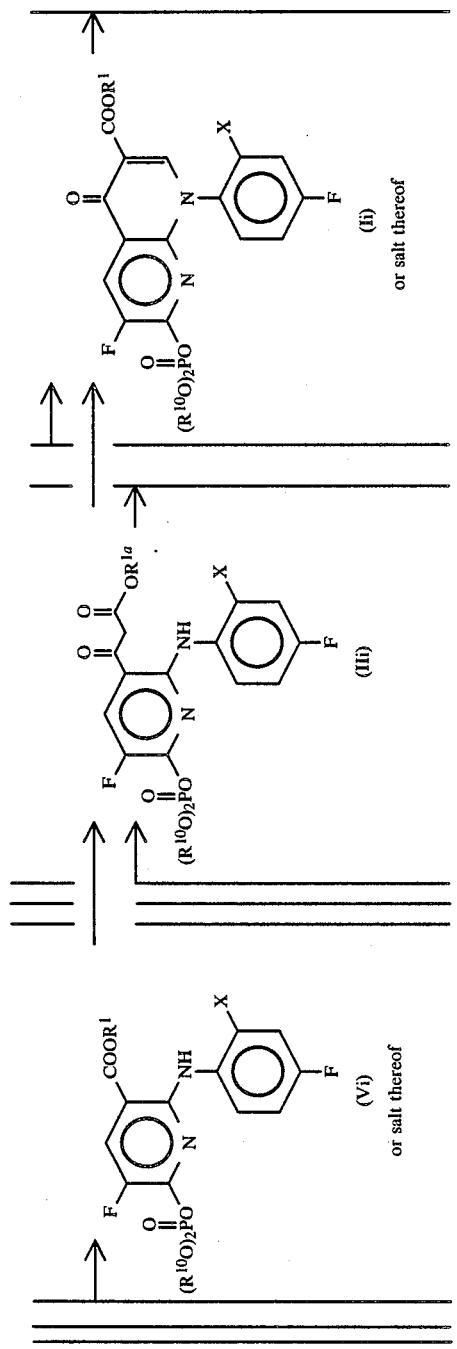
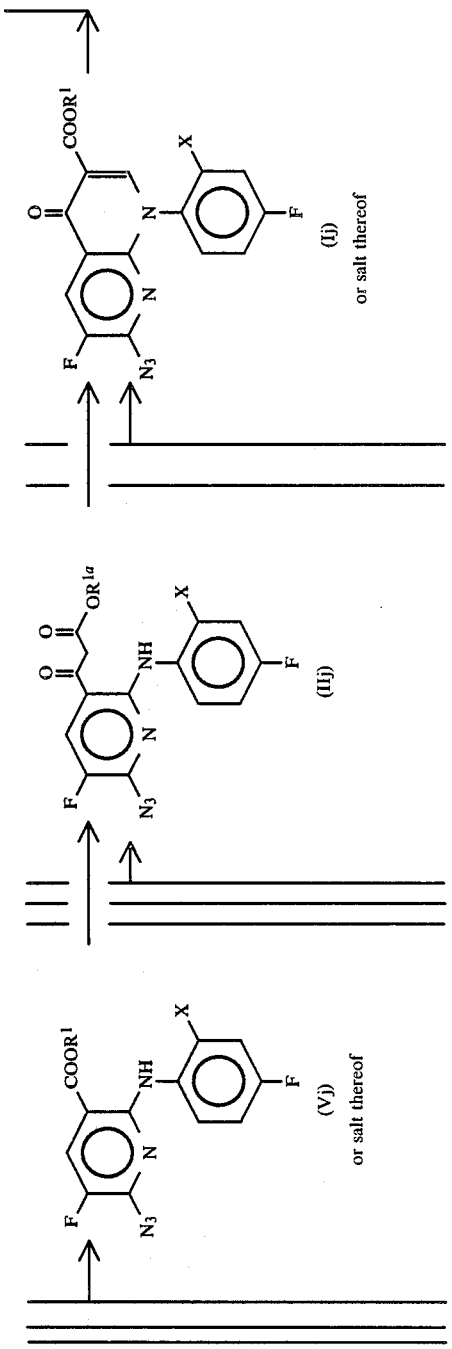

-continued
Production Routes
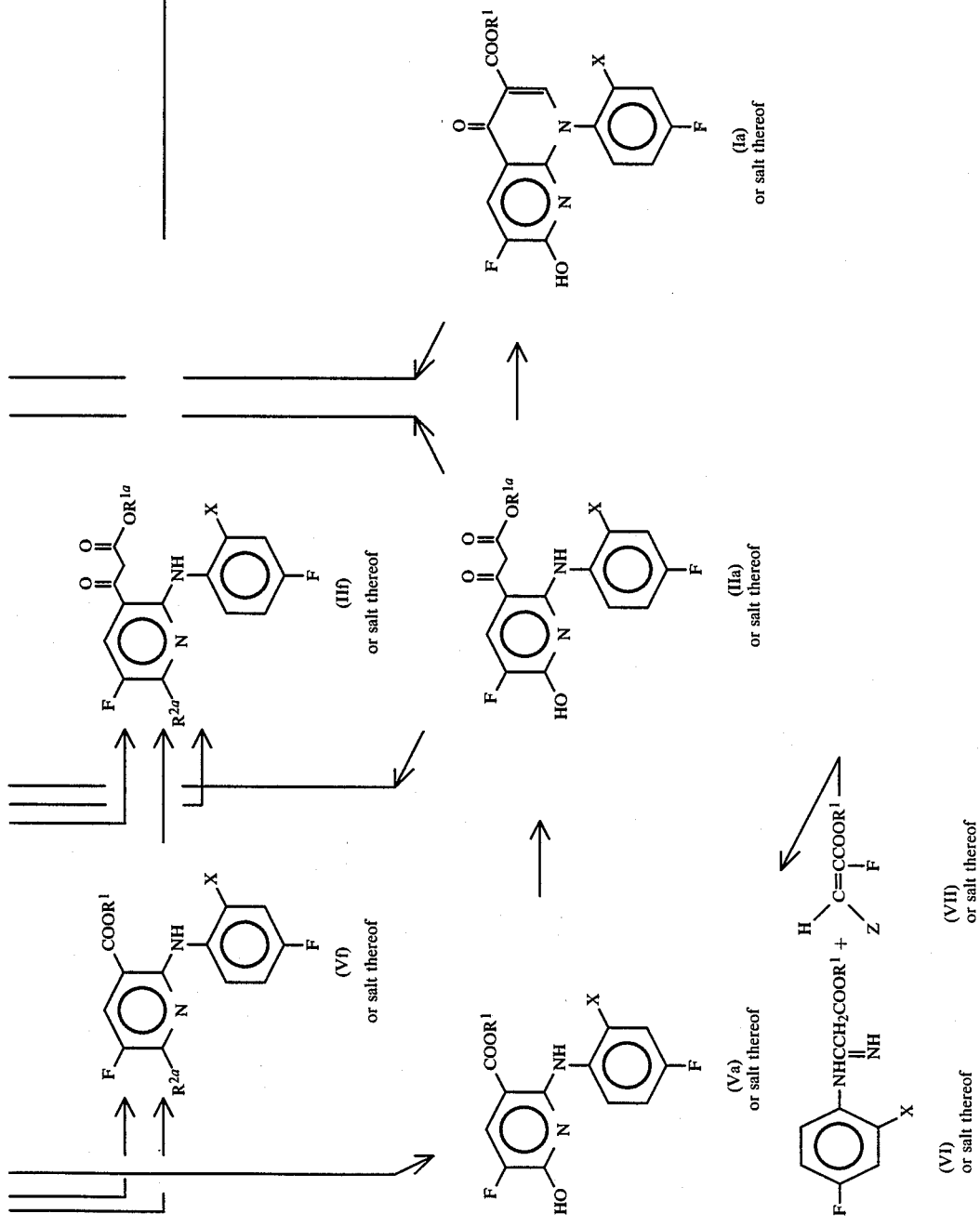

In the above-mentioned production routes, $R^9O-$ represents the same alkoxy group as mentioned in $R^2$; $R^{10}SO-$ respesents the same alkanesulfonyloxy or arenesulfonyloxy group as mentioned in $R^2$; $R^{10}S-$ respesents the same alkylthio or arylthio group as mentioned in $R^2$; $R^{10}SO-$ represents the same alkanesulfinyl or arenesulfinyl group as metioned in $R^2$; $R^{10}SO-$ represents the same alkanesulfonyl or arenesulfonyl group as mentioned in $R^2$;

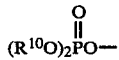

represents the same dialkoxyphosphinyloxy or diaryloxyphosphinyloxy group as mentioned in $R^2$; each of these groups for $R^9$ and $R^{10}$ may be substituted by at least one of the substituents mentioned as to the substituted for $R^2$; and $R^1$, $R^{1a}$, $R^{2a}$, X, Y and Z have the same menanings as defined above.

An object of this invention is to provide a process for producing industrially and easily a 1-substituted aryl-1,4-dihydro-4-oxonaphthyridine derivative of the formula (I-1) or a salt thereof which are useful as an antibacterial agent.

Another object of this invention is to provide an intermediate for producing a 1-substituted aryl-1,4-dihydro-4-oxonaphthyridine derivative of the formula (I-) or a salt thereof.

A further object of this invention is to provide a process for producing the intermediate industrially and easily.

This invention is explained in detail below.

In this specification, the carboxyl-protecting group for $R^1$ and $R^{1a}$ includes those which are conventionally used in this field, for example, the conventional carboxyl-protecting groups mentioned in Japanese Patent Application Kokai (Laid-Open) No. 80,665/84 such as alkyl, benzyl, pivaloyloxymethyl, trimethylsilyl and the like.

The halogen atoms for $R^2$, Y and Z include, for example, fluorine, chlorine, bromine and iodine. In $R^2$, the alkoxy group includes, for example, $C_{1-12}$alkoxy groups such as methoxy, ethoxy, n-propoxy, isobutoxy, pentyloxy, hexyloxy, heptyloxy, octyloxy, dodecyloxy and the like; the alkylthio group includes, for example, $C_{1-12}$alkylthio groups such as methylthio, ethylthio, n-propylthio, isopropylthio, isobutylthio, ter.-butylthio, pentylthio, hexylthio, heptythio, octylthio, dodecylthio and the like; the arylthio group includes, for example, phenylthio, naphthylthio and the like; the alkanesulfinyl groups includes, for example, $_{1-5}$alkanesulfinyl groups such as methanesulfinyl, ethanesulfinyl and the like; the arenesulfinyl group includes, for example, benzenesulfinyl, naphthalenesulfinyl and the like; the alkanesulfonyl groups includes, for example, $C_{1-5}$alkanesulfonyl groups such as methanesulfonyloxy, ethanesulfonyl and the like; the arenesulfonyl group includes, for example, benzenesulfonyl, naphthalenesulfonyl and the like; the alkanesulfonyloxy group includes, for example, $C_{1-5}$alkanesulfonyloxy groups such as methanesulfonyloxy, ethanesulfonyloxy and the like; the arenesulfonyloxy group includes, for example, bexenesulfonyloxy, naphthalenesulfonyloxy and the like; the dialkoxyphosphinyloxy group includes, for example, di-$C_{1-5}$alkoxyphosphinyloxy groups such as dimethoxyphosphinyloxy, diethoxyphosphinyloxy, dipropoxyphosphinyloxy, dibutoxyphosphinyloxy and the like; the diaryloxyphosphinyloxy group includes, for example, diphenoxyphosphinyloxy and the like.

The above-mentioned alkoxy, alkylthio, arylthio, alkanesulfinyl, arenesulfinyl, alkanesulfonyl, arenesulfonyl, alkanesulfonyloxy, arenesulfonyloxy, dialkoxyphosphinyloxy and diaryloxyphosphiyloxy groups for $R^2$ may be substituted by at least one substituent selected from the group consisting of halogen atoms such as fluorine, chlorine, bromine, iodine and the like; nitro group; lower alkyl groups such as methyl, ethyl, n-propyl, isopropyl, n-butyl, isobutyl, sec.-butyl, tert.-butyl and the like; lower alkoxy groups such as methoxy, ethoxy, n-propoxy, isopropoxy, n-butoxy, isobutoxy, sec.-butoxy, tert.-butoxy and the like; etc.

The alkoxy, alkanesulfonyl, arenesulfonyl, alkanesulfonyloxy, arenesulfonyloxy, dialkoxyphosphinyloxy and diaryloxyphosphinyloxy groups for $R^{2b}$; the arylthio, alkanesulfinyl, arenesulfinyl, alkanesulfonyl, arenesulfonyl, alkanesulfonyloxy, arenesulfonyloxy, dialkoxyphosphinyloxy and diaryloxyphosphinyloxy groups for $R^{2c}$; and the alkoxy, alkylthio, arylthio, alkanesulfinyl, arenesulfinyl, alkanesulfonyl, arenesulfonyl, alkanesulfonyloxy, arenesulfonyloxy, dialkoxyphosphinyloxy and diaryloxyphosphinyloxy groups for $R^{2d}$ includes those mentioned as to $R^2$. Each of these groups for $R^{2b}$, $R^{2c}$ and $R^{2d}$ may be substituted by at least one of the substituents mentioned as to the substituent for $R^2$.

The protecting groups for the amino and imino groups in the 3-amino-1-pyrrolidinyl group in which the amino group may be protected and the 1-piperazinyl group in which the imino group may be protected for $R^2$ and $R^{2a}$ include those which are conventionally used in this field, for example, the conventional amino-protecting and imino-protecting groups mentioned in Japanese Patent Application Kokai (Laid-Open) No. 80,665/84 such as formyl, acetyl, ethoxycarbonyl, benzyloxycarbonyl, N,N-dimethylaminomethylene and the like.

The optionally substituted alkanesulfonyloxy, arenesulfonyloxy, dialkoxyphosphinyloxy and diaryloxyphosphinyloxy groups for Z include those mentioned as to $R^2$, and the optionally substituted acyloxy group for Z includes, for example, acetyloxy, benzoyloxy and the like.

The acetals of the N,N-di-substituted formaide of the formula (III) include acetals of the conventionally known N,N-di-substituted formamides, for example; N,N-di-$C_{1-5}$alkylformamido-di-$C_{1-5}$alkylacetals such as N,N-dimethylformamido-dimethylacetal, N,N-dimethylformamido-diethylacetal, N,N-dimethylformamido-dipropylacetal, N,N-dimethylformamido-dibutylacetal, N,N-dimethlformamido-dineopenetylacetal, N,N-diethylformamido-dimethylacetal, N,N-dipropylformamido-dimethylacetal, N,N-dibutylformamido-dimethylacetal and the like; N,N-di-$C_{1-5}$alkylformamido-di-$C_{3-6}$cycloalkylacetals such as N,N-dimethylformamido-dicyclohexylacetal and the like; N,N-di-$C_{1-5}$alkyformamido-5-or 6-membered cyclic acetals such as 2dimethylamino-1,3-dioxolane, 2-dimethylaminotetramethyl-1,3-dioxlane, 2-dimethylamino-1,3-dioxane and the like; N-formyl-nitrogen-containing saturated heterocyclic di-$C_{1-5}$alkylacetals which may contain an oxygen atom in addition to the nitrogen atom such as N-dimethoxymethlpyrrolidine, N-dimethoxymethylmorpholine, N-dimethoxymethylpiperidine and the like; etc.

The Vilsmeier reagent derived from N,N-di-substituted formamide includes thos conventionally known as a Vilsmeier reagent derived from N,N-di-substituted formamides, and specifically includes, for example, Vilsmeier reagents obtained by reacting N,N-di-substitued formamides of the formula:

(VIII)

wherein $R^7$ and $R^8$, which may be the same or different, represent alkyl or aryl groups, or may form a nitrogen-containing saturated heterocyclic group together with the adjacent nitrogen atom, and said ring may contain a sulfur or oxygen atom in addition to the nitrogen atom, with an inorganic or organic halides which are conventionally known in the Vilsmeier reaction.

The N,N-di-substituted formamides of the formula (VIII) include, for example, N,N-di-$C_{1-5}$alkylformamides such as N,N-dimethylformamide, N,N-diethylformamide, N,N-dibutylformamide and the like; N-$C_{1-5}$alkyl-N-arylformamides such as N-methyformanilide and the like; N,N-diaryl-formamides such as N,N-diphenylformamide and the like; N-formyl-nitrogen containing saturated heterocyclic groups which may contain on oxygen or sulfur atom in addition to the nitrogen atom such as N-formylpyrrolidine, N-formylpiperidine, N-formylmorpholine, N-formylthiomorpholine and the like; etc.

The inorganic and organic halides include those which are conventionally known in the preparation of Vilsmeier reagents, and the inorganic halide includes, for example, phosphorus halides such as phosphorus oxychloride, phosphorus oxybromide, phosphorus trichloride, phosphorus tribromide, phosphorus pentachloride and the like; sulfur halides such as thionyl chloride, thionyl bromide, sulfuryl chloride and the like; etc. The organic halide includes, for example, carbonyl halides such as phosgene, diphosgene, ethyl chlorocarbonate and the like; oxalyl halides such as oxalyl chloride and the like; organic phosphorus halides such as dibromotriphenylphosphorane and the like; etc.

In each of the above-mentioned compounds, the salt includes salts at the basic groups such as amino group and the like and at the acidic groups such as carboxyl group, hydroxyl group and the like. The salt at the basic group includes, for example, salts with mineral acids such as hydrochloric acid, hydrobromic acid, sulfuric acid and the like; salts with organic carboxylic acids such as oxalic acid, citric acid, trifluoroacetic acid, and the like; salts with sulfonic acids such as methanesulfonic acid, p-toluenesulfornic acid, naphthalenesulfonic acid and the like; etc. The salt at the acidic group includes, for example, salts with alkali metals such as sodium, potassium and the like; salts with alkaline earth metals such as megnesium, calcium and the like; ammonium salts; and salts with nitrogen-containing organic bases such as procain, dibenzylamine, N-benzyl-$\beta$-phenethylamine, 1-ephenamine, N,N-dibenzylethylenediamine, triethylamine, pyridine, N,N-dimethylaniline, N-methylpiperdine, N-methylmorpholine, diethylamine, dicyclohexylamine and the like.

The process of this invention and processes for producing the present compounds are described in detail below.

(1) The compound of the formula (Va) or a salt thereof can be produced by reacting a compound of the formula (VI) with a compound of the formula (VII) or a salt thereof prepared based on the method described in Bull. Soc. Chim. Fr., pp. 1,165–1,169 (1975), J. Chem. Soc. (C). pp. 2206–2207 (1967) and Program and Abstracts of the 105th Meeting of Japanese Pharmaceutical Society p. 523 (1985). The compound of formula (VI) or its salt can be synthesized by reacting a compound of the formula (A):

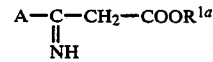

wherein $R^{1a}$ represents a carboxyl-protecting group and A is an aryloxy or arylthio group, with a compound of the formula B:

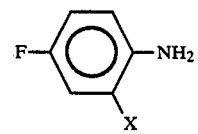
(B)

wherein X has the same meaning as defined above. This reaction is described in British Pat. No. 1,409,987.

The solvent which may be used in this reaction may be any solvent inert to the reaction, and includes, for example, water; alcohols such as methanol, ethanol, isopropyl alcohol, butyl alcohol, ethylene glycol, methyl Cellosolve and the like; aromatic hydrocarbons such as benzene, toluene and the like; halogenated hydrocarbons such as methylene chloride, chloroform, dichloroethane and the like; ethers such as tetrahydrofuran, dioxane, anisole, diethylene glycol dimethyl ether, dimethyl Cellosolve and the like; nitriles such as acetonitrile and the like; ketones such as acetone, methyl ethyl ketone and the like; esters such as methyl acetate, ethyl acetate and the like; amides such as N,N-dimethylformamide, N,N-dimethylacetamide and the like; sulfoxides such as dimethylsulfoxide and the like; etc. These solvents may be used in admixture of two or more.

The condensing agent includes, for example, sodium hydroxide, potassium hydroxide, potassium tert.-butoxide, sodium hydride, sodium methoxide, sodium ethoxide, potassium methoxide, potassium ethoxide, and the like.

In this reaction, the amount of the compound of the formula (VII) or a salt thereof used is not critical though it is at least equimolar to, preferably 1.0 to 3.0 moles per mole of, the compound of the formula (VI). Also, this reaction may be effected usually at 0° to 150° C., preferably 15° to 100° C., for 5 minutes to 30 hours.

(2) Alkylation

The compound of the formula (Vc) or a salt thereof, the compound of the furmula (IIc) and the compound of the formula (Ic) or a salt thereof can be produced by reacting a compound of the formula (Va) or a salt thereof, a compound of the formula (IIa) or a salt thereof or a compound of the formula (Ia) or a salth thereof, respectively, with an alkylating agent in the presence or absence of an acid-binding agent.

The solvent which may be used in the reaction may be any solvent inert to the reaction, and includes, for example, water; alcohols such as methanol, ethanol, isopropyl alcohol, and the like; ethers such as diethyl ether, tetrahydrofuran, dioxane and the like; ketones such as acetone, methyl ethyl ketone and the like; esters such as methyl acetate, ethyl acetate and the like; aromatic hydrocarbons such as benzene, toluene and the like; halogenated hydrocarbons such as methylene chloride, chloroform and the like; amides such as N,N-dimethylformamide, N,N-dimethylacetamide and the like; sulfoxides such as dimethylsulfoxide and the like; etc. These solvents may be used in admixture of two or more. The alkylating agent includes, for example, diazoalkanes such as diazomathane, diazoethane and the like; dialkyl sulfates such as dimethyl sulfate, diethyl sulfate and the like; alkyl halides such as methyl iodide, methyl bromide, ethyl bromide and the like; etc.

When a dialkyl sulfate or an alkyl halide is used as the alkylating agent, the acid-binding agent may be used. The said acid-binding agent includes, for example, inorganic bases such as an alkali hydroxide, and alkali carbonate and the like; and amines such as trimethylamine, triethylamine, tributylamine, N,methylpiperidine, N-methylmorpholine, lutidine, colidine, pyridine and the like. The amount of the dialkyl sulfate or the alkyl halide which are the alkylating agents and the amount of the optionally used acid-binding agent are at least equimolar to, preferably 1.0 to 2.0 moles per mole of, the compound of the formula (Va) or a salt thereof, the compound of the formula (IIa) or a salt thereof or the compound of the formula (Ia) or a salt thereof. In this case, the reaction may be effected usually at 0° to 150° C., preferably 0° to 50° C., for 5 minutes to 30 hours.

When a diazoalkane is used as the alkylating agent, the amount thereof is at least equimolar to, preferably 1.0 to 1.5 moles per mole of, the compound of the formula (Va) or a salt thereof, the compound of the formula (IIa) or a salt thereof, or the compound of the formula (Ia) or a salt thereof. In this case, the reaction may be effected usually at 0° to 50° C., preferably 0° to 25° C., for 5 minutes to 30 hours.

(3) Halogenation (i) The compounds of the formulas (Ib) and (Vb) or salts thereof can be obtained by reacting compounds of the formulas (Ic) and (Va) or a salts thereof, respectively, with a halogenating agent. The solvent which may be used in the reaction may be any solvent inert to the reaction, and includes, for example, aromatic hydrocarbons such as benzene, toluene, xylene and the like; halogenated hydrocarbons such as methylene chloride, chloroform, dichloroethane and the like; amides such as N,N-dimethylformamide, N,N-dimethylacetamide and the like; etc. These solvents may be used in admixture of two or more. The halogenating agent includes, for example, phosphorus oxychloride, phosphorus oxybromide, phosphorus pentachloride, phosphorus pentabromide, phosphorus trichloride, thionyl chloride, phosgene and the like, and these agents may be used in admixture of two or more and may be used as a solvent. The amount of the halogenating agent used is at least equimolar to the compound of the formula (Va) or a salt thereof. The reaction may be effected usually at 0° to 150° C., preferably 50° to 110° C., for 30 minutes to 30 hours.

(ii) The compound of the formula (Ib) or a salt thereof can be obtained by reacting a compound of the formula (IIa) or a salt thereof or a compound of the formula (IIc), (IId), (IIh) or (IIi) [namely, the compounds of the formula (II1) or salts thereof] with a Vilsmeier reagent derived from an N,N-di-substituted formamide. The solvent which may be used in the reaction may be any solvent inert to the reaction, and includes, for example, aromatic hydrocarbons such as benzene, toluene, dichlorobenzene and the like; halogenated hydrocarbons such as methylene chloride, chloroform, dichloroethane and the like; formamides such as N,N-dimethylformamide and the like; etc. These solvents may be used in admixture of two or more.

When the Vilsmeier reagent is in solution, it may be used as the solvent. In the reaction, the amount of the Vilsmeier reagent used is at least equimolar to, preferably 2.0 to 5.0 moles per mole of, the compound of the formula (II-1). The reaction may be effected usually at 0° to 150° C., preferably 0° to 90° C., for 5 minutes to 30 hours.

The Vilsmeier reagent derived from N,N-di-substituted formamides can be obtained by reacting an N,N-di-substituted formamide with the inorganic or organic halide described above, in equimolar amounts, and the preparation of this Vilsmeier reagent may be conducted usually at 0° to 25° C. for 5 minutes to 1 hour. Also, the Vilsmeier reagent may be prepared in situ.

The reaction conditions are not limited to those mentioned above, and may be varied depending upon the reactants used.

(4) Sulfonylation

The compound of the formula (Vd) or salt thereof, the compound of the formula (IId) and the compound of the formula (Id) or a salt thereof can be obtained by reacting a compound of the formula (Va) or a salt thereof, a compound of the formula (IIa) or a salt thereof and a compound of the formula (Ia) or a salt thereof, respectively, with a sulfonylating agent in the presence or absence of an acid-binding agent. The solvent which may be used in the reaction may be any solvent inert to the reaction, and includes, for example, water; aromatic hydrocarbons such as benzene, toluene, xylene and the like; ethers such as dioxane, tetrahydrofuran, anisole, diethylene glycol dimethyl ether and the like; halogenated hydrocarbons such as methylene chloride, chloroform, dichloroethane and the like; ketones, such as acetone, methyl ethyl ketone and the like; nitriles such as acetonitrile and the like; amides such as N,N-dimethylformamide, N,N-dimethylacetamide and the like; sulfoxides such as dimethylsulfoxide and the like; hexamethylphosphoramide: pyridine; etc. These solvents may be used in admixture of two or more. The sulfonylating agent includes, for example, alkanesulfonyl and arenesulfonyl halides such as methanesulfonyl chloride, trifluoromethanesulfonyl chloride, ethanesulfonyl chloride, 1-methylethanesulfonyl chloride, 1,1-dimethylethanesulfonyl chloride, benzenesulfonyl chloride, toleuensulfonyl chloride, nitrobenzenesulfonyl chloride, chlorobenzenesulfonyl chloride, 2,5-dichlorobenzenesulfonyl chloride, 2,3,4,-tricholorbenzenesulfonyl chloride, 2,4,5-trichlorobenzenesulfonyl chloride, 2,4,6-trimethylbenzenesulfonyl chloride, 2,4,6-triisopropylbenzenesulfonyl chloride, naphthanenesulfonyl chloride and the like; alkanesulfonic and arenesulfonic anhydrides such as methanesulfonic anhydride, toleuenesulfonic anhydride and the like; etc. Also, the acid-binding agent includes, for example, inorganic and organic bases such as triethylamine, di-isopropylethylamine, 1,8-diazabicyclo[5,4,0]undec-7-ene(DBU), pyridine, potassium tert.-butoxide, sodium hydride, alkali hydroxides, alkali carbonates and the like.

The amount of the sulfonylating agent used and the amount of the optionally used acid-binding agent are at least equimolar to, preferably 1.0 to 2.0 moles per mole of, the compound of the formula (Va) or a salt thereof, the compound of the formula (IIa) or a salt thereof, or the compound of the formula (Ia) or a salt thereof. The reaction may be effected usually at −10° to 150° C., preferably 0° to 80° C., for 5 minutes to 30 hours.

(5) Thiolation

In order to produce the compound of the formula (IIe) from the compound of the formula (IIb) or a salt thereof or the compound of the formula (IId) and to produce the compound of the formula (Ve) or a salt thereof from the compound of the formula (Vb) or (Vd) or a salt thereof, the compound of the formula (IIb), (IId), or (Vb) or (Vd) or a salt thereof can be reacted with a thiol or a salt thereof such as methanethiol, ethanethiol, n-propanethiol, 1-methylethanethiol, isobutanethiol, 1,1-dimethylethanethiol, pentanethiol, hexanethiol, heptanethiol, octanethiol, dodecanethiol, thiophenol, naphthalenethiol or the like in the presence or absence of an acid-binding agent. The salt or the thiol includes, for example, salts at the acidic groups as described in the case of the compound of the formula (I) or the like. The solvent which may be used in the reaction may be any solvent inert to the reaction, and includes, for example, aromatic hydrocarbons such as benzene, toluene, xylene and the like; ethers such as dioxane, tetrahydrofuran, anisole, diethylene glycol diethyl ether and the like; halogenated hydrocarbons such as methylene chloride, chloroform, dichloroethane and the like; amides such as N,N-dimethylformamide, N,N-dimethylacetamide and the like; sulfoxides such as dimethylsulfoxide and the like; etc. These solvents may be used in admixture of two or more. The acid-binding agent includes, for example, inorganic bases such as alkali hydroxides, sodium hydride, alkali carbonates and the like; and organic bases such as trimethylamine, triethylamine, di-isopropylethylamine, DBU, potassium tert.-butoxide, tributylamine, pyridine, N-methylpiperidine, N-methylmorpholine, lutidine, collidine and the like. The amount of the thiol or a salt thereof used and the amount of the optionally used acid-binding agent are at least equimolar to, preferably 1.0 to 2.0 moles per mole of, the compound of the formula (IIb) or (IId) or the compound of the general formula (Vb) or (Vd) or salts thereof. The reaction may be effected usually at 0° to 150° C., preferably 0° to 70° C., for 5 minutes to 30 hours.

(6) Phosphorylation

The compounds of the formulas (Ii), (IIi) and (Vi) or salts thereof can be obtained by reacting the compounds of the formulas (Ia), (IIa) and (Va) or salts thereof, respectively, with a phosphorylating agent in the presence or absence of an acid-binding agent.

The solvent which may be used in the reaction may be any solvent inert to the reaction, and includes, specifically the same solvents as used in the above-mentioned sulfonylation. The phosphorylating agent includes, for example, dialkylphosphoryl halides such as dimethylphosphoryl chloride, diethylphosphoryl chloride, dipropylphosphoryl chloride, dibutylphosphoryl chloride and the like; diarylphosphoryl halides such as diphenylphosphoryl chloride and the like; etc.

The acid-binding agent which may be used in the reaction includes specifically the same acid-binding agents as used in the above-mentioned sulfonylation. The amount of the phosphorylating agent used and the amount of the optionally used acid-binding agent are at least equimolar to, preferably 1.0 to 1.5 moles per mole of, the compound of the formula (Ia), (IIa) or (Va) or a salt thereof. The reaction may be effected usually at 0° to 150° C., preferably 0° to 50° C., for 5 minutes to 30 hours.

(7) Azidation

The compound of the formula (IIj) or the compounds of the formulas (Ij) and (Vj) or salts thereof can be obtained by reacting the compound of the formula (IIa) or a salt thereof and the compounds of the formulas (Ia) and (Va) or salts thereof, respectively, with an azidating agent in the presence or absence of an acid-binding agent. The solvent which may be used in the reaction may be any solvent inert to the reaction, and includes specifically the same solvents as used in the above-mentioned sulfonylation.

Also, the azidating agent includes, for example, dialkylphosphoryl azides such as diethylphosphoryl azide and the like; diarylphosphoryl azides such as diphenylphosphoryl azide and the like; etc. The acid-binding agent which may be used in the reaction includes specifically the same acid-binding agents as used in the above-mentioned sulfonylation.

The amount of the azidating agent used and the amount of the optionally used acid-binding agent are at least equimolar to, preferably 1.0 to 3.0 moles per mole of, the compound of the formula (Ia), (IIa) or (Va) or a salt thereof. The reaction may be effected usually at 0° to 150° C., preferably 15° to 100° C., for 5 minutes to 30 hours.

(8) Oxidation

The compounds of the formulas (IIg) and (IIh) can be produced by reacting the compound of the formula (IIe) with an oxidizing agent under the respective conditions; the compounds of the formulas (Ig) and (Ih) or salts thereof can be produced by reacting the compound of the formula (Ie) or salt thereof with an oxidizing agent under the respective conditions; and the compounds of the formulas (Vg) and (Vh) or salts thereof can be produced by reacting the compound of the formula (Ve) with an oxidizing agent under the respective conditions.

The solvent which may be used in the above oxidation may be any solvent inert to the reaction, and includes, for example, aromatic hydrocarbons such as benzene, toleune, xylene and the like; halogenated hydrocarbons such as methylene chloride, chloroform, dichloroethane and the like; ethers such as diethyl ether, tetrahydrofuran, dioxane and the like; fatty acids such as formic acid, acetic acid and the like; water; etc. These solvents may be used in admixture of two or more. The oxidizing agent includes, for example, organic peracids such as performic acid, peracetic acid, perbenzoic acid, m-chloroperbenzoic acid and the like; hydrogen peroxide; periodic acid; sodium meta-periodate; potassium meta-periodate; potassium permanganate; ozone; etc.

The oxidizing agent which is particulary preferred to obtain the compound of the formula (IIg) or the compounds of the formulas (Ig) and (Vg) or salts thereof (sulfoxides) includes organic peracids, sodium metaperiodate, potassium meta-periodate and the like, and the amount of the oxidizing agent used is 1.0 to 1.2 moles per mole of the compound of the formula (IIe) or the compound of the formula (Ie) or (Ve) or a salt thereof.

The oxidizing agent which is particularly preferred to obtain the compound of the formula (IIh) or the compounds of the formulas (Ih) and (Vh) or salts thereof (sulfone) includes organic peracids, hydrogen peroxide and the like, and the amount of the oxidizing agent used is 2.0 to 2.5 moles per mole of the compound of the formula (IIe) or the compound of the formula (Ie) or (Ve) or a salt thereof. The compound of the formula (IIg) or the compound of the formula (Ig) or (Vg) or a salt thereof can be, if necessary, further oxidized into sulfones. These reactions may be effected usually at 0° to 100° C., preferably 0° to 30° C., for 5 minutes to 30 hours.

(9) The compound of the formula (Vf) or a salt thereof can be obtained by reacting the compound of the formula (Vb) or (Vd) or a salt thereof with an amine of the formula (IV) or a salt thereof in the presence or absence of an acid-binding agent, and also the compound of the formula (IIf) or a salt thereof can be obtained by reacting the compound of the formula (IIb) or (IId) with an amine of the formula (IV) or a salt thereof in the presence or absence of an acid-binding agent.

The solvent which may be used in the reaction may be any solvent inert to the reaction, and includes, for example, aromatic hydrocarbons such as benzene, toluene, xylene and the like; alcohols such as methanol, ethanol, n-propyl alcohol, isopropyl alcohol, n-butyl alcohol, isobutyl alcohol, tert.-butyl alcohol and the like; ethers such as dioxane, tetrahydrofuran, anisole, diethylene glycol diethyl ether and the like; ketones such as acetone, methyl ethyl ketone and the like; nitroalkanes such as nitromethane, nitroethane and the like; esters such as methyl acetate, ethyl acetate and the like; nitriles such as acetonitrile and the like; halogenated hydrocarbons such as methylene chloride, chloroform, dichloroethane and the like; amides such as N,N-dimethylformamide, N,N-dimethylacetamide and the like; sulfoxides such as dimethylsulfoxide and the like; etc. These solvents may be used in admixture of two or more. Also, the acid-binding agent includes specifically the same acid-binding agents as used in the above-mentioned sulfonylation.

The amount of the amine of the formula (IV) or a salt thereof is preferably 2.0 to 5.0 moles per mole of the compound of the formula (Vb) or a salt thereof, the compound of the formula (Vd) or a salt thereof, the compound of the formula (IIb) or the compound of the formula (IId) when the acid-binding agent is not used, and it can be reduced by appropriately using the acid-binding agent.

The above reactions may be effected usually at 0° to 150° C., preferably at 0° to 100° C., for 5 minutes to 30 hours.

(10) The compounds of the formulas (IIa), (IIb), (IIc), (IId), (IIe), (IIf), (IIg), (IIh), (IIi), and (IIj) or salts thereof [namely, the compounds of the formula (II) or salts thereof] can be obtained from the compounds of the formulas (Va), (Vb), (Vc), (Vd), (Ve), (Vf), (Vg), (Vh), (Vi) and (Vj) or salts thereof [namely, the compounds of the formula (V1) or salts thereof] in the following manners:

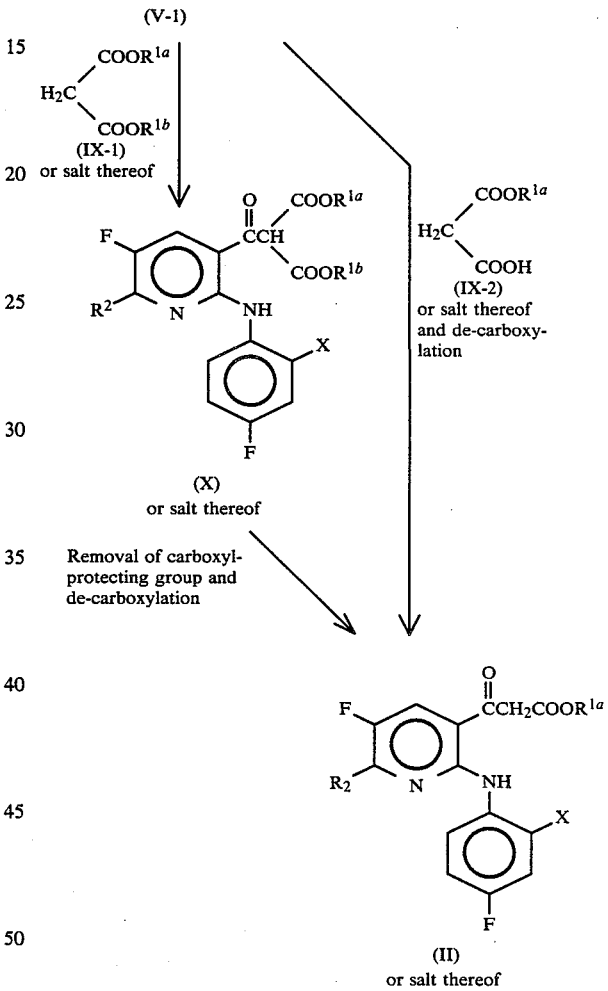

In the above formulas, $R^{1a}$, $R^2$ and X have the same meanings as defined above and $R^{1b}$ represents a carboxyl-protecting group including the same examples as those of $R^{1a}$ and may be the same as or different from $R^{1a}$.

The reactive derivative in the carboxyl group of the compound of the formula (V-1) includes, for example, acid halides such as acid chloride, acid bromide and the like; acid anhydrides, mixed acid anhydrides with monoethyl carbonate or the like; active esters such as dinitrophenyl ester, cyanomethyl ester, succinimido-ester and the like; active acid amides with imidazole or the like; etc.

The salts of the compounds of the formulas (IX-1) and (IX2) include, for example, salts with alkali metals such as lithium, potassium, sodium and the like; salts with alkaline earth metals such as magnesium and the like; salts with magnesium ethoxide; etc.

Also, the salts of the compound of the formula (X) include the same salts as mentioned as salts of the compound of the formula (I) and the like.

The compound of the formula (II) or (X) or a salt thereof can be produced by reacting a reactive derivative in the carboxyl group of the compound of the formula (V-1) with a compound of the formula (IX-2) or a salt thereof or a compound of the formula (IX-1) or a salt thereof, respectively, in an appropriate solvent. The solvent used may be any solvent inert to the reaction, and includes, for example, alcohols such as methanol, ethanol, isopropyl alcohol and the like; aromatic hydrocarbons such as benzene, toluene and the like; halogenated hydrocarbons such as methylene chloride, chloroform, dichloroethane and the like; ethers such as diethyl ether, tetrahydrofuran, dioxane and the like; nitriles such as acetonitrile and the like; amides such as N,N-dimethylformamide, N,N-dimethylacetamide and the like; etc. Aslo, the amount of the compound of the formula (IX-1) or (IX-2) or a salt thereof used is at least equimolar to, preferably 1.0 to 2.5 moles per mole of, the reactive derivative in the carboxyl group of the compound of the formula (V-1). The reaction may be effected usually at $-50°$ to $100°$ C., preferably at $-20°$ to $70°$ C., for 5 minutes to 30 hours.

In order to convert the compound of the formula (X) or a salt thereof into a compound of the formula (II) or a salt thereof, the compound of the formula (X) or a salt thereof may be subjected to removal of the carboxyl-protecting group of $R^1$ and de-carboxylation using trifluoroacetic acid in anisole or p-toluenesulfonic acid in a hydrous solvent.

(11) Ring-closure

In order to obtain the compounds of the formulas (Ia), (Ib), (Ic), (Id), (Ie), (If), (Ig), (Ih), (Ii), and (Ij) or salts thereof [namely, the compounds of the formula (I-4) or salts thereof] from the compounds of the formulas (IIa) (IIb), (IIc), (IId), (IIe), (IIf), (IIg), (IIh), (IIi) and (IIj) or salts thereof [namely, the compounds of the formula (II) or salts thereof], respectively, the compounds of the formula (II) or salts thereof may be reacted with acetals of N,N-di-substituted formamide of the formula (III) in the presence or absence of a solvent.

The solvent which may be used in the reaction may be any solvent inert to the reaction, and includes, for example, aromatic hydrocarbons such as benzene, toluene, xylene and the like; halogenated hydrocarbons such as methylene chloride, chlorform, dichloroethane and the like; ethers such as dioxane, tetrahydrofuran, diethylene glycol dimethyl ether and the like; esters such as methyl acetate, ethyl acetate and the like; ketones such as acetone, methyl ethyl ketone and the like; nitriles such as acetonitrile and the like; alcohols such as methanol, ethanol and the like; amides such as N,N-dimethylformamide, N,N-dimethylacetamide and the like; sulfoxides such as dimethylsulfoxide and the like; pyridine; etc., and these solvents may be used in admixture of two or more.

The amount of the acetal of the N,N-di-substituted formamide of the formula (III) used is at least equimolar to the compound of the formula (II) or a salt thereof, and it may be used in excess to serve as a solvent. Also, the reaction may be allowed to proceed smoothly by adding an acid anhydride such as acetic anhydride or the like. In this case, the amount of an acid anhydride added is preferably at least equimolar to, particularly preferably 1.0 to 5.0 moles per mole of, the compound of the formula (II) or a salt thereof. The reaction is usually completed in 5 minutes to 30 hours at a temperature of $0°$ to $150°$ C. Also, the acetal of the N,N-di-substituted formamide of the formula (III) may be prepared in the reaction system. In this case, the intermediate compound of the formula (XI) or a salt thereof is formed during the reaction:

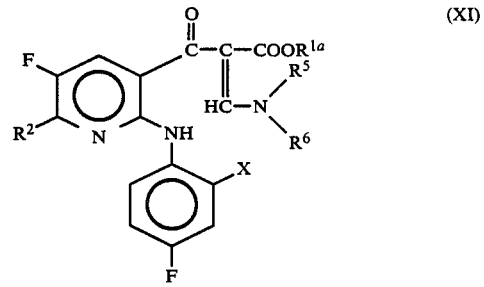

wherein $R^{1a}$, $R^2$, $R^5$, $R^6$ and X have the same meanings as defined above. The above intermediate compound can be isolated according to the conventional method; however, it may be converted to the compound of the formula (I) or a salt thereof without the isolation of the above intermediate. When the intermediate compound of the formula (XI) or a salt thereof is isolated, this may be subjected to ring-closure in the presence or absence of an acid to obtain the compound of the formula (I) or a salt thereof. The solvent used in this ring-closure may be any solvent inert to the reaction, and includes, the same as the solvents used in the above-mentioned reaction; fatty acids such as formic acid, acetic acid and the like; water; etc. These may be used in admixture of two or more. The optionally used acid includes, for example, mineral acids such as hydrochloric acid, hydrobromic acid, sulfuric acid and the like; organic carboxylic acids such as oxalic acid, trifluoroacetic acid and the like; sulfonic acids such as methanesulfonic acid, p-toluenesulfonic acid, naphthalenesulfonic acid and the like; etc., and these may be used usually in an amount at least equimolar to the compound of the formula (XI). Said reaction is effected usually at $0°$ to $150°$ C. for 5 minutes to 30 hours.

Moreover, the compound of the formula (I) or a salt thereof can also be produced by reacting a trialkyl orthoforate in place of the acetal of the N,N-di-substituted formamide in the presence or absence of acetic anhydride. The reaction is effected in the presence or absence of a solvent, and the solvent may be any solvent inert to the reaction, and includes, for example, aromatic hydrocarbons such as benzene, toluene, xylene and the like; ethers such as dioxane, tetrahydrofuran, diethylene glycol dimethyl ether, dimethyl Cellosolve and the like; halogenated hydrocarbons such as methylene chloride, chloroform, dichloroethane and the like; alcohols such as methanol, ethanol and the like; esters such as methyl acetate, ethyl acetate and the like; amides such as N,N-dimethylformamide, N,N-dimethylacetamide and the like; sulfoxides such as dimethylsilfoxide and the like; etc. These may be used in admixture of two or more. Also, the trialkyl orthoformates include trimethyl orthoformate, triethyl orthoformate and the like, and these may be used as the solvent. The amount of the orthoformate used is preferably at least equimolar to the compound of the formula (II) or a salt thereof. The reaction may be effected usually at 0° to 150° C., preferably at 15° to 110° C., for 5 minutes to 30 hours.

(12) Substitution with an amine

In order to produce the compounds of the formula (I-1) or salts thereof from the compounds of the formulas (Id), (Ie), (Ig), (Ih), (Ii) and (Ij) or the salts thereof [namely, the compounds of the formula (I-2) or salts thereof], the compounds of the formulas (I-2) or salts thereof may be reacted with an amine of the formula (IV) or a salt thereof in the presence or absence of an acid-binding agent. The solvent which may be used in the reaction may be any solvent inert to the reaction, and includes for example, alcohols such as methanol, ethanol, n-propyl alchol, isopropyl alcohol, n-butyl alcohol, isobutyl alcohol, tert.-butyl alcohol and the like; ethers such as dioxane, tetrahydrofuran, anisole, diethylene glycol diethyl ether and the like; ketones such as acetone, methyl ethyl ketone and the like; nitroalkanes such as nitromethane, nitroethane and the like; esters such as methyl acetate, ethyl acetate and the like; nitriles such as acetonitrile and the like; aromatic hydrocarbons such as benzene, toluene, xylene and the like; halgenated hydrocarbons such as methylene chloride, chloroform, dichloroethane and the like; amides such as N,N-dimethylformamide, N,N-dimethylacetamide and the like; sulfoxides such as dimethylsulfoxide and the like; etc. These may be used in admixture of two or more.

Also, the acid-binding agent includes, for example, organic or inorganic bases such as triethylamine, diisopropylamine, DBU, pyridine, potassium tert.-butoxide, potassium carbonate, sodium carbonate, sodium hydride and the like.

The amount of the amine of the formula (IV) or a salt thereof used is preferably 2.0 to 5.0 moles per mole of the compounds of the formula (I-2) or salts thereof when the acid-binding agent is not used, and it can be reduced by appropriately using the acid-binding agent.

The reaction may be effected usually at 0° to 150° C., preferably at 0° to 100° C., for 5 minutes to 30 hours.

In the above reaction, in the case of the compound of the formula (Id) or a salt thereof, the group of the formula $R^{10}SO_3$— is preferably a bulky alkanesulfonyloxy or arenesulfonyloxy group, particularly preferably an arenesulfonyloxy group in which at least one carbon atom adjacent to the carbon atom to which the oxysulfonyl group is attached is substituted by the above-mentioned substituent.

The compound obtained in each of the above-mentioned steps may be optionally subjected to removal of protecting group in a known manner to obtain the corresponding free carboxylic acid. Further, the free carboxylic acid may optionally be subjected to salt-forming reaction or esterification in a manner known per se to obtain the corresponding salt or ester.

The compounds obtained by the above-mentioned reactions may be isolated or separated by a conventional method, or may be used in the subsequent reactions without isolation or separation.

The process of this invention is very advantageous in industry in that the compound of the formula (I-1) or a salt thereof can be obtained without via a 2,6-dichloro-5-fluoropyridine derivative which is an intermediate in the processes disclosed in the above-mentioned Program and Abstract of the 24th I.C.A.A.C. and Japanese Patent Application Kokai (Laid-Open) No. 228,479/85 (said derivative causes a medical injury such as a rash or the like).

Antibacterial activities of typical compounds obtained by the process of this invention are shown below.

TEST METHOD

According to the standard method of Japan Society of Chemotherapy [CHEMOTHERAPY, 29(1), 76–79 (1981)], a bacterial solution obtained by culturing in Heart Infusion broth (manufactured by Eiken Kagaku) at 37° C. for 20 hours was inoculated onto a Heart Infusion agar containing a drug and cultured at 37° C. for 20 hours, after which the growth of the bacteria was observed to determine the minimum concentration at which the growth of the bacetria was inhibited as MIC (μg/ml). The amount of the inculated baceteria was $10^4$ cells/plate ($10^6$ cells/ml). The MIC values of the following test compounds are as shown in Table 1.

TABLE 1

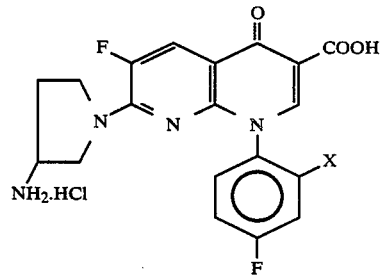

| Bacteria | F | H |
| --- | --- | --- |
| St. aureus FDA209P | ≦0.05 | ≦0.05 |
| St. equidermidis IID886 | ≦0.05 | 0.1 |
| St. aureus F-137* | ≦0.05 | 0.1 |
| E. coli NIHJ | ≦0.05 | ≦0.05 |
| E. coli TK-111 | ≦0.05 | ≦0.05 |
| E. coli GN5482** | ≦0.05 | ≦0.05 |
| Ps. aeruginosa S-68 | 0.2 | 0.2 |
| Aci. anitratus A-6 | ≦0.05 | ≦0.05 |
| Ps. aeruginosa IF03445 | 0.2 | 0.2 |
| Ps. aeruginosa GN918** | 0.1 | 0.1 |

*penicillinase-producing bacteria
**cephalosporinase-producing bacteria

When the compound of the formula (I-1) or a salt thereof is used as a drug or medicine, it is appropriately combined with carriers which are used in conventional pharmaceutical preparations, and is prepared into tablets, capsules, powders, syrups, granules, suppositories, ointments, injections and the like in a conventional manner. The administration routes, dosage and number of administrations can be appropriately varied depending upon the symptoms of patients, and it may be usually administered orally or parenterally (for example, by injection, drip, administration to rectum) to an adult in an amount of 0.1 to 100 mg/kg/day in one to several portions.

This invention will be explained below referring to Examples, which are not by way of limitation but by way of illustration.

Symbols used in the Examples have the following meanings:

Me: methyl group, Et: ethyl group,
n-Pr: n-propyl group, i-Pr: isopropyl group,
Ac: acetyl group

EXAMPLE 1

(1) In 300 ml of ethyl acetate were suspended 50 g of ethyl β-imino-β-phenoxypropionate hydrochloride and 27.8 g of 2,4-difluoroaniline, and the resulting suspension was subjected to reaction under reflux for 2 hours. The deposited crystals were separated by filtration and washed with two 200-ml portions of ethyl acetate to obtain 47 g (yield 82.2%) of ethyl N-(2,4-difluorophenyl)amidinoacetate hydrochloride having a melting point of 196°–197° C.

IR (KBr) cm$^{-1}$:$\nu_{C=O}$1730.

NMR (DMSO-d$_6$) δ values: 1.26 (3H, t, J=7 Hz), 4.07 (2H, s), 4.19 (2H, q, J=7 Hz), 7.02–7.78 (3H, m), 9.11 (1H, bs), 10.26 (1H, bs), 12.28 (1H, bs).

In the same manner as above, the following compounds were obtained:

Methyl N-(2,4-difluorophenyl)amidinoacetate hydrochloride
   Melting point: 192°–193° C.
   IR (KBr) cm$^{-1}$:$\nu_{C=O}$1735.
   NMR (DMSO-d$_6$) δ values: 3.74 (3H, s), 4.09 (2H, s), 6.91–7.73 (3H, m), 9.15 (1H, bs), 10.31 (1H, bs), 12.29 (1H, bs).

Methyl N-(4-fluorophenyl)amidinoacetate hydrochloride
   Melting point: 134°–135° C.
   IR (KBr) cm$^{-1}$:$\nu_{C=O}$1730.
   NMR (DMSO-d$_6$) δ values: 3.74 (3H, s), 4.05 (2H, s), 7.01–7.59 (4H, m), 8.96 (1H, bs), 10.06 (1H, bs), 12.26 (1H, bs).

(2) In a mixture of 92 ml of water and 92 ml of methylene chloride was dissolved 23.0 g of methyl N-(2,4-difluorophenyl)amidinoacetate hydrochloride, and the pH of the solution was adjusted to 13 with 2N aqueous sodium hydroxide solution. Subsequently, the organic layer was separated, washed successively with 50 ml of water and 50 ml of saturated aqueous sodium chloride solution and dried over anhydrous magnesium sulfate. To this solution was added 27.1 g of the sodium salt of ethyl α-formyl-α-fluoroacetate at room temperature, and the resulting mixture was subjected to reaction under reflux for 4 hours, after which the solvent was removed by distillation under reduced pressure. To the residue thus obtained were added 92 ml of water and 46 ml of ethyl acetate, and the crystals thus deposited were collected by filtration. The crystals thus obtained were suspended in 184 ml of water and the pH of the suspension was adjusted to 1.0 with 6N hydrochloric acid, and to the crystalline material thus obtained were added 46 ml of water and 46 ml of isopropyl alcohol, after which the crystals were collected by filtration to obtain 15.0 g (yield 57.9%) of methyl 2-(2,4-difluorophenylamino)-5-fluoro-6-hydroxynicotinate having a melting point of 222°–223° C.

Melting point: 222°–223° C. (recrystallized from ethyl acetate).

IR (KBr) cm$^{-1}$:$\nu_{C=O}$1700.

NMR (TFA-d$_1$) δ values: 4.06 (3H, s), 6.71–7.65 (3H, m), 8.12 (1H, d, J=11 Hz).

In the same manner as above, the following compounds were obtained:

Ethyl 2-(2,4-difluorophenylamino)-5-fluoro-6-hydroxynicotinate
   Melting point: 177°–178° C. (recrystallized from ethyl acetate).
   IR (KBr) cm$^{-1}$ $\nu_{C=O}$1700.

NMR (TFA-d$_1$) δ values: 1.52 (3H, t, J=7 Hz), 4.50 (2H, q, J=7 Hz), 6.80–7.65 (3H, m), 8.15 (1H, d, J=11 Hz).

Methyl 5-fluoro-2-(4-fluorophenylamino)-6-hydroxynicotinate
   Melting point: 227°–228° C. (recrystallized from ethyl acetate).
   IR (KBr) cm$^{-1}$:$\nu_{C=O}$1690.
   NMR (TFA-d$_1$) δ values: 4.05 (3H, s), 6.89–7.53 (4H, m), 8.11 (1H, d, J=11 Hz).

(3) In a mixture of 5 ml of water and 5 ml of methylene chloride was dissolved 500 mg of methyl N-(2,4-difluorophenyl)amidino acetate hydrochloride, and the pH of the resulting solution was adjusted to 13.0 with 2N aqueous sodium hydroxide solution. The organic layer was separated and washed successively with 3 ml of water and 3 ml of saturated aqueous sodium chloride solution, and then dried over anhydrous magnesium sulfate. To this solution was added 820 mg of ethyl 3-(4-methylbenzenesulfonyloxy)-2-fluoroacrylate, and then, 120 mg of sodium methoxide (purity: 92.3%) and 5 ml of methanol were added thereto at room temperature, after which the resulting mixture was subjected to reaction at the same temperature for 24 hours. The solvent was then removed by distillation under reduced pressure, and to the residue thus obtained were added 10 ml of water and 2 ml of ethyl acetate. The pH of the resulting solution was adjusted to 1.0 with 6N hydrochloric acid, and the crystals thus deposited were collected by filtration and washed successively with 2 ml of water and 2 ml of isopropyl alcohol to obtain 370 mg (yield 65.7%) of methyl 2-(2,4-difluorophenylamino)-5-fluoro-6-hydroxynicotinate. The physical properties of this compound were identical with those of the compound obtained in (2) above.

(4) The same procedure as in (3) above was repeated, except that one of the 3-substituted-2-fluoroacrylates shown in Table 2 was substituted for the ethyl 3-(4-methylbenzenesulfonyloxy)-2-fluoroacrylate to obtain the results shown in Table 2.

TABLE 2

$$F\text{-}\langle\text{Ph}\rangle\text{-NHCCH}_2\text{COOMe} + \underset{Z}{\overset{H}{\diagdown}}C=C\underset{F}{\overset{\diagup}{}}\text{-COOEt} \xrightarrow{\text{NaOMe}}$$

(with F substituent on phenyl, =NH on C)

Product: methyl 5-fluoro-6-hydroxy-2-(2,4-difluorophenylamino)nicotinate structure

| Compound Z | Yield (%) |
|---|---|
| MeSO$_3$— | 41.7 |
| (PhO)$_2$PO— | 50.7 |

TABLE 2-continued

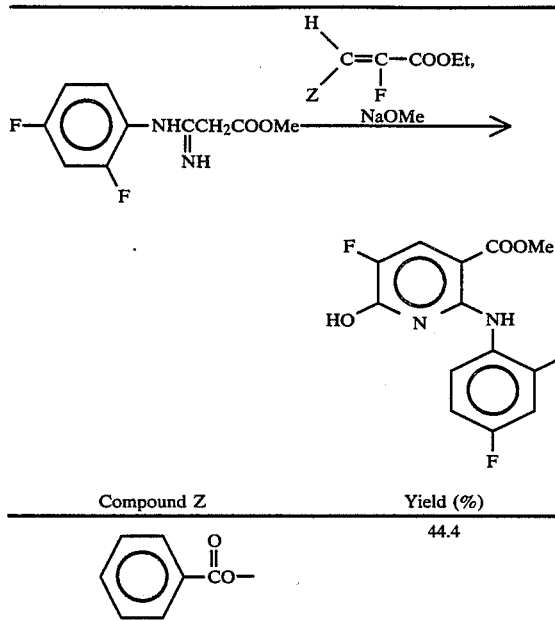

| Compound Z | Yield (%) |
|---|---|
| (benzoyl: C₆H₅-CO-) | 44.4 |

The physical properties of the compounds obtained in the respective cases were identical with those of the compound obtained in (2) above.

EXAMPLE 2

In 6 ml of tetrahydrofuran was dissolved 200 mg of methyl 2-(2,4-difluorophenylamino)-5-fluoro-6-hydroxynicotinate, and a solution of about 40 mg of diazomethane in diethyl ether was added to the resulting solution with ice-cooling, after which the resulting mixture was subjected to reaction at room temperature for 30 minutes. Subsequently, acetic acid was added until foaming was not caused in the reaction mixture, after which the solvent was removed by distillation under reduced pressure. The crystals thus obtained were washed with 6 ml of isopropyl alcohol to obtain 150 mg (yield 71.6%) of methyl 2-(2,4-difluorophenylamino)-5-fluoro-6-methoxynicotinate having a melting point of 160°–161° C.

Melting point: 160.5°–161.5° C. (recrystallized from ethyl acetate).

IR (KBr) cm$^{-1}$:$\nu_{C=O}$1690.

NMR (CDCl$_3$) δ values: 3.89 (3H, s), 3.98 (3H, s), 6.57–7.08 (2H, m), 7.81 (1H, d, J=11 Hz), 8.10–8.97 (1H, m), 10.24 (1H, bs).

EXAMPLE 3

In 5 ml of N,N-dimethylformamide was dissolved 200 mg of methyl 2-(2,4-difluorophenylamino)-5-fluoro-6-hydroxynicotinate, and to the resulting solution were added 110 mg of potassium carbonate and 93 mg of dimethyl sulfate at room temperature, after which the resulting mixture was subjected to reaction at the same temperature for 2 hours. Subsequently, 20 ml of water and 20 ml of ethyl acetate were added to the reaction mixture, and the organic layer was then separated, washed successively with 10 ml of water and 10 ml of saturated aqueous sodium chloride solution, and thereafter dried over anhydrous magnesium sulfate. The solvent was removed by distillation under reduced pressure, and to the crystalline material thus obtained was added 5 ml of isopropyl alcohol, after which crystals were collected by filtration to obtain 180 mg (yield 86.0%) of methyl 2-(2,4-difluorophenylamino)-5-fluoro-6-methoxynicotinate. The physical properties of this compound were identical with those of the compound obtained in Example 2.

EXAMPLE 4

In 5 ml of N,N-dimethylformamide was dissolved 200 mg of methyl 2-(2,4-diflurophenylamino)-5-fluoro-6-hydroxynicotinate, and thereto were added 110 mg of potassium carbonate and 0.11 g of methyl iodide at room temperature, after which the resulting mixture was subjected to reaction at the same temperature for 1 hour. To the reaction mixture were added 20 ml of water and 20 ml of ethyl acetate, and the organic layer was separated, washed successively with 10 ml of water and 10 ml of saturated aqueous sodium chloride solution, and then dried over anhydrous magnesium sulfate. The solvent was removed by distillation under reduced pressure and then to the crystalline material thus obtained was added 5 ml of isopropyl alcohol, after which crystals were collected by filtration to obtain 190 mg (yield 90.7%) of methyl 2-(2,4-difluorophenylamino)-5-fluoro-6-methoxynicotinate. The physical properties of this compound were identical with those of the compound obtained in Example 2.

EXAMPLE 5

A mixture of 9.5 g of methyl 2-(2,4-difluorophenylamino)-5-fluoro-6-hydroxynicotinate, 26.5 g of phosphorus pentachloride and 46.9 g of phosphorus oxychloride was subjected to reaction at 70°–80° C. for 4 hours. Subsequently, the reaction mixture was gradually added to 285 ml of water, and the crystals thus deposited were collected by filtration and then washed with 57 ml of water. The crystals thus obtained were purified by a column chromatography [Wako Silica Gel C-200, eluant: toluene] to obtain 3.5 g (yield 34.7%) of methyl 6-chloro-2-(2,4-difluorophenylamino)-5fluoronicotinate having a melting point of 137°–139° C.

Melting point: 139.5°–140.5° C. (recrystallized from diisopropyl ether).

IR (KBr) cm$^{-1}$:$\nu_{C=O}$1695.

NMR (CDCl$_3$) δ values: 3.93 (3H, s), 6.61–7.06 (2H, m), 7.94 (1H, d, J=9 Hz), 8.15–8.57 (1H, m), 10.13 (1H, bs).

EXAMPLE 6

In 10 ml of methylene chloride was suspended 500 mg of methyl 2-(2,4-difluorophenylamino)5-fluoro-6-hydroxynicotinate, and to the resulting suspension were added 440 mg, of 2,4,6-trimethylbenzenesulfonyl chloride and 220 mg of triethylamine, after which the resulting mixture was subjected to reaction at room temperature for 3 hours. To this solution was added 15 ml of water, and the organic layer was separated, washed with 15 ml of water, and then dried over anhydrous magnesium sulfate. The solvent was removed by distillation under reduced pressure, and to the crystalline material thus obtained was added 15 ml of diethyl ether, after which crystals were collected by filtration to obtain 660 mg (yield 81.9%) of methyl 2-(2,4-difluorophenylamino)-5-fluoro-6-(2,4,6-trimethylbenzenesulfonyloxy)nicotinate having a melting point of 153°–155° C.

Melting point: 155°–156° C. (recrystallized from ethyl acetate).

IR (KBr) cm$^{-1}$:$\nu_{C=O}$1700.

NMR (CDCl$_3$) δ values: 2.33 (3H, s), 2.59 (6H, s), 3.92 (3H, s), 6.32–6.84 (2H, m), 6.92 (2H, s), 7.35–7.94 (1H, m), 8.05 (1H, d, J=9 Hz), 10.17 (1H, bs).

In the same manner as above, the following compounds were obtained:

Methyl 2-(2,4-difluorophenylamino)-5-fluoro-6-methanesulfonyloxynicotinate

Melting point: 120°–121° C. (recrystallized from ethyl acetate).

IR (KBr) cm$^{-1}$:$\nu_{C=O}$1690.

| NMR (CDCl$_3$) δ values: | | |
|---|---|---|
| 3.30 (3H, s), 3.94 (3H, s), 6.60–7.15 (2H, m), | | |
| 7.73–8.33 (m) } (2H), | | 10.00 (1H, bs) |
| 8.07 (d, J=9Hz) } | | |

Ethyl 2-(2,4-difluorophenylamino)-5-fluoro-6-(2,4,6-triisopropylbenzenesulfonyloxy)nicotinate Melting point: 147°–148° C. (recrystallized from ethyl acetate)

MR (KBr) cm$^{-1}$:$\nu_{C=O}$1700.

| NMR (CDCl$_3$) δ values: | |
|---|---|
| 1.21 (12H, d, J=7Hz), 1.28 (6H, d, J=7Hz), | |
| 1.40 (3H, t, J=7Hz), 2.55–3.30 (1H, m), | |
| 3.70–4.60 (m) } (4H), | 6.20–7.30 (m) } (4H), |
| 4.73 (q, J=7Hz) } | 7.20 (s) } |
| 7.50–8.30 (m) } (2H), | 10.33 (1H, bs) |
| 8.10 (d, J=9Hz) } | |

EXAMPLE 7

In 7 ml of N,N-dimethylformamide was suspended 700 mg of methyl 6-chloro-2-(2,4-difluorophenylamino)-5-fluoronicotinate, and to the resulting suspension were added 340 mg of triethylamine and 210 mg of ethanethiol at room temperature, after which the resulting mixture was subjected to reaction at 50° C. for 4 hours. Subsequently, 40 ml of ethyl acetate and 30 ml of water were added to the reaction mixture, and the pH of the mixture was adjusted to 2 with 2N hydrochloric acid. The organic layer was separated, washed successively with 20 ml of water and 20 ml of saturated aqueous sodium chloride solution, and then dried over anhydrous magnesium sulfate. The solvent was removed by distillation under reduced pressure, and to the crystalline material thus obtained was added 10 ml of hexane, after which crystals were collected by filtration to obtain 620 mg (yield 81.9%) of methyl 6-ethylthio-2-(2,4-difluorophenylamino)-5-fluoronicotinate having a melting point of 113°–114° C.

Melting point: 113.5°–114° C. (recrystillized from diisopropyl ether)

IR (KBr) cm$^{-1}$:$\nu_{C=O}$1680.

NMR (CDCl$_3$) δ values: 1.29 (3H, t, J=7 Hz), 3.07 (2H, q, J=7 Hz), 3.90 (3H, s), 6.50–7.20 (2H, m), 7.66 (1H, d, J=10 Hz), 7.80–8.50 (1H, m), 10.00 (1H, bs).

In the same manner as above, methyl 2-(2,4-difluorophenylamino)-5-fluoro-6-phenylthionicotinate was obtained.

Melting point: 128°–128.5° C. (recrystallized from diisopropyl ether).

IR (KBr) cm$^{-1}$:$\nu_{C=O}$1685.

| NMR (CDCl$_3$) δ values: | |
|---|---|
| 3.90 (3H, s), 6.0–8.0(m) } | |
| 7.77 (d, J=10Hz) } | (9H), |
| 10.25 (1H, bs) | |

EXAMPLE 8

In 10 ml of N,N-dimethylformamide was suspended 1.00 g of methyl 6-chloro-2-(2,4-difluorophenylamino)-5-fluoronicotinate, and to the resulting suspension were added 750 mg of 3-aminopyrrolidine dihydrochloride, and 1.44 g of triethylamine, after which the resulting mixture was subjected to reaction at 70° C. for 30 minutes. Subsequently, to the reaction mixture were added 50 ml of chloroform and 50 ml of water, and the organic layer was separated, washed successively with 25 ml of water and 25 ml of saturated aqueous sodium chloride solution, and then dried over anhydrous magnesium sulfate. The solvent was removed by distillation under reduced pressure, and to the crystalline material thus obtained was added 5 ml of diethyl ether, after which crystals were collected by filtration to obtain 1.10 g (yield 95.1%) of methyl 6-(3-amino-1-pyrrolidinyl)-2-(2,4-difluorophenylamino)-5-fluoronicotinate having a melting point of 139°–140° C.

IR (KBr) cm$^{-1}$:$\nu_{C=O}$1670.

| NMR (CDCl$_3$) δ values: | |
|---|---|
| 1.58–2.27 (2H, m), 3.17–4.10 (m) } | (8H) |
| 3.84 (s) } | |
| 6.57–7.12 (2H, m), 7.58 (1H, d, J=14Hz), | |
| 8.10–8.62 (1H, m), 10.32 (1H, bs) | |

In the same manner as above, methyl 6-(4-acetyl-1-piperazinyl)-2-(2,4-difluorophenylamino)-5-fluoronicotinate was obtained.

Melting point: 172°–173° C. (recrystallized from ethyl acetate).

IR (KBr) cm$^{-1}$:$\nu_{C=O}$1680, 1650.

| NMR (CDCl$_3$) δ values: | |
|---|---|
| 2.13 (3H, s), 3.32–4.12 (m) } | (11H), |
| 3.85 (s) } | |
| 6.57–7.07 (2H, m), 7.68 (1H, d, J=13Hz), | |
| 7.77–8.18 (1H, m), 10.05 (1H, bs) | |

EXAMPLE 9

In 6.5 ml of chloroform was dissolved 650 mg of methyl 6-(3-amino-1-pyrrolidinyl)-2-(2,4-difluorophenylamino)-5-fluoronicotinate, and 190 mg of acetic anhydride was added to the resulting solution, after which the resulting mixture was subjected to reaction at room temperature for 10 minutes. The solvent was then removed by distillation under reduced pressure. To the crystalline material thus obtained was added 2 ml of diethyl ether, after which crystals were collected by filtration to obtain 720 mg (yield 99.4%) of methyl 6-(3-acetylamino-1-pyrrolidinyl)-2-(2,4-difluorophenylamino)-5-fluoronicotinate having a melting point of 199°–200° C.

Melting point: 202°–203° C. (recrystallized from ethyl acetate).

IR (KBr) cm$^{-1}$:$\nu_{C=O}$1675.

| NMR (CDCl$_3$-DMSO-d$_6$) δ values: |
| --- |
| 1.63–2.27 (m) ⎫ (5H),    3.38–4.62 (m) ⎫ (8H), |
| 1.91 (s) ⎭            3.82 (s) ⎭ |
| 6.63–7.17 (2H, m), 7.62 (1H, d, J=14Hz), |
| 7.83–8.60 (2H, m), 10.30 (1H, bs) |

EXAMPLE 10

In 3 ml of N,N-diemthylformamide was suspended 120 mg of 3-aminopyrrolidine dihydrochloride, and 250 mg of triethylamine was added to the resulting suspension, after which the resulting mixture was subjected to reaction at room temperature for 5 minutes. Thereafter, 300 mg of methyl 2-(2,4-difluorophenylamino)-5-fluoro-6-(2,4,6-trimethylbenzenesulfonyloxy)nicotinate was added to the reaction mixture, and the resulting mixture was subjected to reaction at room temperature for 1.5 hours. To the reaction mixture were added 10 ml of chloroform and 10 ml of water, and the organic layer was separated, washed successively with 10 ml of water and 10 ml of saturated aqueous sodium chloride solution, and then dried over anhydrous magnesium sulfate. Subsequently, 100 mg of acetic anhydride was added to the organic layer, and the resulting mixture was subjected to reaction at room temperature for 10 minutes, after which the solvent was removed by distllation under reduced pressure. To the crystalline material thus obtained was added 5 ml of diethyl ether, and crystals were collected by filtration to obtain 210 mg (yield 82.4%) of methyl 6-(3-acetylamino-1-pyrrolidinyl)-2-(2,4-difluorophenylamino)-5-fluoronicotinate. The physical properties of this compound were identical with those of the compound obtained in Example 9.

In the same manner as above, methyl 6-(4-acetyl-1-piperazinyl)-2-(2,4-difluorophenylamino)-5-fluoronicotinate was obtained.

The physical properties of this compound were identical with those of the compound obtained in Example 8.

EXAMPLE 11

In 39 ml of N,N-dimethylformamide was dissolved 3.89 g of methyl 2-(2,4-difluorophenylamino)-5-fluoro-6-(mesitylenesulfonyloxy)nicotinate, and to the resulting solution were added 1.34 g of thiophenol and 1.23 g of triethylamine, after which the resulting mixture was subjected to reaction at room temperature for 5 hours. Subsequently, 120 ml of ethyl acetate and 120 ml of water were added to the reaction mixture, and the pH of the mixture was adjusted to 2.0 with 2N hydrochloric acid. The organic layer was separated, washed successively with 80 ml of water and 80 ml of saturated aqueous sodium chloride solution, and then dried over anhydrous magnesium sulfate. The solvent was removed by distillation under reduced pressure, and to the crystalline material thus obtained was added 20 ml of n-hexane, after which the crystals thus deposited were collected by filtration to obtain 2.85 g (yield 90.2%) of methyl 2-(2,4-difluorophenylamino)-5-fluoro-6-phenylthionicotinate having a melting point of 126°–128° C. The physical properties of this compound were identical with those of the compound obtained in Example 7.

In the same manner as above, methyl 2-(2,4-difluorophenylamino)-6-ethylthio-5-fluoronicotinate was obtained. The physical properties of this compound were identical with those of the compound obtained in Example 7.

EXAMPLE 12

In 30 ml of methanol was suspended 3.00 g of methyl 2-(2,4-difluorophenylamino)-5-fluoro-6-hydroxynicotinate, and 16.1 ml of 2N aqueous sodium hydroxide solution was added thereto at room temperature, after which the resulting mixture was subjected to reaction under reflux for 4 hours. Subsequently, the reaction mixture was added to a mixture of 60 ml of ethyl acetate and 60 ml of water, and the aqueous layer was separated. The aqueous layer was adjusted to pH 1.0 with 6N hydrochloric acid, and the crystals thus deposited were collected by filtration, washed successively with 15 ml of water and 15 ml of isopropyl alcohol to obtain 2.68 g (yield 93.7%) of 2-(2,4-difluorophenylamino)-5-fluoro-6-hydroxynicotinate acid having a melting point of 213°–216° C.

Melting point: 215°–216° C. (recrystallized from acetoneethanol (1:1 by volume))

IR (KBr) cm$^{-1}$:$\nu_{C=O}$1700.

NMR (DMSO-d$_6$) δ values: 6.65–7.58 (2H, m), 7.86 (1H, d, J=11 Hz), 8.12–8.68 (1H, m), 10.49 (1H, bs).

In the same manner as above, 5-fluoro-2-(4-fluorophenylamino)-6-hydroxynicotinic acid was obtained.

Melting point: 216°–217° C. (recrystallized from acetonemethanol (1:1 by volume)).

IR (KBr) cm$^{-1}$:$\nu_{C=O}$1685 (sh).

NMR (DMSO-d$_6$) δ values: 6.84–7.94 (5H, m), 10.33 (1H, bs).

EXAMPLE 13

In 60 ml of tetrahydrofuran was dissolved 2.00 g of methyl 2-(2,4-difluorophenylamino)-5-fluoro6-methoxynicotinate, and 25.5 ml of 1N aqueous sodium hydroxide solution was added thereto at room temperature, after which the resulting mixture was subjected to reaction under reflux for 7 hours. Subsequently, the solvent was removed by distillation under reduced pressure, and to the residue thus obtained were added 100 ml of ethyl acetate and 100 ml of water, after which the pH of the resulting mixture was adjusted to 2.0 with 2N hydrochloric acid. The organic layer was washed successively with 50 ml of water and 50 ml of saturated aqueous sodium chloride solution, and dried over anhydrous magnesium sulfate. The solvent was removed by distillation under reduced pressure, and to the crystalline material thus obtained was added 10 ml of diethyl ether, after which crystals were collected by filtration to obtain 1.40 g (yield 73.3%) of 2-(2,4-difluorophenylamino)-5-fluoro-6-methoxynicotinic acid having a melting point of 237°–240° C.

Melting point: 239°–240° C. (recrystallized from acetone).

IR (KBr) cm$^{-1}$:$\nu_{C=O}$1665.

NMR (DMSO-d$_6$) δ values: 3.98 (3H, s), 6.76–7.84 (2H, m), 7.86 (1H, d, J=11 Hz), 8.10–8.60 (1H, bs).

In the same manner as above, the following compounds were obtained:
6-Chloro-2-(2,4-difluorophenylamino)-5-fluoronicotinic acid Melting point: 226°–228° C. (recrystallized from benzene)
IR (KBr) cm$^{-1}$:$\nu_{C=O}$1680.

NMR (acetone-d$_6$) δ values:

6.60–7.41 (2H, m), 7.90–8.50 (m)
8.10 (d, J=9Hz) } (2H),
10.30 (1H, bs), 10.64 (1H, bs)

2-(2,4-Difluorophenylamino)-5-fluoro-6-(2,4,6-trimethylbenzenesulfonyloxy)nicotinic acid
Melting point: 179°–180° C. (recrystallized from benzene)
IR (KBr) cm$^{-1}$:$\nu_{C=O}$1665.

NMR (acetone-d$_6$) δ values:

2.32 (3H, s), 2.55 (6H, s), 6.37–8.52 (m)
7.05 (s)
8.24 (d, J=9Hz) } (7H)
10.37 (1H, bs)

2-(2,4-Difluorophenylamino)-5-fluoro-6-(2,4,6-triisopropylbenzenesulfonyloxy)nicotinic acid
Melting point: 163.5°–164.5° C. (recrystallized from benzene).
IR (KBr) cm$^{-1}$ $\nu_{C=O}$1675.

NMR (CDCl$_3$/DMSO-d$_6$) δ values:

1.22 (12H, d, J=7Hz), 1.30 (6H, d, J=7Hz),
2.55–3.30 (1H, m), 3.70–4.40 (2H, m),
6.20–8.30 (m)
7.22 (s) } (6H), 9.66 (1H, bs),
8.18 (d, J=9Hz)
10.57 (1H, bs)

6-Ethylthio-2-(2,4-difluorophenylamino)-5-fluoronicotinic acid
Melting point: 209°–210° C. (recrystallized from benzene)
IR (KBr) cm$^{-1}$:$\nu_{C=O}$1665.

NMR (acetone-d$_6$) δ values:

1.30 (3H, t, J=7Hz), 3.14 (2H, q, J=7Hz),
6.70–7.50 (2H, m), 7.60–8.50 (m)
7.80 (d, J=9Hz) } (2H),
9.70 (1H, bs), 10.27 (1H, bs)

2-(2,4-Difluorophenylamino)-5-fluoro-6-phenylthionicotinic acid
Melting point: 264°–265° C. (recrystallized from ethyl acetate-ethanol (1:1 by volume)).
IR (KBr) cm$^{-1}$:$\nu_{C=O}$1660.
NMR (DMSO-d$_6$) δ values: 6.00–7.73 (8H, m), 7.85 (1H, d, J=10 Hz), 10.58 (1H, bs).

EXAMPLE 14

In a mixture of 30 ml of tetrahydrofuran, 10 ml of methanol and 4 ml of water was suspended 980 mg of methyl 6-(3-acetylamino-1-pyrrolidinyl)-2-(2,4-difluorophenylamino)-5-fluoronicotinate, and 5.3 ml of 1N aqueous sodium hydroxide solution was added thereto, after which the resulting mixture was subjected to reaction at 65° C. for 3 hours. Subsequently, the reaction mixture was added to a mixture of 50 ml of ethyl acetate and 50 ml of water, and the aqueous layer was separated, after which the pH thereof was adjusted to 2.0 with 1N hydrochloric aicd. The crystals thus deposited were collected by filtration and washed successively with 2 ml of water and 2 ml of ethanol to obtain 880 mg (yield 93.0%) of 6-(3-acetylamino-1-pyrrolidinyl)-2-(2,4-difluorophenylamino)-5-fluoronicotinic acid having a melting point of 232°–234° C.
Melting point: 233.5°–236° C. (recrystallized from acetonemethanol (1:1 by volume)).
IR (KBr) cm$^{-1}$:$\nu_{C=O}$1645.

NMR (TFA-d$_1$) δ values:

2.00–2.68 (m)
2.28 (s) } (5H), 3.62–5.03 (5H, m),
6.82–7.80 (3H, m), 8.27 (1H, d, J=13Hz)

In the same manner as above, 6-(4-acetyl-1-piperazinyl)-2-(2,4-difluorophenylamino)-5-fluoronicotinic acid was obtained.
Melting point: 243°–244° C. (recrystallized from ethyl acetate-ethanol (1:1 by volume)).
IR (KBr) cm$^{-1}$:$\nu_{C=O}$1670, 1635(sh).
NMR (TFA-d$_1$) δ values: 2.48 (3H, s), 3.47–4.40 (8H, m), 6.83–7.82 (3H, m), 8.47 (1H, d, J=13 Hz).

EXAMPLE 15

In 3.9 ml of methanol was suspended 130 mg of methyl 6-(4-acetyl-1-piperazinyl)-2-(2,4-difluorophenylamino)-5-fluoronicotinate, and 3.33 ml of 2N aqueous sodium hydroxide solution was added thereto, after which the resulting mixture was subjected to reaction under reflux for 2 hours. To the reaction mixture was added 2 ml of water, and the pH thereof was adjusted to 8.5 with 1N hydrochloric acid, after which the crystals thus deposited were collected by filtration and washed with 2 ml of water to obtain 110 mg (yield 98.2%) of 2-(2,4-difluorophenylamino)-5-fluoro-6-(1-piperazinyl)nicotinic acid having a melting point of 279°–281° C.
IR (KBr) cm$^{-1}$:$\nu_{C=O}$(1625 (sh).
NMR (TFA-d$_1$) δ values: 3.53–4.33 (8H, m), 6.87–7.77 (3H, m), 8.53 (1H, d, J=13 Hz).
In the same manner as above, 6-(3-amino-1-pyrrolidinyl)-2-(2,4-difluorophenylamino)-5-fluoronicotinic acid was obtained.
Melting point: 249°–250° C.
IR (KBr) cm$^{-1}$:$\nu_{C=O}$1630(sh).
NMR (TFA-d$_1$) δ values: 2.47–2.92 (2H, m), 3.72–4.23 (2H, m), 4.23–4.73 (3H, m), 6.95–7.77 (3H, m), 8.36 (1H, d, J=13 Hz).

EXAMPLE 16

In 150 ml of methylene chloride was suspended 5.00 g of 2-(2,4-difluorophenylamino)-5-fluoro-6-methoxynicotinic acid, and 5.98 g of thionyl chloride and 3 drops of N,N-dimethylformamide were added thereto, after which the resulting mixture was subjected to reaction under reflux for 2 hours. The solvent and the excessive thionyl chloride were removed by distillation under reduced pressure, and to the crystalline material thus obtained was added 10 ml of n-hexane, after which crystals were collected by filtration to obtain 4.87 g (yield 91.7%) of 2-(2,4-difluorophenylamino)-5-fluoro- 6-methoxynicotinoyl chloride having a melting point of 153°-154° C.

Melting point: 154°-155° C. (recrystallized from methylene chloride).

IR (KBr) cm$^{-1}$:$\nu_{C=O}$1680.

| NMR (CDCl$_3$) δ values: | |
|---|---|
| 3.98 (3H, s), 6.60-7.10 (2H, m), | |
| 7.70-8.30 (m) | 9.65 (1H, bs) (2H), |
| 8.06 (d, J=10Hz) | |

In the same manner as above, the compound shown in Table 3 were obtained.

TABLE 3

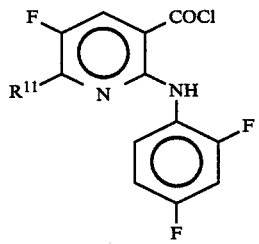

| Compound R$^{11}$ | m.p. (°C.) | IR (KBr) cm$^{-1}$: $\nu_{C=O}$ | NMR (*CDCl$_3$ / **DMSO—d$_6$) δ values: |
|---|---|---|---|
| Me—⟨Me,Me⟩—SO$_3$— | 136.5-138 (recrystallized from n-hexane) | 1705 | *2.34 (3H, s), 2.57 (6H, s), 6.40-7.10 (4H, m), 7.55-8.05 (1H, m), 8.28 (1H, d, J=9Hz), 9.55 (1H, bs) |
| i-Pr—⟨i-Pr,i-Pr⟩—SO$_3$— | 140-142 (recrystallized from diisopropyl ether) | 1700 | *1.23 (12H), d, J=7Hz), 1.30 (6H, d, J=7Hz), 2.60-3.35 (1H, m), 3.75-4.45 (2H, m), 6.40-7.40 (m), 7.22 (s) } (4H) 7.80-8.50 (m), 8.35 (d, J=9Hz) } (2H), 9.77 (1H, bs) |
| EtS— | 85-87 (recrystallizated from n-hexane) | 1685 | *1.23 (3H, t, J=7Hz), 3.00 (2H, q, J=7Hz), 6.60-7.30 (2H, m), 7.40-8.05 (m), 7.86 (d, J=10Hz) } (2H), 9.32 (1H, bs) |
| ⟨Ph⟩—S— | 179-181 (recrystallized from chloroform) | 1690 | **6.00-8.10 (m), 7.63 (s), 7.92 (d, J=10Hz) } (9H), 10.54 (1H, bs) | mixture was subjected to reaction at room temperature for 30 minutes. Subsequently, 5 ml of water was added to the reaction mixture, and the pH thereof was adjusted to 2.0 with 2N hydrochloric acid. The organic layer was separated, washed successively with 5 ml of water and 5 ml of saturated aqueous sodium chloride solution, and then dried over anhydrous magnesium sulfate. The solvent was removed by distillation under reduced pressure, and to the crystalline material thus obtained was added 2 ml of diisopropyl ether, after which crystals were collected by filtration to obtain 485 mg (yield 91.1%) of 1-[2-(2,4-difluorophenylamino)-5-fluoro-6-(mesitylenesulfonyloxy)nicotinoyl]imidazole having a melting point of 98°-101° C.

Melting point: 103°-105° C. (recrystallized from diisopropyl ether-diethyl ether (5:2 by volume)).

IR (KBr) cm$^{-1}$:$\nu_{C=O}$1670.

NMR (CDCl$_3$) δ values: 2.33 (3H, s), 2.60 (6H, s), 6.35-8.15 (9H, m), 9.60 (1H, bs).

In the same manner as above, the compounds shown in Table 4 were obtained.

EXAMPLE 17

In 10 ml of methylene chloride was dissolved 500 mg of 2-(2,4-difluorophenylamino)-5-fluoro-6-(mesitylenesulfonyloxy)nicotinoyl chloride, and 1 ml of a methylene chloride solution containing 77 mg of imidazole and 120 mg of triethylamine was dropped into the resulting solution at −20° C., after which the resulting

TABLE 4

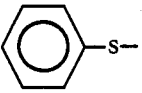

| Compound R[12] | m.p. (°C.) | IR (KBr) cm$^{-1}$: $\nu_{C=O}$ | NMR (*CDCl$_3$ **DMSO—d$_6$) δ values: |
|---|---|---|---|
| MeO— | 172.5–173 (recrystallized from benzene) | 1660 | **3.93 (3H, s), 6.75–8.35 (7H, m), 9.75 (1H, bs) |
| EtS— | 140.5–141 (recrystallized from ethyl acetate-n-hexane (1:1 by volume)) | 1670 | *1.28 (3H, t, J=7Hz), 3.08 (2H, q, J=7Hz), 6.65–8.20 (7H, m), 9.62 (1H, bs) |
| 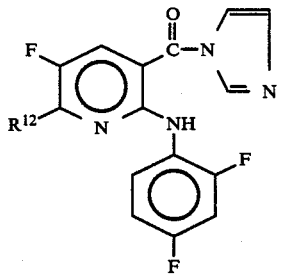 | 169.5–171 (recrystallized from ethyl acetate-n-hexane (1:1 by volume)) | 1650 | *6.05–8.20 (12H, m) 9.88 (1H, bs) |

EXAMPLE 18

In 7 ml of anhydrous tetrahydrofuran was dissolved 200 mg of 2-(2,4-difluorophenylamino)-5-fluoro-6-methoxynicotinoyl chloride, and 1 ml of an anhydrous tetrahydrofuran solution containing 45 mg of imidazole and 65 mg of triethylamine was dropped into the resulting solution at −20° to −10° C., after which the resulting mixture was subjected to reaction at room temperature for 30 minutes. Subsequently, 150 mg of magnesium ethoxycarbonylacetate was added thereto at room temperature, and the resulting mixture was subjected to reaction under reflux for 30 minutes, after which the reaction mixture was added to a mixture of 10 ml of ethyl acetate and 10 ml of water. The pH of the mixture was adjusted to 2.0 with 2N hydrochloric acid. The organic layer was separated, and 5 ml of water was added thereto, after which the pH thereof was adjusted to 7.5 with saturated aqueous sodium hydrogencarbonate solution. The organic layer was separated, washed successively with 5 ml of water and 5 ml of saturated aqueous sodium chloride solution, and then dried over anhydrous magnesium sulfate. The solvent was removed by distillation under reduced pressure, and to the crystalline material thus obtained was added 1 ml of diisiopropyl ether, after which crystals were collected by filtration to obtain 190 mg (yield 81.7%) of ethyl 2-[2-(2,4-difluorophenylamino)-5-fluoro-6-methoxynicotinoyl]acetate having a melting point of 148°–149° C.

Melting point: 149°–150° C. (recrystallized from benzene).

IR (KBr) cm$^{-1}$:$\nu_{C=O}$1745.

NMR (CDCl$_3$) δ values: 1.30 (3H, t, J=7 Hz), 3.90 (2H, s), 4.02 (3H, s), 4.27 (2H, q, J=7 Hz), 6.65–7.35 (2H, m), 7.73 (1H, d, J=10 Hz), 7.90–8.40 (1H, m), 11.19 (1H, bs).

EXAMPLE 19

The same procedure as in Examples 16 and 18 was repeated to obtain the compounds shown in Table 5.

TABLE 5

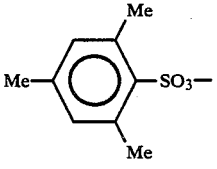

| Compound R² | Physical properties | | |
|---|---|---|---|
| | Melting point (°C.) | IR (KBr) cm⁻¹: $\nu_{C=O}$ | NMR (CDCl₃) δ values: |
| Cl— | 92.5–93 (recrystallized from diisopropyl ether) | 1745 | 1.31 (3H, t, J=7Hz), 3.97 (2H, s,), 4.25 (2H, q, J=7Hz), 6.65–7.35 (2H, m), 7.85 (1H, d, J=9Hz), 8.00–8.50 (1H, m), 10.91 (1H, bs) |
| 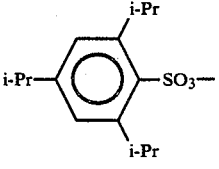 | 160–160.5 (recrystallized from benzene) | 1730 | 1.27 (3H, t, J=7Hz), 2.32 (3H, s), 2.57 (6H, s), 3.90 (2H, s), 4.20 (2H, q, J=7Hz), 6.35–7.30 (m) ⎱ (4H), 6.90 (s) ⎰ 7.57–8.12 (m) ⎱ (2H), 7.92 (d, J=9Hz) ⎰ 10.93 (1H, bs) |
| 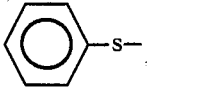 | 121–122.5 (recrystallized from diisopropyl ether) | 1730 | 1.22 (12H, d, J=7Hz), 1.28 (3H, t, J=7Hz), 1.29 (6H, d, J=7Hz), 2.65–3.25 (1H, m), 3.70–4.50 (m) ⎱ (6H), 3.97 (s) ⎰ 6.30–7.40 (m) ⎱ (4H), 7.23 (s) ⎰ 7.60–8.20 (m) ⎱ (2H), 8.00 (d, J=7Hz) ⎰ 11.07 (1H, bs) |
| EtS— | 102.5–103 (recrystallized from diisopropyl ether) | 1730 | 1.29 (6H, t, J=7Hz), 3.06 (2H, q, J=7Hz), 3.90 (2H, s), 4.22 (2H, q, J=7Hz), 6.64–7.35 (2H, m), 7.52 (1H, d, J=11Hz), 7.70–8.20 (1H, m), 10.86 (1H, bs) |
| 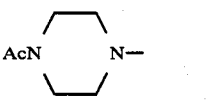 | 132.5–134 (recrystallized from ethyl acetate-n-hexane (10:1 by volume)) | 1725 | 1.27 (3H, t, J=7Hz), 3.89 (2H, s), 4.20 (2H, q, J=7Hz), 5.98–8.03 (9H, m), 11.12 (1H, bs) |
| AcN⟨  ⟩N— | 160–161 (recrystallized from benzene) | 1730 1640 | 1.28 (3H, t, J=7Hz), 2.12 (3H, s), 3.38–3.97 (10H, m), 4.22 (2H, q, J=7Hz), 6.67–7.20 (2H, m), 7.57 (1H, d, J=14Hz), 7.77–8.20 (1H, 10.98 (1H, bs) |
| H AcN—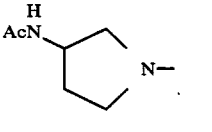N— | 184–185 (recrystallized from ethyl acetate-ethanol (1:1 by volume)) | 1735 1670 | 1.27 (3H, t, J=7Hz), 1.93–2.73 (m) ⎱ (5H), 2.02 (s) ⎰ 3.33–4.80 (m) ⎫ 3.65 (s) ⎬ (9H), 4.17 (q, J=7Hz) ⎭ 6.47–7.18 (m) ⎱ (3H), 7.03 (d, J=14Hz) ⎰ 8.00–8.38 (1H, m), 11.25 (1H, bs) |

EXAMPLE 20

In 4 ml of anhydrous tetrahydrofuran was dissolved 200 mg of 1-[2-(2,4-difluorophenylamino)-5-fluoro-6-(mesitylenesulfonyloxy)nicotinoyl]imidazole, and 90 mg of magnesium ethoxycarbonylacetate was added thereto, after which the resulting mixture was subjected to reaction at 50° to 60° C. for 20 minutes. Subsequently, the reaction mixture was added to a mixture of 10 ml of ethyl acetate and 10 ml of water, and the pH thereof was adjusted to 2.0 with 2N hydrochloric acid. The organic layer was separated, washed successively with 5 ml of water and 5 ml of saturated aqueous sodium chloride solution, and then dried over anhydrous magnesium sulfate. The solvent was removed by distillation under reduced pressure, and to the crystalline material thus obtained was added 1 ml of diethyl ether, after which crystals were collected by filtration to obtain 175 mg (yield 84.2%) of ethyl 2-[2-(2,4-difluorophenylamino)-5-fluoro-6-(mesitylenesulfonyloxy)nicotinoyl]acetate. The physical properties of this compound were identical with those of compound obtained in Example 19.

In the same manner as above, the following compounds were obtained.

Ethyl 2-[2-(2,4-difluorophenylamino)-5-fluoro-6-methoxynicotinoyl]acetate

Ethyl 2-[2-(2,4-difluorophenylamino)-6-ethylthio-5-fluoronicotionyl]acetate

Ethyl 2-[2-(2,4-difluorophenylamino)-5-fluoro-6-phenylthionicotinoyl]acetate

The physycal properties of these compounds were identical with those of the respective compounds obtained in Examples 18 and 19.

EXAMPLE 21

In 37 ml of anhydrous tetrahydrofuran was suspended 930 mg of 6-(3-acetylamino-1-pyrrolidinyl)-2-(2,4-difluorophenylamino)-5-fluoronicotinic acid, and 760 mg of N,N'-carbonyl diimidazole was added thereto with ice-cooling, after which the resulting mixture was subjected to reaction at room temperature for 12 hours. Subsequently, 670 mg of magnesium ethoxycarbonylacetate was added to the reaction mixture, and the resulting mixture was subjected to reaction at 60° C. for 2 hours. The reaction mixture was added to a mixture of 100 ml of ethyl acetate and 50 ml of water, and the pH thereof was adjusted to 2.0 with 2N hydrochloric acid, after which the organic layer was separated. To the organic layer was added 50 ml of water and the pH thereof was adjusted to 7.0 with saturated aqueous sodium hydrogencarbonate solution. The organic layer was separated, washed successively wity 50 ml of water and 50 ml of saturated aqueous sodium chloride solution, and dried over anhydrous magnesium sulfate. The solvent was removed by distillation under educed pressure, and the residue thus obtained was purified by a column chromatography [Wako Silica Gel C-200, eluant: chloroform-ethanol (200:1 by volume) to obtain 610 mg (yield 55.7%) of ethyl 2-[6-(3-acetylamino-1-pyrrolidinyl)-2-(2,4-difluorophenylamino)-5-fluoronicotionyl]acetate having a melting point of 182°–184° C.

EXAMPLE 22

(1) In 94 ml of anhydrous tetrahydrofuran was suspended 2.34 g of 2-(2,4-difluorophenylamino)-5-fluoro-6-hydroxyniconic acid, and 2.00 g of N,N'-carbonyldiimidazole was added thereto with ice-cooling, after which the resulting mixture was subjected to reaction at room temperature for 2 hours. Subsequently, 3.50 g of magnesium ethoxycarbonylacetate was added to the reaction mixture, and the mixture was subjected to reaction under reflux for 1.5 hours, after which the reaction mixture was added to a mixture of 150 ml of ethyl acetate and 150 ml of water, and the pH of the mixture was adjusted to 2.0 with 6N hydrochloric acid. The organic layer was separated, and washed successively with 80 ml of saturated aqueous sodium hydrogencarbonate solution and 80 ml of water, after which 80 ml of water was added thereto and the pH thereof was adjusted to 2.0 with 6N hydrochloric acid. The organic layer was separated, washed successively with 80 ml of water and 80 ml of saturated aqueous sodium chloride solution, and then dried over anhydrous magnesium sulfate. The solvent was removed by distillation under reduced pressure, and to the crystalline material thus obtained was added 8 ml of diethyl ether, after which crystals were collected by filtration to obtain 1.93 g (yield 66.2%) of ethyl 2-[2-(2,4difluorophenylamino)-5-fluoro-6-hydroxynicotinoyl]acetate having a melting point of 161°–162° C.

Melting point: 161.5°–162° C. (recrystallized from benzene).

IR (KBr) cm$^{-1}$: $\nu_{C=O}$ 1725, 1665.

NMR (CDCl$_3$) $\delta$ values: 1.29 (3H, t, J=7 Hz), 3.74 (2H, s), 4.20 (2H, q, J=7 Hz), 6.57–7.69 (4H, m), 10.17 (1H, bs), 11.52 (1H, bs).

In the same manner as above, ethyl 2-[5-fluoro-2-(4-fluorophenylamino)-6-hydroxynicotinoyl]acetate was obtained.

Melting point: 185° C. (decomp.) (recrystallized from ethyl acetate).

IR (KBr) cm$^{-1}$: $\nu_{C=O}$ 1715, 1685.

NMR (CDCl$_3$) $\delta$ values: 1.30 (3H, t, J=7 Hz), 3.75 (2H, s), 4.25 (2H, q, J=7 Hz), 7.08–7.34 (4H, m), 7.48 (1H, d, J=11 Hz), 11.86 (1H, bs).

(2) The same procedure as in (1) above was repeated, except that the reaction temperature and reaction time were altered to 60° C. and 3 hours, respectively to obtain ethyl 2-[2(2,4-difluorophenylamino)-5-fluoro-6-hydroxynicotinoyl]acetate in a yield of 34.5%.

EXAMPLE 23

In 30 ml of anhydrous tetrahydrofuran was dissolved 700 mg of 6-chloro-2-(2,4-difluorophenylamino)-5-fluoronicotinic acid, and 1.13 g of N,N'-carbonyldiimidazole was added thereto with ice-cooling, after which the resulting mixture was subjected to reaction at room temperature for 6 hours. Subsequently, 990 mg of magnesium ethoxycarbonylacetate was added thereto, and the resulting mixture was subjected to reaction at 55° C. for 2 hours, after which the reaction mixture was added to a mixture of 75 ml of ethyl acetate and 65 ml of water. The pH thereof was adjusted to 2.0 with 6N hydrochloric acid. The organic layer was separated and 30 ml of water was added, after which the pH thereof was adjusted to 7.5 with saturated aqueous sodium hydrogencarbonate solution. The organic layer was separated, washed successively with 30 ml of water and 30 ml of saturated aqueous sodium chloride solution, and then dried over anhydrous magnesium sulfate. The solvent was removed by distillation under reduced pressure, and the residue thus obtained was purified by a column chromatography [Wako Silica Gel C-200, eluant: benzene] to obtain 680 mg (yield 78.9%) of ethyl 2-[6-chloro-2-(2,4-difluorophenylamino)-5-fluoronicotinoyl]acetate. The physical properties of this compound were identical with those of the compound obtained in Example 19.

In the same manner as above, the following compounds were obtained:

Ethyl 2-[2-(2,4-difluorophenylamino)-5-fluoro-6-methoxynicotinoyl]acetate

Ethyl 2-[2-(2,4-difluorophenylamino)-6-ethylthio-5-fluoronicotinoyl]acetate

Ethyl 2-[2-(2,4-difluorophenylamino)-5-fluoro-6-phenylthionicotinoyl]acetate

Ethyl 2-[2-(2,4-difluorophenylamino)-5-fluoro-6-(2,4,6-trimethylbenzenesulfonyloxy)nicotinoyl]acetate Ethyl 2-[6-(4-acetyl-1-piperazinyl)-2-(2,4-difluorophenylamino)-5-fluoronicotinoyl]acetate The physical properties of these compounds were identical with those of the respective compounds obtained in Examples 18 and 19.

EXAMPLE 24

(1) In 3 ml of methylene chloride was suspended 280 mg of 2-(2,4-difluorophenylamino)-5-fluoro-6-methoxynicotinic acid, and 580 mg of thionyl chloride and one drop of N,N-dimethylformamide were added thereto at room temperature, after which the resulting mixture was subjected to reaction under reflux for 2 hours. The solvent and the excessive thionyl chloride were removed by distillation under reduced pressure, and the crystalline material thus obtained was dissolved in 6 ml of methylene chloride.

(2) In 6 ml of anhydrous tetrahydrofuran was dissolved 590 mg of diphenylmethyl ethyl malonate, and 90 mg of sodium hydride (purity: 50%) was added at $-20°$ C., after which the resulting mixture was subjected to reaction at 0° to 10° C. for 1 hour. Subsequently, the reaction mixture was cooled to $-20°$ C., and the methylene chloride solution obtained in (1) above was dropped thereinto at the same temperature, after which the resulting mixture was subjected to reaction at $-20°$ to $-10°$ C. for 30 minutes. To the reaction mixture was added 120 mg of acetic acid, and the solvent was removed by distillation under reduced pressure, after which to the residue thus obtained were added 20 ml of ethyl acetate and 10 ml of water. The pH thereof was adjusted to 2.0 with 2N hydrochloric acid. The organic layer was separated, washed successively with 10 ml of water and 10 ml of saturated aqueous sodium chloride solution, and then dried over anhydrous magnesium sulfate. The solvent was removed by distillation under reduced pressure, and to the residue thus obtained was added 5 ml of diisopropyl ether, after which crystals were collected by filtration to obtain 430 mg (yield 79.2%) of diphenylmethyl ethyl 2-(2,4-difluorophenylamino)-5-fluoro-6-methoxynicotinoylmalonate.

Melting point: 130°–131° C. (recrystallized from benzene-n-hexane (10:1 by volume)).

IR (KBr) cm$^{-1}$: $\nu_{C=O}$ 1740, 1730(sh).

NMR (CDCl$_3$) δ values: 1.24 (3H, t, J=7 Hz), 3.94 (3H, s), 4.28 (2H, q, J=7 Hz), 5.14 (1H, s), 6.40–7.64 (14H, m), 7.70–8.20 (1H, m), 11.10 (1H, bs).

(3) In 2 ml of anisole was dissolved 200 mg of diphenylmethyl ethyl 2-(2,4-difluorophenylamino)-5-fluoro-6-methoxynicotinoylmalonate, and 2 ml of trifluoroacetic acid was added thereto with ice-cooling, after which the resulting mixture was subjected to reaction at the same temperature for 10 minutes. The solvent was removed by distillation under reduced pressure, and to the crystalline material thus obtained was added 2 ml of diisopropyl ether, after which crystals were collected by filtration to obtain 120 mg (yield 94.3%) of ethyl 2-[2-(2,4-difluorophenylamino)-5-fluoro-6-methoxynicotinoyl]acetate.

The physical properties of this compound were identical with those of the compound obtained in Example 18.

EXAMPLE 25

In 2 ml of ethyl acetate was dissolved 100 mg of ethyl 2-[2-(2,4-difluorophenylamino)-5-fluoro-6-hydroxynicotinoyl]acetate, and a diethyl ether solution containing 15 mg of diazomethane was added thereto with ice-cooling, after which the resulting mixture was subjected to reaction at room temperature for 30 minutes. Subsequently, acetic acid was added to the reaction mixture until foaming was not caused in the reaction mixture. The solvent was then removed by distillation under reduced pressure and to the crystalline material thus obtained was added 2 ml of diisopropyl ether, after which crystals were collected by filtration to obtain 80 mg (yield 77.0%) of ethyl 2-[2-(2,4-difluorophenylamino)-5-fluoro-6-methoxynicotinoyl]acetate.

The physical properties of this compound were identical with those of the compound obtained in Example 18.

EXAMPLE 26

In 4 ml of methylene chloride was dissolved 400 mg of ethyl 2-[2-(2,4-difluorophenylamino)-5-fluoro-6-hydroxynicotinoyl]acetate, and 300 mg of 2,4,6-trimethylbenzenesulfonyl chloride and 150 mg of triethylamine were added thereto with ice-cooling, after which the resulting mixture was subjected to reaction at room temperature for 2 hours. Subsequently, to the reaction mixture were added 4 ml of methylene chloride and 4 ml of water, and the organic layer was separated, washed successively with 4 ml of water and 4 ml of saturated aqueous sodium chloride solution, and then dried over anhydrous magnesium sulfate. The solvent was removed by distillation under reduced pressure, and to the crystalline material thus obtained was added 2 ml of diethyl ether, after which crystals were collected by filtration to obtained 520 mg (yield 85.8%) of ethyl 2-[2-(2,4-difluorophenylamino)-5-fluoro-6-(2,4,6-trimethylbenzenesulfonyloxy)nicotinoyl]acetate. The physical properties of this compound were identical with those of the compound obtained in Example 19.

In the same manner as above, the following compounds were obtained:

Ethyl 2-[2-(2,4-difluorophenylamino)-5-fluoro-6-methanesulfonyloxynicotinoyl]acetate Melting point: 98°–99° C. (recrystallized from benzene).

IR (KBr) cm$^{-1}$: $\nu_{C=O}$ 1730.

| NMR (CDCl$_3$) δ values: |
| --- |
| 1.27 (3H, t, J=7Hz), 3.28 (3H, s), 3.93 (2H, s), |
| 4.23 (2H, q, J=7Hz), 6.63–7.43 (2H, m), |
| 7.70–8.23 (m) ⎫ 10.78 (1H, bs) |
| 7.97 (d, J=9Hz) ⎭ (2H), |

Ethyl 2-[2-(2,4-difluorophenylamino)-5-fluoro-6-(2,4,6-triisopropylbenzenesulfonyloxy)nicotinoyl]acetate.

The physical properties of this compound were identical with those of the compound obtained in Example 19.

EXAMPLE 27

In 1.5 ml of N,N-dimethylformamide was dissolved 150 mg of ethyl 2-[6-chloro-2-(2,4-difluorophenylamino)-5-fluoronicotinoyl]acetate, and 70 mg of thiophenol and 60 mg of triethylamine were added thereto, after which the resulting mixture was subjected to reaction at room temperature for 1 hour. Subsequently, to the reaction mixture were added 20 ml of ethyl acetate and 10 ml of water, and the pH thereof was adjusted to 2.0 with 2N hydrochloric acid. The organic layer was separated, washed successively with 10 ml of water and 10 ml of saturated aqueous sodium chloride solution, and then dried over anhydrous magnesium sulfate. The solvent was removed by distillation under reduced pressure, and to the crystalline material thus obtained was added 5 ml of n-hexane, after which crystals were collected by filtration to obtain 170 mg (yield 94.6%) of ethyl 2-[2-(2,4-difluorophenylamino)-5-fluoro-6-phhenylthionicotinoyl]acetate. The physical properties of this compound were identical with those of the compound obtained in Example 19.

EXAMPLE 28

In 1 ml of N,N-dimethylformamide was dissolved 100 mg of ethyl 2-[2-(2,4-difluorophenylamino)-5-fluoro-6-(2,4,6-trimethylbenzenesulfonyloxy)nicotinoyl]acetate, and 17 mg of ethanethiol and 28 mg of triethylamine were added thereto, after which the resulting mixture was subjected to reaction at room temperature for 4 hours. Subsequently, to the reaction mixture were added 3 ml of ethyl acetate and 3 ml of water, and the pH thereof was adjusted to 1.0 with 2N hydrochloric acid. The organic layer was separated, washed successively with 2 ml of water and 2 ml of saturated aqueous sodium chloride solution, and then dried over anhydrous magnesium sulfate. The solvent was removed by distillation under reduced pressure, and the residue thus obtained was purified by a column chromatography [Wako Silica Gel C-200, eluant: benzene-n-hexane (1:2 by volume)] to obtain 50 mg (yield 67.4%) of ethyl 2-[2-(2,4-difluorophenylamino)-6-ethylthio-5-fluoronicotinoyl]acetate. The physical properties of this compound were identical with those of the compound obtained in Example 19.

In the same manner as above, ethyl 2-[2-(2,4-difluorophenylamino)-5-fluoro-6-phenylthionicotinoyl]acetate. The physical properties of this compound were identical with those of the compound obtained in Example 19.

EXAMPLE 29

In 5 ml of chloroform was dissolved 500 mg of ethyl 2-[6-chloro-2-(2,4-difluorophenylamino)-5-fluoronicotinoyl]acetate, and 260 mg of 3-aminopyrrolidine dihydrochloride and 500 mg of triethylamine were added thereto, after which the resulting mixture was subjected to reaction under reflux for 1.5 hours. Subsequently, the reaction mixture was added to a mixture of 5 ml of chloroform and 5 ml of water, and the organic layer was separated, washed successively with 5 ml of water and 5 ml of saturated aqueous sodium chloride solution, and then dried over anhydrous magnesium sulfate. The solvent was removed by distillation under reduced pressure, and to the crystalline material thus obtained was added 2 ml of diisopropyl ether, after which crystals were collected by filtration to obtain 480 mg (yield 84.7%) of ethyl 2-[6-(3-amino-1-pyrrolidinyl)-2-(2,4-difluorophenylamino)-5-fluoronicotinoyl]acetate having a melting point of 140°–142° C.

IR (KBr) cm$^{-1}$: $\nu_{C=O}$ 1730.

NMR (DMSO-d$_6$) δ values: 1.22 (3H, t, J=7 Hz), 1.50–2.30 (2H, m), 3.30–4.40 (9H, m), 6.80–7.60 (2H, m), 7.81 (1H, d, J=14 Hz), 8.00–8.70 (1H, m), 11.45 (1H, bs).

EXAMPLE 30

In 1.5 ml of ethanol was dissolved 140 mg of anhydrous piperazine, and to the resulting solution was added 150 mg of ethyl 2-[6-chloro-2-(2,4-difluorophenylamino)-5-fluoronicotinoyl]acetate in portions, and the resulting mixture was subjected to reaction at room temperature for 30 minutes. Subsequently, the reaction mixture was added to a mixture of 5 ml of chloroform and 5 ml of water, and the organic layer was separated, washed successively with 3 ml of water and 3 ml of saturated aqueous sodium chloride solution, and then dried over anhydrous magnesium sulfate. The solvent was removed by distillation under reduced pressure, and to the crystalline material thus obtained was added 2 ml of n-hexane, after which crystals were collected by filtration to obtain 70 mg (yield 41.2%) of ethyl 2-[2-(2,4-difluorophenylamino)-5-fluoro-6-(1-piperazinyl)nicotinoyl]acetate.

Melting point: 121°–123° C. (recrystallized from ethyl acetate-n-hexane (10:1 by volume)).

IR (KBr) cm$^{-1}$: $\nu_{C=O}$ 1745, 1730(sh).

NMR (CDCl$_3$) δ values: 1.30 (3H, t, J=7 Hz), 2.76–3.10 (4H, m), 3.55–4.00 (6H, m), 4.21 (2H, q, J=7 Hz), 6.40–7.20 (2H, m), 7.47 (1H, d, J=14 Hz), 7.75–8.35 (1H, m), 11.10 (1H, bs).

EXAMPLE 31

In 1.5 ml of chloroform was suspended 50 mg of 3-aminopyrrolidine dihydrochloride, and 110 mg of triethylamine was added thereto after which the resulting mixture was subjected to reaction at room temperature for 10 minutes. Thereafter, 150 mg of ethyl 2-[2-(2,4-difluorophenylamino)-5-fluoro-6-(2,4,6-trimethylbenzenesulfonyloxy)-nicotionyl]acetate was added thereto, and the resulting mixture was subjected to reaction at room temperature for 1.5 hours. Subsequently, to the reaction mixture were added 5 ml of chloroform and 5 ml of water, and the organic layer was separated, washed successively with 5 ml of water and 5 ml of saturated aqueous sodium chloride solution, and then dried over anhydrous magnesium sulfate. The solvent was removed by distillation under reduced pressure, and to the crystalline material thus obtained was added 2 ml of diisopropyl ether, after which crystals were collected by filtration to obtain 110 mg (yield 93.2%) of ethyl 2-[6-(3-amino-1-pyrrolidinyl)-2-(2,4-difluorophenylamino)-5-fluoronicotionyl]acetate. The physical properties of this compound were identical with those of the compound obtained in Example 29.

EXAMPLE 32

In 2 ml of methylene chloride was dissolved 130 mg of anhydrous piperazine, and 200 mg of ethyl 2-[2-(2,4-difluorophenylamino)-5-fluoro-6-(2,4,6-trimethylbenzenesulfonyloxy)nicotinoyl]acetate was added thereto with ice-cooling, after which the resulting mixture was subjected to reaction at the same temperature for 40 minutes. Subsequently, the reaction mixture was added to a mixture of 10 ml of ethyl acetate and 10 ml of water, and the organic layer was separated, washed successively with 2 ml of saturated aqueous sodium hydrogencarbonate solution and 2 ml of saturated aqueous sodium chloride solution, and then dried over anhydrous magnesium sulfate. The solvent was removed by distillation under reduced pressure, and to the crystalline material thus obtained was added 1 ml of n-hexane, after which crystals were collected by filtration to obtain 110 mg (yield 69.9%) of ethyl 2-[2-(2,4-difluorophenylamino)-5-fluoro-6-(1-piperazinyl)nicotinoyl]acetate. The physical properties of this compound were identical with those of the compound obtained in Example 30.

EXAMPLE 33

In 1 ml of chloroform was dissolved 100 mg of ethyl 2-[6-(3-amino-1-pyrroldinyl)-2-(2,4-difluorophenylamino)-5-fluoronicotinoyl]acetate, and 26 mg of acetic anhydride was added thereto, after which the resulting mixture was subjected to reaction at room temperature for 30 minutes. Subsequently, the reaction mixture was added to a mixture of 1 ml of water and 1 ml of chloroform, and the organic layer was separated, washed successively with 1 ml of water and 1 ml of saturated aqueous sodium chloride solution and then dried over anhydrous magnesium sulfate. The solvent was removed by distillation under reduced pressure, and to the crystalline material thus obtained was added 0.5 ml of diisopropyl ether, after which crystals were collected by filtration to obtain 80 mg (yield 72.8%) of ethyl 2-[6-(3-acetylamino-1-pyrrolidinyl)-2-(2,4-difluorophenylamino)-5-fluoronicotinoyl]acetate. The physical properties of this compound were identical with those of the compound obtained in Example 19.

In the same manner as above, ethyl 2-[6-(4-acetyl-1-piperazinyl)-2-(2,4-difluorophenylamino)-5-fluoronicotinoyl]acetate was obtained. The physical properties of this compound were identical with those of the compound obtained in Example 19.

EXAMPLE 34

In 58 ml of N,N-dimethylformamide was dissolved 5.80 g of ethyl 2-[2-(2,4-difluorophenylamino)-5-fluoro-6-(2,4,6-triisopropylbenzenesulfonyloxy)nicotinoyl]acetate, and 1.24 g of thiophenol and 1.23 g of triethylamine were added thereto, after which the resulting mixture was subjected to reaction at room temperature for 4 hours. Subsequently, to the reaction mixture were added 400 ml of ethyl acetate and 200 ml of water, and the pH thereof was adjusted to 2.0 with 2N hydrochloric acid. The organic layer was separated, washed successively with 200 ml of water and 200 ml of saturated aqueous sodium chloride solution, and then dried over anhydrous magnesium sulfate. The solvent was removed by distillation under reduced pressure, and to the crystalline material thus obtained was added 50 ml of n-hexane, after which crystals were collected by filtration to obtain 3.99 g (yield 95.6%) of ethyl 2-[2-(2,4-difluorophenylamino)-5-fluoro-6-phenylthionicotinoyl]acetate. The physical properties of this compound were identical with those of the compound obtained in Example 19.

In the same manner as above, ethyl 2-[2-(2,4-difluorophenylamino)-6-ethylthio-5-fluoronicotinoyl]acetate was obtained. The physical properties of this compound were identical with those of the compound obtained in Example 19.

EXAMPLE 35

In 10 ml of anhydrous acetonitrile was suspended 1.00 g of ethyl 2-[2-(2,4-difluorophenylamino)-5-fluoro-6-hydroxynicotinoyl]acetate, and 390 mg of triethylamine and 670 mg of diethylphosphoryl chloride were added thereto with ice-cooling, after which the resulting mixture was subjected to reaction at room temperature for 1.5 hours. To this reaction mixture were added 50 ml of methylene chloride and 50 ml of water, and the organic layer was separated, washed with four 50-ml portions of water, and then dried over anhydrous magnesium sulfate. The solvent was removed by distillation under reduced pressure, and to the residue thus obtained was added 15 ml of n-hexane, after which the crystals thus deposited were collected by filtration to obtain 1.26 g (yield 91.0%) of ethyl 2-[6-diethoxyphosphinyloxy-2-(2,4-difluorophenylamino)-5-fluoronicotinoyl]acetate having a melting point of 127°–130° C.

Melting point: 131.5°–133° C. (recrystallized from benzene).

IR (KBr) cm$^{-1}$: $\nu_{C=O}$ 1740.

NMR (CDCl$_3$) δ values: 1.30 (3H, t, J=7 Hz), 1.33 (3H, t, J=7 Hz), 1.35 (3H, t, J=7 Hz), 3.95 (2H, s), 4.15 (2H, q, J=7 Hz), 4.25 (2H, q, J=7 Hz), 4.30 (2H, q, J=7 Hz), 6.65–7.35 (2H, m), 7.96 (1H, d, J=9 Hz), 8.15–8.75 (1H, m), 11.05 (1H, bs).

In the same manner as above, ethyl 2-[2-(2,4-difluorophenylamino)-6-diphenoxyphosphinyloxy-5-fluoronicotinoyl]acetate was obtained.

Melting point: 85°–86° C. (recrystallized from diethyl ether).

IR (KBr) cm$^{-1}$: $\nu_{C=O}$ 1740.

| NMR (CDCl$_3$) δ values: |
| --- |
| 1.25 (3H, t, J=7Hz), 3.90 (2H, s), |
| 4.20 (2H, q, J=7Hz), 6.30–7.60 (m) |
| 7.22 (bs)  } (12H), |
| 7.75–8.55 (2H, m), 11.07 (1H, bs) |

EXAMPLE 36

In 14 ml of methylene chloride was dissolved 1.40 g of ethyl 2-[2-(2,4-difluorophenylamino)-6-ethylthio-5-fluoronicotinoyl]acetate, and 1.59 g of m-chloroperbenzoic acid (purity: 80%) was added thereto with ice-cooling, after which the resulting mixture was subjected to reaction at room temperature for 3 hours. The precipitates were removed by filtration, and then, 10 ml of water was added to the filtrate thus obtained, after which the pH thereof was adjusted to 7.5 with saturated aqueous sodium hydrogencarbonate solution. The organic layer was separated, washed successively with 10 ml of water and 10 ml of saturated saqueous sodium chloride solution, and then dried over anhydrous magnesium sulfate. The solvent was removed by distillation under reduced pressure, and to the residue thus obtained was added 10 ml of diethyl ether, after which the crystals thus deposited were collected by filtration to obtain 1.28 g (yield 84.6%) of ethyl 2-[2-(2,4-difluorophenylamino)-6-ethanesulfonyl-5-fluoronicotinoyl]acetate having a melting point of 113°–114.5° C.

Melting point: 114°–115° C. (recrystallized from diisopropyl ether).

IR (KBr) cm$^{-1}$: $\nu_{C=O}$ 1740.

| NMR (CDCl₃) δ values: |
| --- |
| 1.24 (3H, t, J=7Hz), 1.27 (3H, t, J=7Hz), |
| 3.27 (2H, q, J=7Hz), 4.00 (2H, s), |
| 4.18 (2H, q, J=7Hz), 6.55–7.10 (2H, m), |
| 7.70–8.30 (m) ⎫ 10.60 (1H, bs), |
| 8.03 (d, J=9Hz) ⎬ (2H), |

In the same manner as above, ethyl 2-[6-benzenesulfonyl-2-(2,4-difluorophenylamino)-5-fluoronicotinoyl]acetate was obtained.

Melting point: 140°–141° C. (recrystallized from ethyl acetate).

IR (KBr) cm⁻¹ $\nu_{C=O}$ 1740.

| NMR (CDCl₃) δ values: |
| --- |
| 1.27 (3H, t, J=7Hz), 4.01 (2H, s), |
| 4.21 (2H, q, J=7Hz), 6.40–7.00 (2H, m), |
| 7.20–8.20 (m) ⎫ 10.72 (1H, bs) |
| 8.02 (d, J=9Hz) ⎬ (7H), |

EXAMPLE 37

In 20 ml of methylene chloride was dissolved 2.0 g of ethyl 2-[2-(2,4-difluorophenylamino)-5-fluoro-6-phenylthionicotinoyl]acetate, and 1.01 g of m-chloroperbenzoic acid (purity: 80%) was added thereto with ice-cooling, after which the resulting mixture was subjected to reaction at the same temperature for 5 hours. Subsequently, the precipitates were removed by filtration, and 20 ml of water was added to the filtrate thus obtained, after which the pH thereof was adjusted to 7.5 with saturated aqueous sodium hydrogencarbonate solution. The organic layer was separated, washed with 20 ml of water, and then dried over anhydrous magnesium sulfate. The solvent was removed by distillation under reduced pressure, and the residue thus obtained was purified by a column chromatography [Wako Silica Gel C-200, eluant: benzene-ethyl acetate (50:1 by volume)] to obtain 1.39 g (yield 67.1%) of ethyl 2-[6-benzenesulfinyl-2-(2,4-difluorophenylamino)-5-fluoronicotinoyl]acetate having a melting point of 105°–106.5° C.

Melting point: 107°–107.5° C. (recrystallized from diisopropyl ether).

IR (KBr) cm⁻¹: $\nu_{C=O}$ 1730

NMR (CDCl₃) δ values: 1.25 (3H, t, J=7 Hz), 3.97 (2H, s), 4.21 (2H, q, J=7 Hz), 6.60–8.00 (8H, m), 8.30–8.85 (1H, m), 10.90 (1H, bs).

In the same manner as above, ethyl 2-[2-(2,4-difluorophenylamino)-6-ethanesulfinyl-5-fluoronicotinoyl]acetate was obtained.

Melting point: 115°–116° C. (recrystallized from diisoether).

IR (KBr) cm⁻¹: $\nu_{C=O}$ 1735.

NMR (CDCl₃) δ values: 1.29 (3H, t, J=7 Hz), 1.31 (3H, t, J=7 Hz), 3.08 (2H, q, J=7 Hz), 4.03 (2H, s), 4.23 (2H, q, J=7 Hz), 6.65–7.15 (2H, m), 7.97 (1H, d, J=9 Hz), 8.40–9.00 (1H, m), 10.88 (1H, bs).

EXAMPLE 38

In 10 ml of anhydrous acetonitrile was suspended 1.05 g of ethyl 2-[2-(2,4-difluorophenylamino)-5-fluoro-6-hydroxynicotinoyl]acetate, and 450 mg of triethylamine and 1.22 g of diphenylphosphoryl azide were added thereto with ice-cooling, after which the resulting mixture was subjected to reaction at room temperature for 4 hours. To this reaction mixture were added 50 ml of ethyl acetate and 50 ml of water, and the organic layer was separated, and then dried over anhydrous magnesium sulfate. The solvent was removed by ditillation under reduced pressure, and the residue thus obtained was purified by a column chromoatography [Wako Silica Gel C-200, eluant: benzene] to obtain 550 mg (yield 48.9%) of ethyl 2-[6-azido-2-(2,4-difluorophenylamino)-5-fluoronicotinoyl]acetate having a melting point of 130°–131° C.

Melting point: 130.5°–131.5° C. (recrystallized from benzene).

IR (KBr) cm⁻¹: $\nu_{N_3}$ 2130, $\nu_{C=O}$ 1750

NMR (CDCl₃) δ values: 1.29 (3H, t, J=7 Hz), 3.92 (2H, s), 4.25 (2H, q, J=7 Hz), 6.60–8.45 (4H, m), 10.94 (1H, bs).

EXAMPLE 39

In 2 ml of benzene was suspended 200 mg of ethyl 2-[6-(3-acetylamino-1-pyrrolidinyl)-2-(2,4-difluorophenylamino)-5-fluoronicotinoyl]acetate, and 100 mg of N,N-dimethylformamide dimethylacetal was added thereto, after which the resulting mixture was subjected to reaction under reflux for 7 hours. Subsequently, the crystals thus deposited were collected by filtration and washed with 2 ml of dithyl ether to obtain 180 mg (yield 88.1%) of ethyl 7-(3-acetylamino-1-pyrrolidinyl)-1-(2,4-difluorophenyl)-6-fluoro-1,4-dihydro-4-oxo-1,8-naphthyridine-3-carboxylate having a melting point of 233°–236° C.

Melting point: 234°–236° C. (recrystallized from acetonemethanol (1:1 by volume)).

| NMR (CDCl₃) δ values: | |
| --- | --- |
| 1.33 (3H, t, J=7Hz), 1.76–2.47 (m) ⎫ | |
| 2.10 (s) ⎬ | (5H), |
| 3.13–4.02 (4H, m), 4.02–4.93 (m) ⎫ | |
| 4.32 (q, J=7Hz) ⎬ | (3H), |
| 6.78–7.70 (4H, m), 8.10 (1H, d, J=8Hz), | |
| 8.31 (1H, s) | |

In the same manner as above, ethyl 7-(4-acetyl-1-piperazinyl)-1-(2,4-difluorophenyl)-6-fluoro-1,4-dihydro-4-oxo-1,8-naphthyridine-3-carboxylate was obtained.

Yield: 84.2%.

Melting point: 219°–220° C. (recrystallized from acetone).

EXAMPLE 40

In 2 ml of benzene was suspended 200 mg of ethyl 2-[2-(2,4-difluorophenylamino)-5-fluoro-6-hydroxynicotinoyl]acetate, and 87 mg of N,N-dimethylformamide dimethylacetal was added thereto, after which the resulting mixture was subjected to reaction under reflux for 10 hours. Thereafter the crystals thus deposited were collected by filtration. To the crystals thus obtained were added 0.5 ml of methanol and 1 ml of water, and the pH thereof was adjusted to 1.0 with 2N hydrochloric acid, after which the crystals thus deposited were collected by filtration to obtain 80 mg (yield 38.9%) of ethyl 1-(2,4-difluorophenyl)-6-fluoro-1,4-dihydro-7-hydroxy-4-oxo-1,8-naphthyridine-3-carboxylate having a melting point of 243°–248° C.

Melting point: 250°–252° C. (recrystallized from acetonemethanol (1:1 by volume)).

IR (KBr) cm$^{-1}$: $\nu_{C=O}$ 1720.

NMR (TFA-d$_1$) δ values: 1.51 (3H, t, J=7 Hz), 4.70 (2H, q, J=7 Hz), 7.00–8.10 (3H, m), 8.30 (1H, d, J=8 Hz), 9.11 (1H, s)

In the same manner as above, ethyl 6-fluoro-1-(4-fluoropheneyl)-1,4-dihydro-7-hydroxy-4-oxo-1,8-naphthyridine-3-carboxylate was obtained.

Melting point: 252°–253° C. (recrystallized from acetonemethanol (1:1 by volume))

IR (KBr) cm$^{-1}$: $\nu_{C=O}$ 1730(sh), 1700.

NMR (TFA-d$_1$) δ values: 1.50 (3H, t, J=7 Hz), 4.64 (2H, q, J=7 Hz), 7.15–7.84 (4H, m), 8.20 (1H, d, J=9 Hz), 9.02 (1H, s).

EXAMPLE 41

In 4 ml of benzene was suspended 200 mg of ethyl 2-[2-(2,4-difluorophenylamino)-5-fluoro-6-methoxynicotinoyl]acetate, and 71 mg of N,N-dimethylformamide dimethylacetal was added thereto, after which the resulting mixture was subjected to reaction under reflux for 9 hours. The solvent was removed by distillation under reduced pressure, and to the residue thus obtained was added 2 ml of diethyl ether, after which the crystals thus deposited were collected by filtration to obtain 130 mg (yield 63.3%) of ethyl 1-(2,4-difluorophenyl)-6-fluoro-1,4-dihydro-7-methoxy-4-oxo-1,8-naphthyridine-3-carboxylate having a melting point of 190°–192° C.

Melting point: 193°–194° C. (recrystallized from ethyl acetate).

IR (KBr) cm$^{-1}$: $\nu_{C=O}$ 1730.

NMR (CDCl$_3$) δ values: 1.38 (3H, t, J=7 Hz), 3.78 (3H, s), 4.39 (2H, q, J=7 Hz), 6.82–7.82 (3H, m), 8.22 (1H, d, J=9 Hz), 8.46 (1H, s).

In the same manner as above, the compounds shown in Table 6 were obtained.

EXAMPLE 42

In 3 ml of benzene was dissolved 160 mg of ethyl 2-[2-(2,4-difluorophenylamino)-6-ethylthio-5-fluoronicotinoyl]acetate, and 72 mg of N,N-dimethylformamide dimethylacetal was added thereto, after which the resulting mixture was subjected to reaction under reflux for 2.5 hours. The solvent was removed by distillation under reduced pressure, and the residue thus obtained was purified by a column chromatography [Wako Silica Gel C-200, eluant: benzene-ethyl acetate (10:1 by volume)] to obtain 115 mg (yield 70.1%) of ethyl 1-(2,4-difluorophenyl)-7-ethylthio-6-fluoro-1,4-dihydro-4-oxo-1,8-naphthyridine-3-carboxylate having a melting point of 169.5°–171° C.

Melting point: 170°–171° C. (recrystallized from ethyl acetate).

IR (KBr) cm$^{-1}$: $\nu_{C=O}$ 1730.

NMR (CDCl$_3$) δ values: 1.08 (3H, t, J=7 Hz), 1.38 (3H, t, J=7 Hz), 2.79 (2H, q, J=7 Hz), 4.38 (2H, q, J=7 Hz), 6.88–7.83 (3H, m), 8.10 (1H, d, J=9 Hz), 8.48 (1H, s).

In the same manner as above, ethyl 1-(2,4-difluorophenyl)-6-fluoro-1,4-dihydro-4-oxo-7-phenylthio-1,8-naphthyridine-3-carboxylate was obtained.

Melting point: 218.5°–220° C. (recrystallized from acetone-methanol (1:1 by volume)).

IR (KBr) cm$^{-1}$: $\nu_{C=O}$ 1730, 1700(sh).

NMR (CDCl$_3$) δ values:
1.36 (3H, t, J=7Hz), 4.33 (2H, q, J=7Hz),
6.44–7.55 (m) ⎫
7.25 (s)      ⎬ (8H), 8.12 (1H, d, J=9Hz),
8.33 (1H, s)

TABLE 6

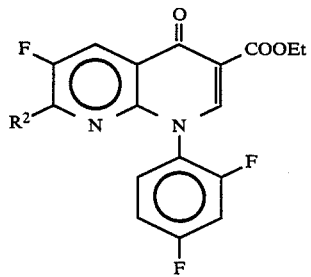

| Compound R$^2$ | Melting point (°C.) | IR (KBr) cm$^{-1}$:$\nu_{C=O}$ | NMR (CDCl$_3$) δ values: |
|---|---|---|---|
| Me-⟨benzene with Me, Me, SO$_3$-⟩ | 174–177 (recrystallized from chloroform) | 1740, 1700(sh) | 1.35 (3H, t, J=7Hz), 2.35 (3H, s), 2.46 (6H, s), 4.34 (2H, q, J=7Hz), 6.62–7.57 (5H, m), 8.41 (1H, s), 8.47 (1H, d, J=8Hz) |
| MeSO$_3$— | 187–188 (recrystallized from acetone) | 1735 | 1.39 (3H, t, J=7Hz), 3.12 (3H, s), 4.35 (2H, q, J=7Hz), 6.89–7.80 (3H, m), 8.46 (1H, d, J=9Hz), 8.50 (1H, s) |

EXAMPLE 43

In 4 ml of toluene was suspended 200 mg of ethyl 2-[2-(2,4-difluorophenylamino)-5-fluoro-6-hydroxynicotinoyl]acetate, and 200 mg of N,N-dimethylformamide dineopentylacetal was added thereto, after which the resulting mixture was subjected to reaction at room temperature for 4 hours. The crystals thus deposited were collected by filtration, and to the crystals were added 5 ml of ethanol and 5 ml of water, after which the pH thereof was adjusted to 1.0 with 2N hydrochloric acid. Thereafter, the crystals thus deposited were collected by filtration to obtain 155 mg (yield 75.4%) of ethyl 1-(2,4-difluorophenyl)-6-fluoro-1,4-dihydro-7-hydroxy-4-oxo-1,8-naphthyridine-3-carboxylate having a melting point of 244°-248° C. The physical properties of this compound were identical with those of the compound obtained in Example 40.

In the same manner as above, ethyl 6-fluoro-1-(4-fluorophenyl)-1,4-dihydro-7-hydroxy-4-oxo-1,8-naphthyridine-3-carboxylate was obtained in a yield of 72.8%. The physical properties of this compound were identical with those of the compound obtained in Example 40.

EXAMPLE 44

(1) In 6 ml of methylene chloride was dissolved 300 mg of ethyl 2-[2-(2,4-difluorophenylamino)-5-fluoro-6-(2,4,6-trimethylbenzenesulfonyloxy)nicotinoyl]acetate, and 135 mg of N,N-dimethylformamide dimethylacetal and 115 mg of acetic anhydride were added thereto, after which the resulting mixture was subjected to reaction at room temperature for 30 minutes. To the reaction mixture were added 0.31 ml of 2N hydrochloric acid and 3 ml of ethanol, and the resulting mixture was subjected to reaction at room temperature for 1 hour, after which 6 ml of methylene chloride and 6 ml of water were added thereto. The organic layer was separated, washed with 6 ml of saturated aqueous sodium chloride solution, and then dried over anhydrous magnesium sulfate. The solvent was removed by distillation under reduced pressure, and to the crystalline material thus obtained was added 2 ml of diisopropyl ether, after which crystals were collected by filtration to obtain 260 mg (yield 85.1%) of ethyl 1-(2,4-difluorophenyl)-6-fluoro-1,4-dihydro-4-oxo-7-(2,4,6-trimethylbenzenesulfonyloxy)-1,8-naphthyridine-3-carboxylate having a melting point of 170°-173° C. The physical properties of this compound were identical with those of the compound obtained in Example 41.

In the same manner as above, the compounds shown in Table 7 were obtained.

TABLE 7

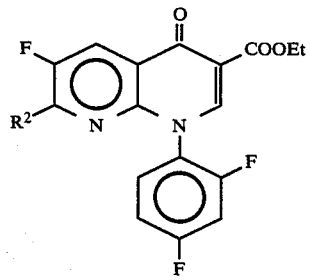

| Compound $R^2$ | Melting Point (°C.) | IR (KBr) cm$^{-1}$: $\nu_{C=O}$ | NMR (*CDCl$_3$) δ values: | Yield (%) |
|---|---|---|---|---|
| MeO— | Identical with those of the compound obtained in Example 41 | | | 85.2 |
| Cl— | 219–221 (recrystallized from acetone-methanol (1:1 by volume)) | — | — | 92.5 |
| 2,4,6-triisopropylphenyl-SO$_3$— | 177–178 (recrystallized from ethyl acetate-n-hexane (10:1 by volume)) | 1730, 1690 | 1.17 (12H, d, J=7Hz), 1.33 (6H, d, J=7Hz), 1.39 (3H, t, J=7Hz), 2.70–3.30 (1H, m), 3.60–4.60 (m), 4.36 (q, J=7Hz) } (4H), 6.58–7.65 (m), 7.19 (s) } (5H), 8.40 (1H, s), 8.40 (1H, d, J=9Hz) | 77.6 |
| MeSO$_3$— | Identical with those of the compound obtained in Example 41 | | | 78.2 |
| EtS— | Identical with those of the compound obtained in Example 42 | | | 93.7 |

TABLE 7-continued

Structure: 6-fluoro-7-R²-1-(2,4-difluorophenyl)-4-oxo-1,4-dihydro-1,8-naphthyridine-3-carboxylic acid ethyl ester

| Compound R² | Melting Point (°C.) | IR (KBr) cm$^{-1}$: $\nu_{C=O}$ | NMR (*CDCl₃) δ values: | Yield (%) |
|---|---|---|---|---|
| C₆H₅—S— | Identical with those of the compound obtained in Example 42 | | | 91.9 |
| EtS(O)— | 151–152 (recrystallized from ethyl acetate) | 1730, 1695 | 1.22 (3H, t, J=7Hz), 1.37 (3H, t, J=7Hz), 3.07 (2H, q, J=7Hz), 4.34 (2H, q, J=7Hz), 6.92–7.93 (3H, m), 8.42 (1H, d, J=9Hz), 8.66 (1H, s) | 85.0 |
| C₆H₅—S(O)— | 194–196 (recrystallized from acetone-methanol (5:1 by volume)) | 1735, 1695(sh) | 1.36 (3H, t, J=7Hz), 4.34 (2H, q, J=7Hz), 6.81–7.75 (8H, m), 8.36 (1H, d, J=8.5Hz), 8.55 (1H, s) | 75.3 |
| EtS(O)₂— | 216.5–217.5 (recrystallized from ethyl acetate-ethanol (1:1 by volume)) | 1730, 1700(sh) | 1.21 (3H, t, J=7Hz), 1.37 (3H, t, J=7Hz), 3.22 (2H, q, J=7Hz), 4.36 (2H, q, J=7Hz), 6.91–7.82 (3H, m), 8.57 (1H, d, J=9Hz), 8.62 (1H, s) | 91.9 |
| C₆H₅—S(O)₂— | 212–213 (recrystallized from acetone-ethanol (1:1 by volume)) | 1740, 1700(sh) | 1.35 (3H, t, J=7Hz), 4.30 (2H, q, J=7Hz), 6.58–7.86 (8H, m), 8.50 (1H, d, J=8.5Hz), 8.50 (1H, s) | 91.2 |
| (EtO)₂PO— | 133–134 (recrystallized from ethyl acetate-n-hexane (10:1 by volume)) | 1730(sh), 1685 | 1.27 (6H, t, J=7Hz), 1.38 (3H, t, J=7Hz), 3.98 (4H, q, J=7Hz), 4.37 (2H, q, J=7Hz), 6.81–7.82 (3H, m), 8.43 (1H, d, J=8.5Hz), 8.50 (1H, s) | 72.5 |
| (C₆H₅—O)₂PO— | 147–148 (recrystallized from ethyl acetate-n-hexane (10:1 by volume)) | 1725(sh), 1680 | *1.30 (3H, t, J=7Hz), 4.26 (2H, q, J=7Hz), 6.60–8.11 (13H, m), 8.56 (1H, d, J=9Hz), 8.75 (1H, s) | 82.7 |
| N₃— | 175–177 | 1725(sh), 1680, 2110 ($\nu_{N_3}$) | 1.39 (3H, t, J=7Hz), 4.36 (2H, q, J=7Hz), 6.84–7.75 (3H, m), 8.29 (1H, d, J=9Hz), 8.48 (1H, s) | 74.5 |
| 4-(AcNH)-piperidin-1-yl | Identical with those of the compound obtained in Example 39 | | | 86.1 |

Note:
*DMSO—d₆ was substituted for the CDCl₃ in measurement.

(2) The same procedure as in (1) above was repeated, except that one of the N,N-di-substituted formamide acetals shown in Table 8 was substituted for the N,N-dimethylformamide dimethylacetal to obtain the results shown in Table 8.

thylformamidedimethyl sulfate) complex compound to obtain the results shown in Table 9.

TABLE 9

TABLE 8

| Compound R² | N,N—di-substituted formamide acetal | Yield (%) | Physical properties of objective compound |
|---|---|---|---|
| MeO— | Me₂NCH(O-cyclohexyl)₂ | 82.3 | Identical with those of the compound obtained in Example 41 |
| H (AcN-pyrrolidinyl) | Same as above | 87.6 | Identical with those of the compound obtained in Example 39 |
| Same as above | Me₂N—C(O—)₂ | 70.5 | Same as above |

EXAMPLE 45

(1) To 4 ml of toluene was added 540 mg of (N,N-dimethylformamide-dimethyl sulfate) complex compound, and 85 mg of sodium methoxide was added thereto at 0° C., after which the resulting mixture was subjected to reaction at 0° to 10° C. for 1 hour. Subsequently, 200 mg of ethyl 2-[2-(2,4-difluorophenylamino)-5-fluoro-6-methoxynicotinoyl]acetate was further added to the reaction mixture, and the resulting mixture was subjected to reaction under reflux for 1.5 hours. The reaction mixture was added to a mixture of 8 ml of ethyl acetate and 8 ml of water, and the organic layer was separated, washed with 5 ml of saturated aqueous sodium chloride solution, and then dried over anhydrous magnesium sulfate. The solvent was removed by distillation under reduced pressure, and to the crystalline material thus obtained was added 1 ml of diethyl ether, after which crystals were collected by filtration to obtain 170 mg (yield 82.8%) of ethyl 1-(2,4-difluorophenyl)-6-fluoro-1,4-dihydro-7-methoxy-4-oxo-1,8-naphthyridine-3-carboxylate. The physical properties of this compound were identical with those of the compound obtained in Example 41.

(2) The same procedure as in (1) above was repeated, except that (N-formylpyrrolidine-dimethyl sulfate) complex compound was substituted for the (N,N-dime-

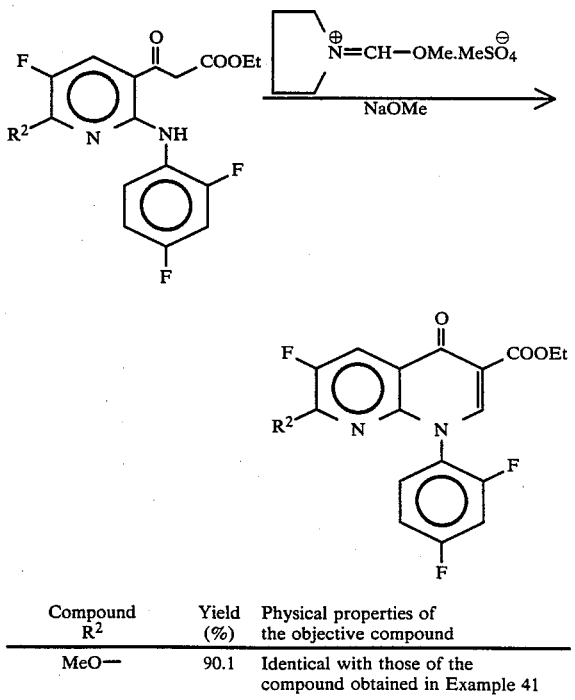

| Compound R² | Yield (%) | Physical properties of the objective compound |
|---|---|---|
| MeO— | 90.1 | Identical with those of the compound obtained in Example 41 |

TABLE 9-continued

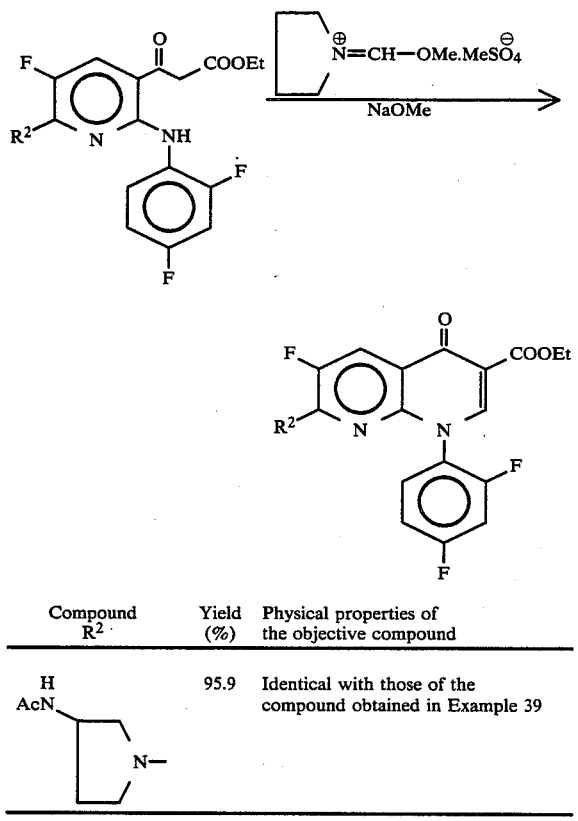

| Compound R[2] | Yield (%) | Physical properties of the objective compound |
|---|---|---|
| H AcN—[pyrrolidine]—N— | 95.9 | Identical with those of the compound obtained in Example 39 |

EXAMPLE 46

To 6 ml of methylene chloride was added 335 mg of (N,N-dimethylformamide-dimethyl sulfate) complex compound, and 65 mg of sodium methoxide was added thereto at 0° C., after which the resulting mixture was subjected to reaction at 0° to 10° C. for 1 hour. Subsequently, 300 mg of ethyl 2-[2-(2,4-difluorophenylamino)-5-fluoro-6-(2,4,6-trimethylbenzenesulfonyloxy)nicotinoyl]acetate and 115 mg of acetic anhydride were added thereto. The resulting mixture was subjected to reaction at room temperature for 2 hours, and 0.31 ml of 2N hydrochloric acid and 3 ml of ethanol were added to the reaction mixture, after which the resulting mixture was subjected to reaction at room temperature for 1.5 hours. The reaction mixture was added to a mixture of 6 ml of methylene chloride and 6 ml of water, and the organic layer was separated, washed with 6 ml of saturated aqueous sodium chloride solution, and then dried over anhydrous magnesium sulfate. The solvent was removed by distillation under reduced pressure, and to the crystalline material thus obtained was added 2 ml of diisopropyl ether, after which crystals were collected by filtration to obtain 245 mg (yield 80.2%) of ethyl 1-(2,4-difluorophenyl)-6-fluoro-1,4-dihydro-4-oxo-7-(2,4,6-trimethylbenzenesulfonyloxy)-1,8-naphthyridine-3-carboxylate. The physical properties of this compound were identical with those of the compound obtained in Example 41.

EXAMPLE 47

In 4 ml of toluene was suspended 200 mg of ethyl 2-[6-(3-amino-1-pyrrolidinyl)-2-(2,4-difluorophenylamino)-5-fluoronicotinoyl]acetate, and 170 mg of N,N-dimethylformamide dimethylacetal was added thereto, after which the resulting mixture was subjected to reaction under reflux for 7 hours. Subsequently, the solvent was removed by distillation under reduced pressure, and to the residue thus obtained was added 1 ml of diethyl ether, after which crystals were collected by filtration to obtain 195 mg (yield 84.5%) of ethyl 1-(2,4-difluorophenyl)-7-[3-(N,N-dimethylaminomethyleneimino)-1-pyrrolidinyl]-6-fluoro-1,4-dihydro-4-oxo-1,8-naphthyridine-3-carboxylate having a melting point of 136°–138° C. This was recrystallized from ethanol to obtain crystals having a melting point of 137°–139° C.

IR (KBr) cm$^{-1}$: $\nu_{C=O}$ 1730, 1690.

NMR (CDCl$_3$) δ values: 1.38 (3H, t, J=7 Hz), 1.65–2.15 (2H, m), 2.85 (6H, s), 3.10–3.95 (5H, m), 4.34 (2H, q, J=7 Hz), 6.75–7.70 (4H, m), 7.92 (1H, d, J=13 Hz), 8.30 (1H, s).

EXAMPLE 48

To 4 ml of toluene was added 245 mg of (N,N-dimethylformamide-dimethyl sulfate) complex compound, and 66 mg of sodium methoxide was added thereto with ice-cooling after which the resulting mixture was subjected to reaction at room temperature for 30 minutes. Subsequently, 200 mg of ethyl 2-[6-(3-acetylamino-1-pyrrolidinyl)-2-(2,4-difluorophenylamino)-5-fluoronicotinoyl]acetate was added thereto, and the resulting mixture was subjected to reaction under reflux for 5 hours. To the reaction mixture were added 20 ml of chloroform and 20 ml of water, and the organic layer was separated, washed with 20 ml of saturated aqueous sodium chloride solution, and then dried over anhydrous magnesium sulfate. The solvent was removed by distillation under reduced pressure, and the residue thus obtained was purified by a column chromatography [Wako Silica Gel C-200, eluant: chloroform-ethanol (50:1 by volume)] to obtain 190 mg (yield 84.9%) of ethyl 2-[6-(3-acetylamino-1-pyrrolidinyl)-2-(2,4-difluorophenylamino)-5-fluoronicotinoyl]-3-(N,N-dimethylamino)acrylate having a melting point of 184°–186° C.

IR (KBr) cm$^{-1}$: $\nu_{C=O}$ 1680, 1635(sh).

| NMR (CDCl$_3$) δ values: |
|---|
| 1.15 (3H, t, J=7Hz), 1.75–2.30 (m) ⎫<br>1.93 (s) ⎬ (5H)<br>⎭ |
| 2.91 (6H, s), 3.25–4.70 (7H, m), 6.45–7.10 (2H, m), 7.38 (1H, d, J=14Hz), 7.53 (1H, s), 8.10–8.65 (1H, m), 11.62 (1H, bs) |

EXAMPLE 49

In 1 ml of dioxane were dissolved 80 mg of ethyl 2-[2-(2,4-difluorophenylamino)-5-fluoro-6-hydroxynicotinoyl]acetate, 46 mg of acetic anhydride and 50 mg of ethyl ortho-formate, and the resulting solution was subjected to reaction under reflux for 7 hours, after which the solvent was removed by distillation under reduced pressure. The residue thus obtained was dissolved 10 ml of methanol and 5 ml of water, and the pH thereof was adjusted to 8.5 with a 10% by weight aqueous sodium carbonate solution. The resulting mixture was subjected to reaction at room temperature for 30 minutes, and the pH of the reaction mixture was adjusted to 2.0 with 2N hydrochloric acid, after which 20 ml of ethyl acetate and 10 ml of water were added thereto. The organic layer was separated, washed successively with 15 ml of water and 15 ml of saturated aqueous sodium chloride solution, and then dried over anhydrous magnesium sulfate. The solvent was removed by distillation under reduced pressure, and to the residue thus obtained was added 1 ml of diethyl ether, after which the crystals thus deposited were collected by filtration to obtain 43 mg (yield 52.3%) of ethyl 1-(2,4-difluorophenyl)-6-fluoro-1,4-dihydro-7-hydroxy-4-oxo-1,8-naphthyridine-3-carboxylate. The physical properties of this compound were identical with those of the compound obtained in Example 40.

EXAMPLE 50

In 1 ml of dioxane were dissolved 100 mg of ethyl 2-[2-(2,4-difluorophenylamino)-5-fluoro-6-methoxynicotinoyl]acetate, 55 mg of acetic anhydride and 60 mg of ethyl ortho-formate, and the resulting solution was subjected to reaction under reflux for 7 hours. Subsequently, the reaction mixture was added to a mixture of 3 ml of ethyl acetate and 3 ml of water, and the organic layer was separated, washed successively with 3 ml of water and 3 ml of saturated aqueous sodium chloride solution, and then dried over anhydrous magnesium sulfate. The solvent was removed by distillation under reduced pressure, and to the crystalline material thus obtained was added 1 ml of diethyl ether, after which crystals were collected by filtration to obtain 45 mg (yield 43.8%) of ethyl 1-(2,4-difluorophenyl)-6-fluoro-1,4-dihydro-7-methoxy-4-oxo-1,8-naphthyridine-3-carboxylate. The physical properties of this compound were identical with those of the compound obtained in Example 41.

EXAMPLE 51

(1) Into 4 ml of N,N-dimethylformamide was dropped 250 mg of phosphorus oxychloride with ice-cooling, and 200 mg of ethyl 2-[2-(2,4-difluorophenylamino)-5-fluoro-6-methoxynicotinoyl]acetate was added thereto after stirring at the same temperature for 10 minutes. The resulting mixture was subjected to reaction at 50° to 60° C. for 3.5 hours. The reaction mixture was poured into 50 ml of iced water, and 20 ml of chloroform was added thereto, after which the organic layer was separated, washed with 20 ml of water, and then dried over anhydrous magnesium sulfate. The solvent was removed by distillation under reduced pressure, and to the residue thus obtained was added 5 ml of diethyl ether, after which crystals were collected by filtration to obtain 150 mg (yield 72.2%) of ethyl 7-chloro-6-fluoro-1-(2,4-difluorophenyl)-1,4-dihydro-4-oxo-1,8-naphthyridine-3-carboxylate having a melting point of 217°–220° C. This was recrystallized from an acetone-methanol mixture (1:1 by volume) to obtain crystals having a melting point of 219°–221° C.

Elementary analysis values for $C_{17}H_{10}N_2O_3ClF_3$: Calcd. (%): C, 53.35; H, 2.63; N, 7.32. Found (%): C, 53.61; H, 2.47; N, 6.96.

(2) The same procedure as in (1) above was repeated using the starting compounds shown in Table 10 to obtain the objective compound shown in Table 10 in the yields shown in Table 10.

TABLE 10

| Starting compound R² | Yield of objective compound (%) |
|---|---|
| HO— | 88.9 |
| MeSO₃— | 96.6 |
| 2,4,6-trimethylphenyl-SO₃— | 84.8 |
| (EtO)₂P(O)— | 84.6 |
| (PhO)₂P(O)— | 76.9 |
| EtSO₂— | 76.5 |
| PhSO₂— | 78.9 |

The physical properties of the objective compound were identical with those of the compound obtained in (1) above.

(3) The same procedure as in (1) above was repeated using ethyl 2-[2-(4-fluorophenylamino)-5-fluoro-6-hydroxynicotinoyl]acetate to obtain ethyl 7-chloro-1-(4-fluorophenyl)-6-fluoro-1,4-dihydro-4-oxo-1,8-naphthyridine-3-carboxylate in a yield of 74.9%.

Melting point: 230°–232° C. (recrystallized from acetone).

IR (KBr) cm⁻¹: $\nu_{C=O}$ 1730, 1700.

NMR (CDCl₃) δ values: 1.38 (3H, t, J=7 Hz), 4.34 (2H, q, J=7 Hz), 6.90–7.60 (4H, m), 8.37 (1H, d, J=7 Hz), 8.53 (1H, s).

Elementary analysis values for $C_{17}H_{11}N_2O_3ClF_2$: Calcd. (%): C, 55.98; H, 3.04, N, 7.68. Found (%): C, 56.09; H, 2.92; N, 7.68.

(4) The same procedure as in (1) above was repeated, except that one of the halides shown in Table 11 was substituted for the phosphorus oxychloride to obtain the results shown in Table 11.

TABLE 11

[Chemical structures: starting material with F, MeO, N, CCH₂COOEt, NH, and difluorophenyl groups reacting with Halide/DMF to give the cyclized product with Cl, F, N, COOEt, and difluorophenyl groups]

| Halide (Charged amount) | Amount of objective compound obtained (yield) |
| --- | --- |
| Diphosgene (160 mg) | 150 mg (72.2%) |
| Phosphorus pentachloride (340 mg) | 145 mg (69.8%) |
| Phosphorus trichloride (225 mg) | 125 mg (60.1%) |

In the respective cases, the physical properties of the objective compounds obtained were identical with those of the compound obtained in (1) above.

EXAMPLE 52

(1) In 2 ml of 1,2-dichloroethane was dissolved 130 mg of N,N-dimethylformamide, and 270 mg of phosphorus oxychloride was dropped thereinto with ice-cooling, after which the resulting mixture was subjected to reaction at the same temperature for 10 minutes. Thereafter, 200 mg of ethyl 2-[2-(2,4-difluorophenylamino)-5-fluoro-6-methoxynicotinoyl]acetate was added to the reaction mixture, and the resulting mixture was subjected to reaction under reflux for 4.5 hours. The reaction mixture was poured into 30 ml of water, and 30 ml of chloroform was then added thereto. The organic layer was thereafter separated, washed successively with 20 ml of water and 20 ml of saturated aqueous sodium chloride solution, and then dried over anhydrous magnesium sulfate. The solvent was removed by distillation under reduced pressure, and the residue thus obtained was purified by a column chromatography [Wako Silica Gel C-200, eluant: benzene-ethyl acetate (10:1 by volume)] to obtain 130 mg (yield 62.6%) of ethyl 7-chloro-1-(2,4-difluorophenyl)-6-fluoro-1,4-dihydro-4-oxo-1,8-naphthyridine-3-carboxylate. The physical properties of this compound were identical with those of the compound obtained in Example 51.

(2) The same procedure as in (1) above was repeated, except that 160 ml of N-formylpyrrolidine was substituted for the N,N-dimethylformamide to obtain 135 mg (yield 65.0%) of ethyl 7-chloro-1-(2,4-difluorophenyl)-6-fluoro-1,4-dihydro-4-oxo-1,8-naphthyridine-3-carboxylate. The physical properties of this compound were identical with those of the compound obtained in Example 51 (1).

EXAMPLE 53

In 4 ml of ethanol was suspended 200 mg of ethyl 2-[6-(3-acetylamino-1-pyrrolidinyl)-2-(2,4-difluorophenylamino)-5-fluoronicotinoyl]-3-(N,N-dimethylamino)acrylate, and 0.4 ml of 1N hydrochloric acid was added thereto, after which the resulting mixture was subjected to reaction at room temperature for 5 minutes. Subsequently, to the reaction mixture were added 10 ml of chloroform and 10 ml of water, and the organic layer was separated, washed successively with 10 ml of water and 10 ml of saturated aqueous sodium chloride solution, and then dried over anhydrous magnesium sulfate. The solvent was removed by distillation under reduced pressure, and to the crystalline material thus obtained was added 4 ml of diethyl ether, after which crystals were collected by filtration to obtain 180 mg (yield 98.6%) of ethyl 7-(3-acetylamino-1-pyrrolidinyl)-1-(2,4-difluorophenyl)-6-fluoro-1,4-dihydro-4-oxo-1,8-naphthyridine-3-carboxylate. The physical properties of this compound were identical with those of the compound obtained in Example 39.

EXAMPLE 54

In 4 ml of ethanol was suspended 200 mg of ethyl 2-[6-(3-acetylamino-1-pyrrolidinyl)-2-(2,4-difluorophenylamino)-5-fluoronicotinoyl]-3-(N,N-dimethylamino)acrylate, and 4 ml of 6N hydrochloric acid was added thereto, after which the resulting mixture was subjected to reaction under reflux for 3.5 hours. Subsequently, the solvent was removed by distillation under reduced pressure, and to the crystalline material thus obtained was added 2 ml of ethanol, after which crystals were collected by filtration to obtain 145 mg (yield 85.4%) of 7-(3-amino-1-pyrrolidinyl)-1-(2,4-difluorophenyl)-6-fluoro-1,4-dihydro-4-oxo-1,8-naphthyridine-3-carboxylic acid hydrochloride.

Melting point: 247°–250° C. (decomp.) (recrystallized from conc. hydrochloric acid-ethanol (1:3 by volume)).

IR (KBr) cm$^{-1}$ $\nu_{C=O}$ 1730.

NMR (TFA-d$_1$) δ values: 2.23–2.95 (2H, m), 3.38–4.83 (5H, m), 6.95–7.90 (3H, m), 8.22 (1H, d, J=11 Hz), 9.18 (1H, s).

EXAMPLE 55

In 20 ml of N,N-dimethylformamide was dissolved 1.00 g of ethyl 1-(2,4-difluorophenyl)-6-fluoro-1,4-dihydro-7-hydroxy-4-oxo-1,8-naphthyridine-3-carboxylate, and 570 mg of potassium carbonate and 520 mg of dimethyl sulfate were added thereto at room temperature, after which the resulting mixture was subjected to reaction at the same temperature for 4 hours. To the reaction mixture were added 50 ml of water and 50 ml of ethyl acetate, and the organic layer was separated, washed successively with 100 ml of water and 20 ml of saturated aqueous sodium chloride solution, and then dried over anhydrous magnesium sulfate. The solvent was removed by distillation under reduced pressure, and to the crystalline material thus obtained was added 5 ml of diethyl ether, after which crystals were collected by filtration to obtain 950 mg (yield 91.5%) of ethyl 1-(2,4-difluorophenyl)-6-fluoro-1,4-dihydro-7-methoxy-4-oxo-1,8-naphthyridine-3-carboxylate. The physical properties of this compound were identical with those of the compound obtained in Example 41.

EXAMPLE 56

In 30 ml of methylene chloride was suspended 3.00 g of ethyl 1-(2,4-difluorophenyl)-6-fluoro-1,4-dihydro-7-hydroxy-4-oxo-1,8-naphthyridine-3-carboxylate, and 1.02 g of triethylamine and 2.20 g of ortho-nitrobenzenesulfonyl chloride were added thereto with ice-cooling, after which the resulting mixture was subjected to reaction at the same temperature for 30 minutes and then at room temperature for 6 hours. The reaction mixture was washed with three 50-ml portions of water and then dried over anhydrous magnesium sulfate. The solvent was removed by distillation under reduced pressure, and to the residue thus obtained was added a mixture of 6 ml of ethyl acetate and 12 ml of diethyl ether, after which the crystals thus deposited were collected by filtration to obtain 4.40 g (yield 97.2%) of ethyl 1-(2,4-difluorophenyl)-6-fluoro-1,4-dihydro-7-(2-nitrobenzenesulfonyloxy)-4-oxo-1,8-naphthyridine-3-carboxylate having a melting point of 157°–160° C.

Melting point: 162°–163° C. (recrystallized from acetone-n-hexane (10:1 by volume).

IR (KBr) cm$^{-1}$: $\nu_{C=O}$ 1730, 1700 (sh).

NMR (DMSO-$d_6$) δ values: 1.30 (3H, t, J=7 Hz), 4.24 (2H, q, J=7 Hz), 7.03–8.26 (7H, m), 8.64 (1H, d, J=9 Hz), 8.72 (1H, s).

In the same manner as above, the compounds shown in Table 12 were obtained.

TABLE 12

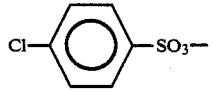

| Compound R$^2$ | X | Melting point (°C.) | IR (KBr) cm$^{-1}$: $\nu_{C=O}$ | NMR (*CDCl$_3$ / **DMSO—$d_6$) δ values: |
|---|---|---|---|---|
| F$_3$CSO$_3$— | F | 120–121 (recrystallized from ethyl acetate-n-hexane (10:1 by volume)) | 1730(sh), 1690 | *1.40(3H, t, J=7Hz), 4.38 (2H, q, J=7Hz), 6.90–7.74 (3H, m), 8.57 (H, s), 8.61 (1H, d, J=9Hz) |
| 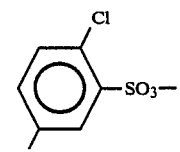 | F | 167–168 (recrystallized from ethyl acetate) | 1740, 1700 | *1.37(3H, t, J=7Hz), 4.36 (2H, q, J=7Hz), 6.91–7.82 (7H, m), 8.48(1H, d, J=9Hz), 8.53(1H, s) |
| 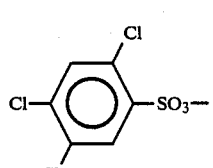 | F | 164–166 (recrystallized from ethyl acetate) | 1730, 1690 | *1.35(3H, t, J=7Hz), 4.32 (2H, q, J=7Hz), 6.7–7.7(6H, m), 8.43(1H, s), 8.48(1H, d, J=8Hz) |
| Cl—⌬(Cl,Cl)—SO$_3$— | F | 169–171 (recrystallized from ethyl acetate) | 1735, 1700 | *1.36(3H, t, J=7Hz), 4.31 (2H, q, J=7Hz), 6.7–7.9 (5H, m), 8.43(1H,s), 8.49(1H, d, J=8Hz) |
| 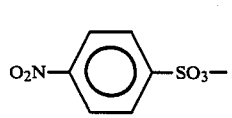 | F | 168–170 (recrystallized from ethyl acetate | 1730, 1700(sh) | **1.27(3H, t, J=7Hz), 4.20 (2H, q, J=7Hz), 6.97–8.55 (m), 7.94 (d, J=9Hz), 8.30 (d, J=9Hz) } (8H), 8.65 (1H, s) |

TABLE 12-continued

Structure: 6-F, 7-R² substituted pyrido-quinolone with 3-COOEt, 1-(2-X-4-F-phenyl) group

| Compound R² | X | Melting point (°C.) | IR (KBr) cm⁻¹: $\nu_{C=O}$ | NMR (*CDCl₃, **DMSO—d₆) δ values: |
|---|---|---|---|---|
| 2,4,6-tri-i-Pr-phenyl-SO₃— | H | 186–187 (recrystallized from acetone-methanol(1:1 by volume)) | 1735, 1690 | *1.15(12H, d, J=7Hz), 1.30(6H, d, J=7Hz), 1.35 (3H, t, J=7Hz), 2.96(1H, m), 3.60–4.60 (m) ⎫ 4.35(q, J=7Hz) ⎬(4H), 6.83–7.47(m) ⎫ 7.17(s) ⎬(6H), 8.50(1H, d, J=8Hz), 8.58 (1H, s) |
| 2-NO₂-phenyl-SO₃— | H | 186–186.5 (Recrystallized from acetone) | 1735, 1700 | **1.25(3H, t, J=7Hz), 4.19(2H, q, J=Hz), 6.95–8.19(8H,m), 8.48 (1H, s), 8.52(1H, d, J=8Hz) |
| MeSO₃— | F | Identical with those of the compound obtained in Example 41 | | |
| Me₂CHSO₃— | F | 198.5–199 (recrystallized from dioxane) | 1740, 1700(sh) | *1.37(3H, t, J=7Hz), 1.38 (6H, d, J=7Hz), 3.41(1H, m), 4.36(2H, q, J=7Hz), 6.88–7.77(3H, m), 8.47(1H, d, J=9Hz), 8.51(1H, s) |
| 4-Me-phenyl-SO₃— | F | 165–165.5 (recrystallized from ethyl acetate) | 1740, 1700(sh) | *1.36(3H, t, J=7Hz), 2.44 (3H, s), 4.33(2H, q, J=7Hz), 6.86–7.74(7H, m), 8.36(1H, d, J=9Hz), 8.48(1H, s) |
| 2,4,6-tri-Me-phenyl-SO₃— | F | Identical with those of the compound obtained in Example 41 | | |
| 2,4,6-tri-i-Pr-phenyl-SO₃— | F | Identical with those of the compound obtained in Example 44 | | |
| naphthalen-1-yl-SO₃— | F | 156–157.5 (recrystallized from ethyl acetate-n-hexane (10:1 by volume) | 1735, 1680 | *1.34(3H, t, J=Hz), 4.35 (2H, q, J=7Hz), 6.74–8.18 (10H, m), 8.36(1H, s), 8.43(1H, d, J=8Hz) |

EXAMPLE 57

In 5 ml of anhydrous acetonitrile was suspended 500 mg of ethyl 1-(2,4-difluorophenyl)-6-fluoro-1,4-dihydro-7-hydroxy-4-oxo-1,8-naphthyridine-3-carboxylate, and 150 mg of triethylamine and 410 mg of diphenylphosphoryl chloride were added thereto with ice-cooling, after which the resulting mixture was subjected to reaction at room temperature for 2 hours. To the reaction mixture were added 25 ml of methylene chloride and 25 ml of water, and the organic layer was separated, washed successively with two 20-ml portions of water and 20 ml of saturated aqueous sodium chloride solution, and then dried over anhydrous magnesium sulfate. The solvent was removed by distillation under reduced pressure, and to the residue thus obtained was added 15 ml of diethyl ether, after which the crystals thus deposited were collected to obtain 700 mg (yield 85.5%) of ethyl 1-(2,4-difluorophenyl)-7-(diphenoxyphosphinyloxy)-6-fluoro-1,4-dihydro-4-oxo-1,8-naphthyridine-3-carboxylate having a melting point of 144°-147° C. The physical properties of this compound were identical with those of the compound obtained in Example 44.

In the same manner as above, ethyl 7-(diethoxyphosphinyloxy)-1-(2,4-difluorophenyl)-6-fluoro-1,4-dihydro-4-oxo-1,8-naphthyridine-3-carboxylate was obtained, and the physical properties of this compound were identical with those of the compound obtained in Example 44.

EXAMPLE 58

In 5 ml of pyridine was suspended 500 mg of ethyl 1-(2,4-difluorophenyl)-6-fluoro-1,4-dihydro-7-hydroxy-4-oxo-1,8-naphthyridine-3-carboxylate, and 770 mg of diphenylphosphoryl azide was added thereto, after which the resulting mixture was subjected to reaction at 80° C. for 4 hours. The solvent was thereafter removed by distillation under reduced pressure, and to the residue thus obtained were added 10 ml of ethyl acetate and 10 ml of water, after which the pH of the resulting mixture was adjusted to 2.0 with 6N hydrochloric acid. The organic layer was then separated, washed successively with 5 ml of saturated aqueous sodium hydrogencarbonate solution and 5 ml of water, and then dried over anhydrous magnesium sulfate. The solvent was removed by distillation under reduced pressure, and to the residue thus obtained was added 5 ml of diethyl ether, after which the crystals thus deposited were collected by filtration to obtain 440 mg (yield 82.3%) of ethyl 7-azido-1-(2,4-difluorophenyl)-6-fluoro-1,4-dihydro-4-oxo-1,8-naphthyridine-3-carboxylate having a melting point of 176°-177.5° C. The physical properties of this compound were identical with those of the compound obtained in Example 44.

EXAMPLE 59

In 10 ml of methylene chloride was dissolved 1.00 g of ethyl 1-(2,4-difluorophenyl)-7-ethylthio-6-fluoro-1,4-dihydro-4-oxo-1,8-naphthyridine-3-carboxylate, and 580 mg of m-chloroperbenzoic acid (purity: 80%) was added thereto, after which the resulting mixture was subjected to reaction with ice-cooling for 5 hours. The precipitates were removed by filtration, and to the filtrate thus obtained was added 10 ml of water, after which the pH thereof was adjusted to 7.5 with saturated aqueous sodium hydrogencarbonate solution. The organic layer was thereafter separated, washed with 10 ml of water, and then dried over anhydrous magnesium sulfate. The solvent was removed by distillation under reduced pressure, and the residue thus obtained was purified by a column chromatography [Wako Silica Gel C-200, eluant: toluene-ethyl acetate (10:1 by volume)] to obtain 810 mg (yield 77.9%) of ethyl 1-(2,4-difluorophenyl)-7-ethylsulfinyl-6-fluoro-1,4-dihydro-4-oxo-1,8-naphthyridine-3-carboxylate having a melting point of 150°-151° C. The physical properties of this compound were identical with those of the compound obtained in Example 44.

In the same manner as above, ethyl 7-benzenesulfinyl-1-(2,4-difluorophenyl)-6-fluoro-1,4-dihydro-4-oxo-1,8-naphthyridine-3-carboxylate was obtained, and the physical properties of this compound were identical with those of the compound obtained in Example 44.

EXAMPLE 60

In 15 ml of methylene chloride was dissolved 1.00 g of ethyl 1-(2,4-difluorophenyl)-7-ethylthio-6-fluoro-1,4-dihydro-4-oxo-1,8-naphthyridine-3-carboxylate, and 1.06 g of m-chloroperbenzoic acid (purity: 80%) was added thereto, after which the resulting mixture was subjected to reaction with ice-cooling for 30 minutes, and then at room temperature for 4 hours. The precipitates were removed by filtration, and to the filtrate thus obtained was added 10 ml of water, after which the pH thereof was adjusted to 7.5 with saturated aqueous sodium hydrogencarbonate solution. The organic layer was thereafter separated, washed successively with 10 ml of water and 10 ml of saturated aqueous sodium chloride solution, and then dried over anhydrous magnesium sulfate. The solvent was removed by distillation under reduced pressure, and to the residue thus obtained was added 10 ml of diethyl ether, after which the crystals thus deposited were collected by filtration to obtain 940 mg (yield 87.2%) of ethyl 1-(2,4-difluorophenyl)-7-ethylsulfonyl-6-fluoro-1,4-dihydro-4-oxo-1,8-naphthyridine-3-carboxylate having a melting point of 215°-217° C. The physical properties of this compound were identical with those of the compound obtained in Example 44.

In the same manner as above, ethyl 7-benzenesulfonyl-1-(2,4-difluorophenyl)-6-fluoro-1,4-dihydro-4-oxo-1,8-naphthyridine-3-carboxylate was obtained, and the physical properties of this compound were identical with those of the compound obtained in Example 44.

EXAMPLE 61

In 8.0 ml of dioxane was suspended 800 mg of ethyl 7-benzenesulfonyl-1-(2,4-difluorophenyl)-6-fluoro-1,4-dihydro-4-oxo-1,8-naphthyridine-3-carboxylate, and 4.9 ml of N hydrochloric acid was added thereto, after which the resulting mixture was subjected to reaction under reflux for 4 hours. The solvent was removed by distillation under reduced pressure, and the residue thus obtained was purified by a column chromatography [Wako Silica Gel C-200, eluant: benzene-ethyl acetate (10:1 by volume)] to obtain 560 mg (yield 74.3%) of 7-benzenesulfonyl-1-(2,4-difluorophenyl)-6-fluoro-1,4-dihydro-4-oxo-1,8-naphthyridine-3-carboxylic acid having a melting point of 252°-258° C.

Melting point: 259°-263° C. (recrystallized from dioxane).

IR (KBr) cm$^{-1}$: $\nu_{C=O}$ 1730.

NMR (DMSO-d$_6$) δ values: 7.05-7.85 (8H, m), 8.85 (1H, d, J=9 Hz), 8.98 (1H, s).

EXAMPLE 62

In 2.5 ml of phosphorus oxychloride was suspended 500 mg of ethyl 1-(2,4-difluorophenyl)-6-fluoro-1,4-dihydro-7-methoxy-4-oxo-1,8-naphthyridine-3-carboxylate, and the resulting suspension was subjected to reaction under reflux for 1.5 hours. Subsequently, the solvent was removed by distillation under reduced pressure, and the crystalline material thus obtained was washed with 10 ml of diethyl ether to obtain 430 mg (yield 85.0%) of ethyl 7-chloro-1-(2,4-difluorophenyl)-6-fluoro-1,4-dihydro-4-oxo-1,8-naphthyridine-3-carboxylate having a melting point of 216°–219° C. The physical properties of this compound were identical with those of the compound obtained in Example 51.

EXAMPLE 63

In 10 ml of conc. hydrochloric acid was suspended 500 mg of ethyl 7-chloro-1-(2,4-difluorophenyl)-6-fluoro-1,4-dihydro-4-oxo-1,8-naphthyridine-3-carboxylate, and the resulting suspension was subjected to reaction under reflux for 1 hour. The reaction mixture was diluted with 10 ml of water, and the crystals thus deposited were collected by filtration, and then washed with 2 ml of water to obtain 450 mg (yield 97.1%) of 7-chloro-1-(2,4-difluorophenyl)-6-fluoro-1,4-dihydro-4-oxo-1,8-naphthyridine-3-carboxylic acid having a melting point of 238°–242° C.

Melting point: 242.5°–243.5° C. (recrystallized from chloroform-ethanol (2:1 by volume))

EXAMPLE 64

In 5 ml of ethanol was suspended 150 mg of 3-aminopyrrolidine dihydrochloride, and 310 mg of triethylamine was added thereto to form a solution. Subsequently, 500 mg of ethyl 1-(2,4-difluorophenyl)-6-fluoro-1,4-dihydro-4-oxo-7-(2,4,6-triisopropylbenzenesulfonyloxy)-1,8-naphthyridine-3-carboxylate was added thereto, and the resulting mixture was subjected to reaction at room temperature for 2 hours. Subsequently, 6 ml of water was added to the reaction mixture, and the crystals thus deposited were collected by filtration, and washed with 5 ml of water to obtain 330 mg (yield 96.3%) of ethyl 7-(3-amino-1-pyrrolidinyl)-1-(2,4-difluorophenyl)-6-fluoro-1,4-dihydro-4-oxo-1,8-naphthyridine-3-carboxylate having a melting point of 200°–202° C.

Melting point: 206°–209° C. (recrystallized from ethyl acetate-ethanol (1:1 by volume)).

NMR (TFA-d$_1$) δ values: 1.48 (3H, t, J=7 Hz), 2.19–2.86 (2H, m), 3.33–4.90 (7H, m), 6.89–7.85 (3H, m), 8.18 (1H, d, J=11 Hz), 9.04 (1H, s).

In the same manner as above, the compounds shown in Table 13 were obtained.

TABLE 13

| Starting compound | | Physical properties of objective compound | Yield (%) |
|---|---|---|---|
| X | R² | | |
| F | 2,4-dichlorophenyl-SO₃— | Identical with the above physical properties | 90.2 |
| F | 2,4,5-trichlorophenyl-SO₃— | Same as above | 92.8 |
| F | 4-methylphenyl-SO₃— | Same as above | 55.5 |
| F | 2,4,6-trimethylphenyl-SO₃— | Same as above | 91.0 |
| H | 2,4,6-triisopropylphenyl-SO₃— | Melting point: 192–194° C. NMR (TFA-d$_1$) δ values: 1.49 (3H, t, J=7Hz), 2.13–3.13 (2H, m), 3.23–4.93 (7H, m), 7.03–7.73 (4H, m), 8.18 (1H, d, J=12Hz), 9.06 (1H, s) | 95.9 |

EXAMPLE 65

In 4 ml of methylene chloride was dissolved 270 mg of anhydrous piperazine, and 400 mg of ethyl 1-(2,4-difluorophenyl)-6-fluoro-1,4-dihydro-4-oxo-7-(2,4,6-triisopropylbenzenesulfonyloxy)-1,8-naphthyridine-3-carboxylate was added to the resulting solution, after which the resulting mixture was subjected to reaction with ice-cooling for 1 hour. To the reaction mixture were added 20 ml of ethyl acetate and 10 ml of water, and the organic layer was separated, washed successively with 10 ml of saturated aqueous sodium hydrogencarbonate solution and 10 ml of saturated aqueous sodium chloride solution, and then dried over anhydrous magnesium sulfate. The solvent was removed by distillation under reduced pressure, and to the crystalline material thus obtained was added 5 ml of diethyl ether, after which crystals were collected by filtration to obtain 250 mg (yield 91.2%) of ethyl 1-(2,4-difluorophenyl)-6-fluoro-1,4-dihydro-4-oxo-7-(1-piperazinyl)-1,8-naphthyridine-3-carboxylate having a melting point of 208°–211° C.

Melting point: 220°–223° C. (recrystallized from acetone-methanol (1:1 by volume)).

NMR (TFA-d₁) δ values: 1.50 (3H, t, J=7 Hz), 3.39–3.93 (4H, m), 3.93–4.44 (4H, m), 4.66 (2H, q, J=7 Hz), 6.89–7.82 (3H, m), 8.32 (1H, d, J=12 Hz), 9.14 (1H, s).

In the same manner as above, the results shown in Table 14 were obtained.

TABLE 14

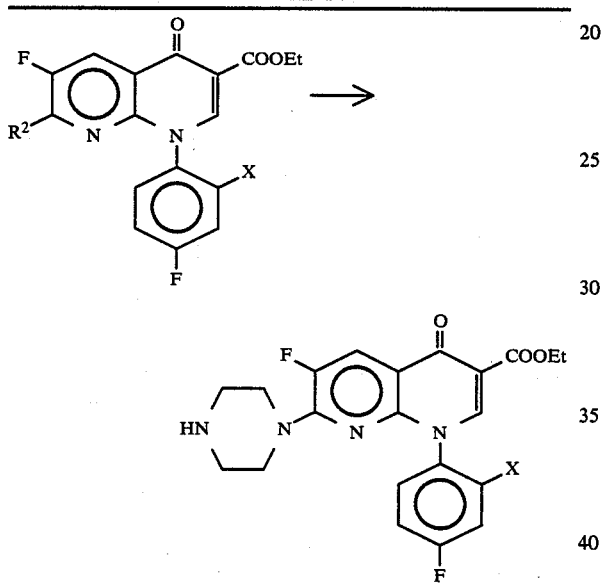

| Starting compound | | Physical properties of objective compound | Yield (%) |
|---|---|---|---|
| X | R² | | |
| H | 2-NO₂-C₆H₄-SO₃— | Melting point: 215–217° C. NMR(TFA-d₁) δ values: 1.51 (3H, t, J=7Hz), 3.40–3.88 (4H, m), 4.06–4.46 (4H, m), 4.70 (2H, q, J=7Hz), 7.16–7.78 (4H, m), 8.38 (1H, d, J=12Hz), 9.21 (1H, s) | 90.1 |
| H | 2,4,6-tri-i-Pr-C₆H₂-SO₃— | Same as above | 91.1 |
| F | MeSO₃— | Identical with the physical properties in Example 65 | 64.7 |
| F | Me₂CHSO₃— | Same as above | 70.6 |
| F | F₃CSO₃— | Same as above | 63.1 |
| F | 4-Cl-C₆H₄-SO₃— | Same as above | 42.7 |

TABLE 14-continued

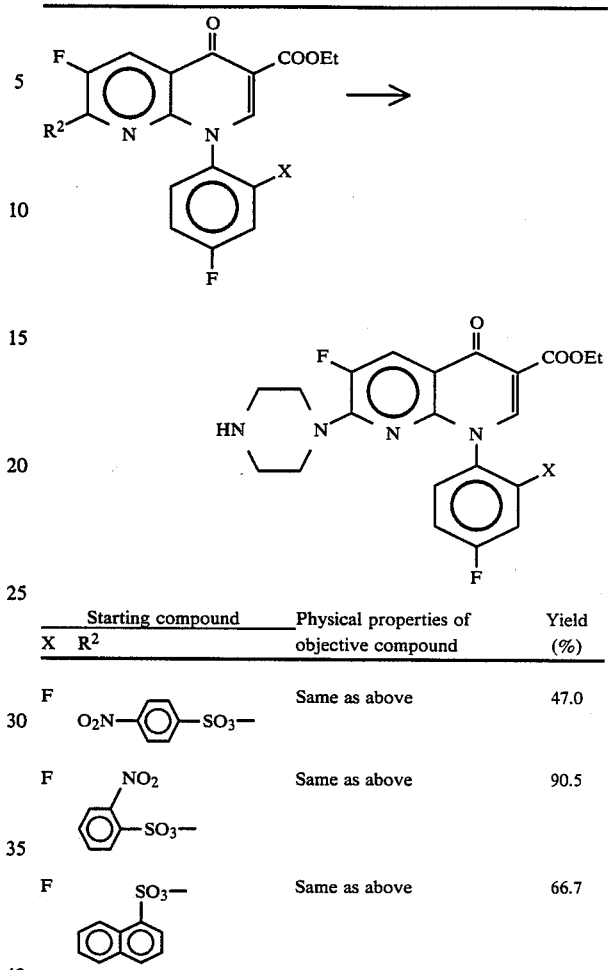

| Starting compound | | Physical properties of objective compound | Yield (%) |
|---|---|---|---|
| X | R² | | |
| F | 4-O₂N-C₆H₄-SO₃— | Same as above | 47.0 |
| F | 2-NO₂-C₆H₄-SO₃— | Same as above | 90.5 |
| F | 1-naphthyl-SO₃— | Same as above | 66.7 |

EXAMPLE 66

(1) In 2 ml of ethanol was suspended 64 mg of 3-aminopyrrolidine dihydrochloride, and 130 mg of triethylamine was added to the resulting suspension to form a solution. Subsequently, 200 mg of ethyl 1-(2,4-difluorophenyl)-7-diphenoxyphosphinyloxy-6-fluoro-1,4-dihydro-4-oxo-1,8-naphthyridine-3-carboxylate was added to the solution, and the resulting mixture was subjected to reaction at room temperature of 1 hour. Subsequently, 3 ml of water was added to the reaction mixture, and the crystals thus deposited were collected and washed with 3 ml of water to obtain 110 mg (yield 75.9%) of ethyl 7-(3-amino-1-pyrrolidinyl)-1-(2,4-difluorophenyl)-6-fluoro-1,4-dihydro-4-oxo-1,8-naphthyridine-3-carboxylate. The physical properties of this compound were identical with those of the compound obtained in Example 64.

(2) The same procedure as in (1) above was repeated, except that 170 mg of ethyl 7-diethoxyphosphinyloxy-1-(2,4-difluorophenyl)-6-fluoro-1,4-dihydro-4-oxo-1,8-naphthyridine-3-carboxylate was substituted for the ethyl 1-(2,4-difluorophenyl)-7-diphenoxyphosphinyloxy-6-fluoro-1,4-dihydro-4-oxo-1,8-naphthyridine-3-carboxylate to obtain 105 mg (yield 71.5%) of ethyl 7-(3-amino-1-pyrrolidinyl)-1-(2,4-difluorophenyl)-6-fluoro-1,4-dihydro-4-oxo-1,8-naphthyridine-3-carboxylate. The physical properties of this compound were identical with those of the compound obtained in Example 64.

EXAMPLE 67

In a mixture of 4.5 ml of ethanol and 4.5 ml of N,N-dimethylformamide was dissolved 400 mg of anhydrous piperazine, and 450 mg of ethyl 7-azido-1-(2,4-difluorophenyl)-6-fluoro-1,4-dihydro-4-oxo-1,8-naphthyridine-3-carboxylate was added to the resulting solution, after which the resulting mixture was subjected to reaction at 80° C. for 1 hour. The solvent was removed by distillation under reduced pressure, and to the residue thus obtained were added 30 ml of ethyl acetate and 30 ml of water, after which the pH thereof was adjusted to 1.0 with 2N hydrochloric acid. The aqueous layer was separated, and 15 ml of chloroform was added to the aqueous layer, after which the pH thereof was adjusted to 8.5 with 1N aqueous sodium hydroxide solution. The organic layer was separated, washed successively with 10 ml of water and 10 ml of saturated aqueous sodium chloride solution, and then dried over anhydrous magnesium sulfate. The solvent was removed by distillation under reduced pressure, and to the residue thus obtained was added 5 ml of diethyl ether, after which the crystals thus deposited were collected by filtration to obtain 420 mg (yield 84.0%) of ethyl 1-(2,4-difluorophenyl)-6-fluoro-1,4-dihydro-4-oxo-7-(1-piperazinyl)-1,8-naphthyridine-3-carboxylate. The physical properties of this compound were identical with those of the compound obtained in Example 65.

EXAMPLE 68

In 12 ml of N,N-dimethylformamide were suspended 400 mg of ethyl 1-(2,4-difluorophenyl)-6-fluoro-1,4-dihydro-4-oxo-7-phenylthio-1,8-naphthyridine-3-carboxylate and 380 mg of anhydrous piperazine, and the resulting suspension was subjected to reaction at 95° to 100° C. for 6 hours. Subsequently, the solvent was removed by distillation under reduced pressure, and to the residue thus obtained were added 10 ml of ethyl acetate and 30 ml of water, after which the pH thereof was adjusted to 0.5 with 6N hydrochloric acid. The aqueous layer was separated and 30 ml of ethyl acetate was added thereto, after which the pH thereof was adjusted to 9.0 with a 10% by weight aqueous potassium carbonate solution. The organic layer was separated, and the aqueous layer was extracted with two 20-ml portions of ethyl acetate, after which the extracts were combined with the organic layer. The combined layer was washed with 20 ml of saturated aqueous sodium chloride solution, and then dried over anhydrous magnesium sulfate. The solvent was removed by distillation under reduced pressure, and to the crystalline material thus obtained was added 5 ml of diethyl ether, after which crystals were collected by filtration to obtain 230 mg (yield 60.7%) of ethyl 1-(2,4-difluorophenyl)-6-fluoro-1,4-dihydro-4-oxo-7-(1-piperazinyl)-1,8-naphthyridine-3-carboxylate. The physical properties of this compound were identical with those of the compound obtained in Example 65.

EXAMPLE 69

(1) In 3 ml of ethanol was suspended 120 mg of 3-aminopyrrolidine dihydrochloride, and 250 mg of triethylamine was added thereto, after which 300 mg of ethyl 7-benzenesulfinyl-1-(2,4-difluorophenyl)-6-fluoro-1,4-dihydro-4-oxo-1,8-naphthyridine-3-carboxylate was added thereto. The resulting mixture was subjected to reaction at room temperature for 3 hours, and to the reaction mixture was added 10 ml of diethyl ether, after which crystals were collected by filtration, and washed with 12 ml of water to obtain 230 mg (yield 83.8%) of ethyl 7-(3-amino-1-pyrrolidinyl)-1-(2,4-difluorophenyl)-6-fluoro-1,4-dihydro-4-oxo-1,8-naphthyridine-3-carboxylate. The physical properties of this compound were identical with those of the compound obtained in Example 64.

(2) The same procedure as in (1) above was repeated, except that 270 mg of ethyl 1-(2,4-difluorophenyl)-7-ethylsulfinyl-6-fluoro-1,4-dihydro-4-oxo-1,8-naphthyridine-3-carboxylate was substituted for the ethyl 7-benzenesulfinyl-1-(2,4-difluorophenyl)-6-fluoro-1,4-dihydro-4-oxo-1,8-naphthyridine-3-carboxylate to obtain 230 mg (yield 83.6%) of ethyl 7-(3-amino-1-pyrrolidinyl)-1-(2,4-difluorophenyl)-6-fluoro-1,4-dihydro-4-oxo-1,8-naphthyridine-3-carboxylate. The physical properties of this compound were identical with those of the compound obtained in Example 64.

EXAMPLE 70

(1) In 3 ml of ethanol was suspended 120 mg of 3-aminopyrrolidine dihydrochloride, and 250 mg of triethylamine was added thereto to form a solution. Subsequently, 300 mg of ethyl 7-benzenesulfonyl-1-(2,4-difluorophenyl)-6-fluoro-1,4-dihydro-4-oxo-1,8-naphthyridine-3-carboxylate was added to the solution, and the resulting mixture was subjected to reaction at 45° to 50° C. for 4 hours. To the reaction mixture was added 10 ml of diethyl ether, and crystals were collected by filtration and washed with 12 ml of water to obtain 230 mg (yield 86.6%) of ethyl 7-(3-amino-1-pyrrolidinyl)-1-(2,4-difluorophenyl)-6-fluoro-1,4-dihydro-4-oxo-1,8-naphthyridine-3-carboxylate. The physical properties of this compound were identical with those of the compound obtained in Example 64.

(2) The same procedure as in (1) above was repeated, except that 270 mg of ethyl 1-(2,4-difluorophenyl)-7-ethylsulfonyl-6-fluoro-1,4-dihydro-4-oxo-1,8-naphthyridine-3-carboxylate was substituted for the ethyl 7-benzenesulfonyl-1-(2,4-difluorophenyl)-6-fluoro-1,4-dihydro-4-oxo-1,8-naphthyridine-3-carboxylate to obtain 225 mg (yield 84.9%) of ethyl 7-(3-amino-1-pyrrolidinyl)-1-(2,4-difluorophenyl)-6-fluoro-1,4-dihydro-4-oxo-1,8-naphthyridine-3-carboxylate. The physical properties of this compound were identical with those of the compound obtained in Example 64.

EXAMPLE 71

In 2 ml of methylene chloride was suspended 70 mg of N-acetylpiperazine monohydrochloride, and 80 mg of triethylamine was added thereto to form a solution. Subsequently, 200 mg of ethyl 1-(2,4-difluorophenyl)-6-fluoro-1,4-dihydro-4-oxo-7-(2,4,6-triisopropylbenzenesulfonyloxy)-1,8-naphthyridine-3-carboxylate was added thereto, and the resulting mixture was subjected to reaction at room temperature for 2 hours. To the reaction mixture were added 8 ml of methylene chloride and 10 ml of water, and the organic layer was separated, washed successively with 10 ml of water and 10 ml of saturated aqueous sodium chloride solution, and then dried over anhydrous magnesium sulfate. The solvent was removed by distillation under reduced pressure, and to the residue thus obtained was added 5 ml of diethyl ether, after which the crystals thus deposited were collected by filtration to obtain 140 mg (yield 93.1%) of ethyl 7-(4-acetyl-1-piperazinyl)-1-(2,4-difluorophenyl)-6-fluoro-1,4-dihydro-4-oxo-1,8-naphthyridine-3-carboxylate having a melting point of 217°-219° C. The physical properties of this compound were identical with those of the compound obtained in Example 39.

EXAMPLE 72

In 6 ml of 6N hydrochloric acid was suspended 1.00 g of ethyl 7-(3-amino-1-pyrrolidinyl)-1-(2,4-difluorophenyl)-6-fluoro-1,4-dihydro-4-oxo-1,8-naphthyridine-3-carboxylate, and the resulting suspension was subjected to reaction under reflux for 2 hours. Subsequently, 6 ml of water was added thereto and crystals were collected by filtration, and then washed with 2 ml of water to obtain 920 mg (yield 90.2%) of 7-(3-amino-1-pyrrolidinyl)-1-(2,4-difluorophenyl)-6-fluoro-1,4-dihydro-4-oxo-1,8-naphthyridine-3-carboxylic acid hydrochloride having a melting point of 247°-250° C. (decomp.). The physical properties of this compound were identical with those of the compound obtained in Example 54.

In the same manner as above, 7-(3-amino-1-pyrrolidinyl)-6-fluoro-1-(4-fluorophenyl)-1,4-dihydro-4-oxo-1,8-naphthyridine-3-carboxylic acid hydrochloride was obtained.

Melting point: 210°-217° C. (decomp.).

NMR (TFA-$d_1$) δ values: 2.20-2.85 (2H, m), 3.48-4.98 (5H, m), 7.07-7.78 (4H, m), 8.18 (1H, d, J=11 Hz), 9.18 (1H, s).

EXAMPLE 73

In 1.2 ml of 6N hydrochloric acid was suspended 200 mg of ethyl 1-(2,4-difluorophenyl)-6-fluoro-1,4-dihydro-4-oxo-7-(1-piperazinyl)-1,8-naphthyridine-3-carboxylate, and the resulting suspension was subjected to reaction under reflux for 2 hours. Subsequently, 2 ml of water was added thereto and crystals were collected by filtration and washed with 1 ml of water to obtain 190 mg (yield 93.2%) of 1-(2,4-difluorophenyl)-6-fluoro-1,4-dihydro-4-oxo-7-(1-piperazinyl)-1,8-naphthyridine-3-carboxylic acid hydrochloride having a melting point of 249°-252° C. (decomp.).

Melting point: 249°-252° C. (decomp.) (recrystallized from conc. hydrochloric acid-methanol (1:2 by volume))

NMR (TFA-$d_1$) δ values: 3.33-3.92 (4H, m), 3.92-4.50 (4H, m), 6.90-7.90 (3H, m), 8.30 (1H, d, J=12 Hz), 9.18 (1H, s).

EXAMPLE 74

In 1 ml of 6N hydrochloric acid was suspended 100 mg of ethyl 1-(2,4-difluorophenyl)-7-[3-(N,N-dimethylaminomethyleneimino)-1-pyrrolidinyl]-6-fluoro-1,4-dihydro-4-oxo-1,8-naphthyridine-3-carboxylate, and the resulting suspension was subjected to reaction under reflux for 2 hours. Subsequently, the solvent was removed by distillation under reduced pressure, and to the crystalline material thus obtained was added 1 ml of ethanol, after which crystals were collected by filtration to obtain 85 mg (yield 94.0%) of 7-(3-amino-1-pyrrolidinyl)-1-(2,4-difluorophenyl)-6-fluoro-1,4-dihydro-4-oxo-1,8-naphthyridine-3-carboxylic acid hydrochloride. The physical properties of this compound were identical with those of the compound obtained in Example 54.

EXAMPLE 75

In 5 ml of 6N hydrochloric acid was dissolved 500 mg of ethyl 7-(3-acetylamino-1-pyrrolidinyl)-1-(2,4-difluorophenyl)-6-fluoro-1,4-dihydro-4-oxo-1,8-naphthyridine-3-carboxylate, and the resulting solution was subjected to reaction under reflux for 4 hours. Subsequently, the crystals thus deposited were collected by filtration and washed with 1 ml of water to obtain 390 mg (yield 84.0%) of 7-(3-amino-1-pyrrolidinyl)-1-(2,4-difluorophenyl)-6-fluoro-1,4-dihydro-4-oxo-1,8-naphthyridine-3-carboxylic acid hydrochloride having a melting point of 247°-250° C. (decomp.). The physical properties of this compound were identical with those of the compound obtained in Example 54.

EXAMPLE 76

In the same manner as in Example 75, except that the reaction time was altered to 2 hours, 1-(2,4-difluorophenyl)-6-fluoro-7-(1-piperazinyl)-1,4-dihydro-4-oxo-1,8-naphthyridine-3-carboxylic acid hydrochloride was obtained in a yield of 91.5%. The physical properties of this compound were identical with those of the compound obtained in Example 73.

What is claimed is:

1. A 5-fluoronicotinic acid derivative of the formula:

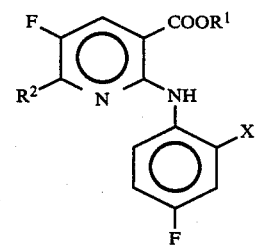

wherein $R^1$ represents a hydrogen atom or a carboxyl protecting group; $R^2$ represents a halogen atom, a hydroxyl group, an azido group, $C_{1-12}$ alkoxy, substituted $C_{1-12}$ alkoxy, $C_{1-12}$ alkylthio, substituted $C_{1-12}$ alkylthio, phenylthio, naphthylthio, substituted phenylthio, substituted naphthylthio, $C_{1-5}$ alkanesulfinyl, substituted $C_{1-5}$ alkanesulfinyl, benzenesulfinyl, naphthalenesulfinyl, substituted benzenesulfinyl, substituted naphthalenesulfinyl, $C_{1-5}$ alkanesulfonyl, substituted $C_{1-5}$ alkanesulfonyl, benzenesulfonyl, naphthalenesulfonyl, substituted benzenesulfonyl, substituted naphthalenesulfonyl, $C_{1-5}$ alkanesulfonyloxy, substituted $C_{1-5}$ alkanesulfonyloxy, benzenesulfonyloxy, naphthalenesulfonyloxy, substituted benzenesulfonyloxy, substituted naphthalenesulfonyloxy, di-$C_{1-5}$-alkoxyphosphinyloxy, substituted di-$C_{1-5}$-alkoxyphosphinyloxy diphenoxyphosphinyloxy, or substituted diphenoxyphosphinyloxy, wherein the substituent groups are selected from the group consisting of halogen, nitro, lower alkyl and lower alkoxy, a 3-amino-1-pyrrolidinyl group in which the amino group may be protected or a 1-piperazinyl group in which the imino group may be protected; and X represents a hydrogen atom or a fluorine atom, or a salt of the derivative or a reactive derivative, in the carboxyl group thereof, selected from the group consisting of acid halides, acid anhydrides, mixed acid anhydrides, active esters and active acid amides.

2. A 5-fluoronicotinic acid derivative or a salt thereof according to claim 1, wherein $R^2$ represents a halogen atom, a hydroxyl group, a 3-amino-1-pyrrolidinyl group in which the amino group may be protected, a 1-piperazinyl group in which the imino group may be protected or $C_{1-12}$ alkoxy, substituted $C_{1-12}$ alkoxy, $C_{1-12}$ alkylthio, substituted $C_{1-12}$ alkylthio, phenylthio, naphthylthio, substituted phenylthio, substituted naphthylthio, $C_{1-5}$ alkanesulfonyloxy, substituted $C_{1-5}$ alkanesulfonyloxy, benzenesulfonyloxy or naphthalenesulfonyloxy, wherein said substituents are selected from the group consisting of halogen, nitro, lower alkyl and lower alkoxy.

3. A 5-fluoronicotinic acid derivative or a salt thereof according to claim 1, wherein X represents a fluorine atom.

4. A 5-fluoronicotinic acid derivative or a salt thereof according to claim 3, wherein $R^2$ represents a halogen atom, a hydroxyl group, a 3-amino-1-pyrrolidinyl group in which the amino group may be protected or $C_{1-12}$ alkoxy, substituted $C_{1-12}$ alkoxy, benzenesulfonyloxy, naphthalenesulfonyloxy, substituted benzenesulfonyl or substituted naphthalenesulfonyloxy, wherein said substituents are selected from the group consisting of halogen, nitro, lower alkyl and lower alkoxy.

5. A 2-(5-fluoronicotinoyl)acetic acid derivative of the formula:

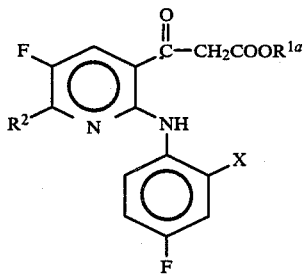

wherein $R^{1a}$ represents a carboxyl-protecting group; $R^2$ represents a halogen atom, a hydroxyl group, an azido group, $C_{1-12}$ alkoxy, substituted $C_{1-12}$ alkoxy, $C_{1-12}$ alkylthio, substituted $C_{1-12}$ alkylthio, phenylthio, naphthylthio, substituted phenylthio, substituted naphthylthio, $C_{1-5}$ alkanesulfinyl, substituted $C_{1-5}$ alkanesulfinyl, benzenesulfinyl, naphthalenesulfinyl, substituted benzenesulfinyl, substituted naphthalenesulfinyl, $C_{1-5}$ alkanesulfonyl, substituted $C_{1-5}$ alkanesulfonyl, benzenesulfonyl, naphthalenesulfonyl, substituted benzenesulfonyl, substituted naphthalenesulfonyl, $C_{1-5}$ alkanesulfonyloxy, substituted $C_{1-5}$ alkanesulfonyloxy, benzenesulfonyloxy, naphthalenesulfonyloxy, substituted benzenesulfonyloxy, substituted naphthalenesulfonyloxy, di-$C_{1-5}$-alkoxyphosphinyloxy, substituted di-$C_{1-5}$-alkoxyphosphinyloxy diphenoxyphosphinyloxy, or substituted diphenoxyphosphinyloxy, wherein the substituent groups are selected from the group consisting of halogen, nitro, lower alkyl and lower alkoxy, a 3-amino-1-pyrrolidinyl group in which the amino group may be protected or a 1-piperazinyl group in which the imino group may be protected; and X represents a hydrogen atom or a fluorine atom, or a salt thereof.

6. A 2-(5-fluoronicotinoyl)acetic acid derivative or a salt thereof according to claim 5, wherein $R^2$ represents a halogen atom, a hydroxyl group, a 3-amino-pyrrolidinyl group in which the amino group may be protected, a piperazinyl group in which the imino group may be protected or $C_{1-12}$ alkoxyl, substituted $C_{1-12}$ alkoxy, $C_{1-12}$ alkylthio, substituted $C_{1-12}$ alkylthio, phenylthio, naphthylthio, substituted phenylthio, substituted naphthylthio, $C_{1-5}$ alkanesulfonyloxy, substituted $C_{1-5}$ alkanesulfonyloxy, benzenesulfonyloxy, naphthalenesulfonyloxy, substituted benzenesulfonyloxy or substituted naphthalenesulfonyloxy, wherein said substituents are selected from the group consisting of halogen, nitro, lower alkyl and lower alkoxy.

7. A 2-(5-fluoronicotinoyl)acetic acid derivative or a salt thereof according to claim 6, wherein X represents a fluorine atom.

8. A 2-(5-fluoronicotinoyl)acetic acid derivative or a salt thereof according to claim 7, wherein $R^2$ represents a halogen atom, a hydroxyl group, a 3-amino-1-pyrrolidinyl group in which the amino group may be protected or $C_{1-12}$ alkoxy, substituted $C_{1-12}$ alkoxy, benzenesulfonyloxy, naphthalenesulfonyloxy, substituted benzenesulfonyloxy or substituted naphthalenesulfonyloxy, wherein said substituents are selected from the group consisting of halogen, nitro, lower alkyl and lower alkoxy.

* * * * *